(12) United States Patent
Ko et al.

(10) Patent No.: US 11,407,819 B2
(45) Date of Patent: Aug. 9, 2022

(54) COMPOSITIONS AND USE OF A FIBRINOGEN BINDING MOTIF PRESENT IN EFB AND COA FOR THERAPEUTICS AND VACCINES AGAINST *STAPHYLOCOCCUS AUREUS*

(71) Applicants: THE TEXAS A&M UNIVERSITY SYSTEM, College Station, TX (US); Università degli Studi di Pavia, Pavia (IT); Technische Universität Braunschweig, Braunschweig (DE)

(72) Inventors: Ya-Ping Ko, Sugar Land, TX (US); Magnus Hook, Houston, TX (US); Srishtee Arora, Houston, TX (US); Livia Visai, Rosate (IT); Federico Bertoglio, Spinadesco (IT); Michael Hust, Braunschweig (DE); Doris Meier, Andreasberg (DE)

(73) Assignees: The Texas A&M University System, College Station, TX (US); Technische Universität Braunschweig, Braunschweig (DE); Università Degli Studi Di Pavia, Pavia (IT)

( * ) Notice: Subject to any disclaimer, the term of this patent is extended or adjusted under 35 U.S.C. 154(b) by 0 days.

(21) Appl. No.: 16/879,272

(22) Filed: May 20, 2020

(65) Prior Publication Data
US 2020/0283508 A1 Sep. 10, 2020

Related U.S. Application Data

(63) Continuation-in-part of application No. 15/029,896, filed as application No. PCT/US2014/060772 on Oct. 15, 2014, now abandoned.

(60) Provisional application No. 61/891,233, filed on Oct. 15, 2013.

(51) Int. Cl.
*A61K 39/085* (2006.01)
*C07K 16/12* (2006.01)
*A61K 47/68* (2017.01)

(52) U.S. Cl.
CPC ........ *C07K 16/1271* (2013.01); *A61K 39/085* (2013.01); *A61K 47/6803* (2017.08); *C07K 2317/24* (2013.01); *C07K 2317/565* (2013.01); *C07K 2317/76* (2013.01)

(58) Field of Classification Search
None
See application file for complete search history.

*Primary Examiner* — Sarvamangala Devi
(74) *Attorney, Agent, or Firm* — Winstead PC

(57) ABSTRACT

The present disclosure provides methods and composition including vaccines, monoclonal antibodies, polyclonal antibodies, chimeric molecule of an extracellular fibrinogen binding protein (Efb) and targeted agent delivery pharmaceutical composition comprising at least a portion of a modified N-terminus region, at least a portion of a modified C-terminus region, or both, wherein the modified extracellular fibrinogen binding protein results in inhibiting the fibrinogen binding, C3 binding, or both or administering to a subject a pharmacologically effective amount of a vaccine in a pharmaceutically acceptable excipient, comprising a modified extracellular fibrinogen binding protein comprising at least a portion of a modified N-terminus region, at least a portion of a modified C-terminus region, or both, wherein the modified extracellular fibrinogen binding protein results in not shielding the staphylococcus bacterium from recognition by a phagocytic receptor.

11 Claims, 24 Drawing Sheets
Specification includes a Sequence Listing.

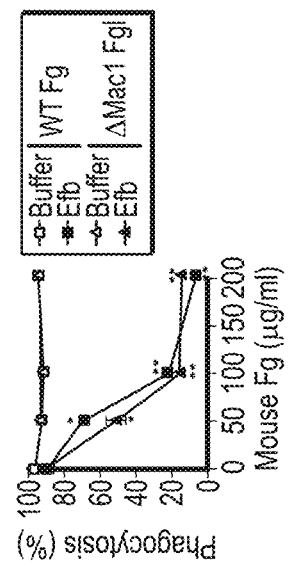
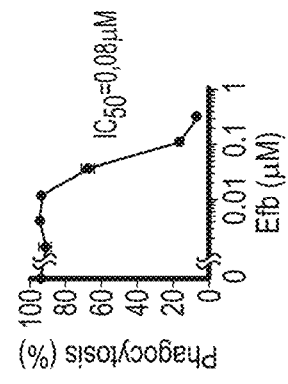
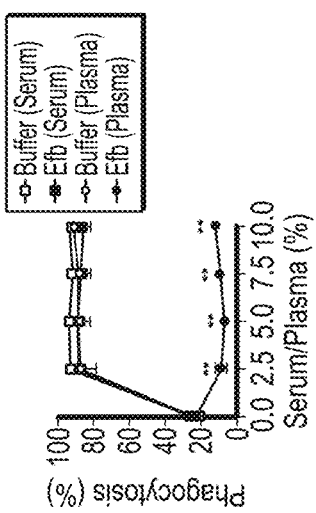
FIG. 1A
FIG. 1B
FIG. 1C
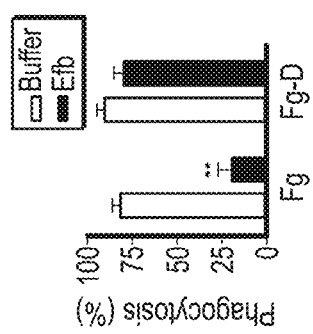
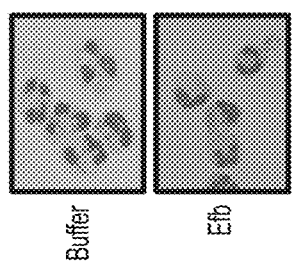
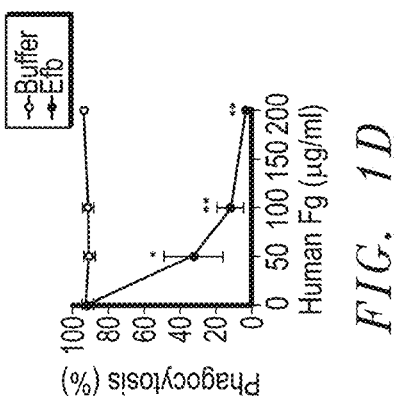
FIG. 1D
FIG. 1E
FIG. 1F

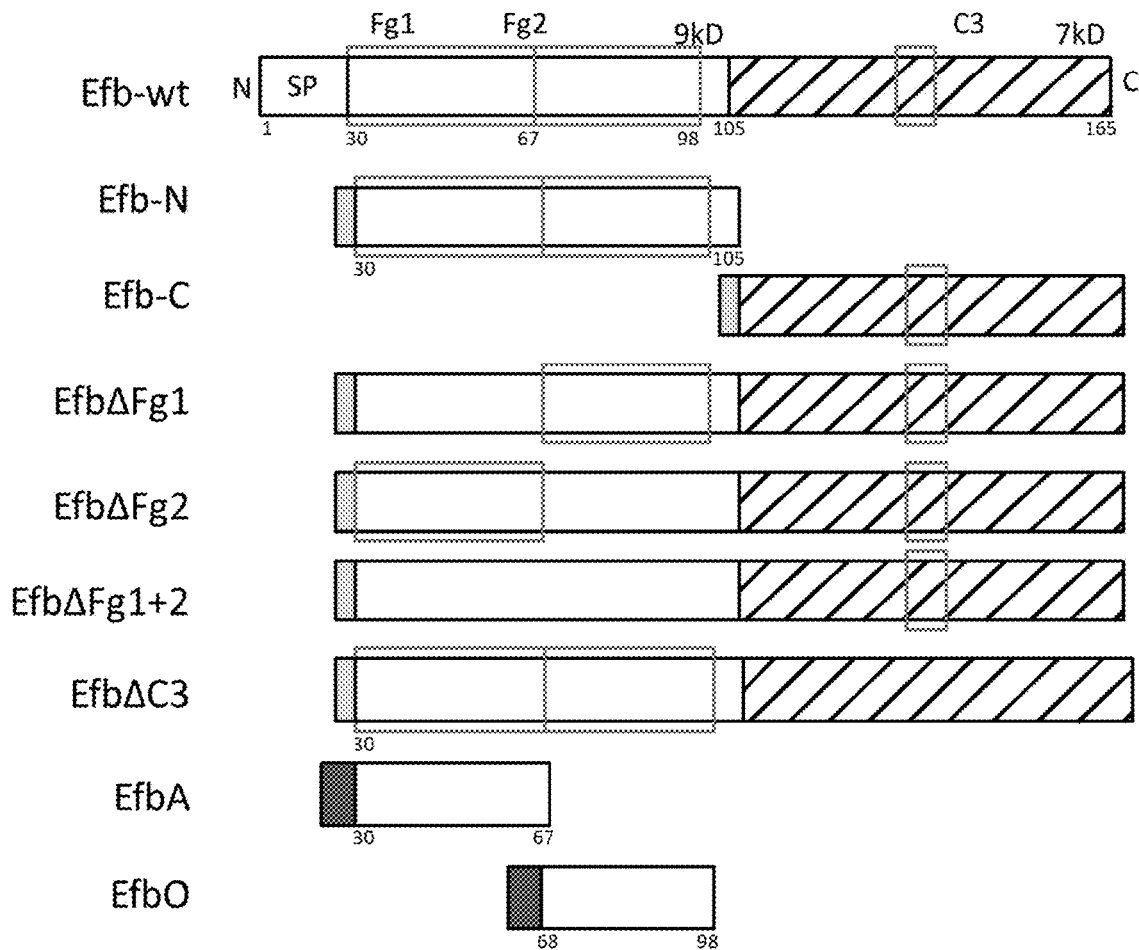
FIG. 2A
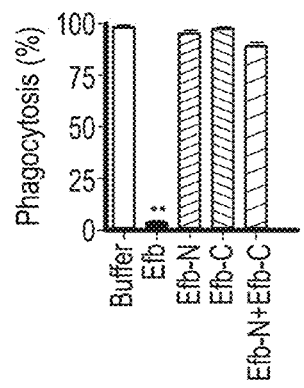 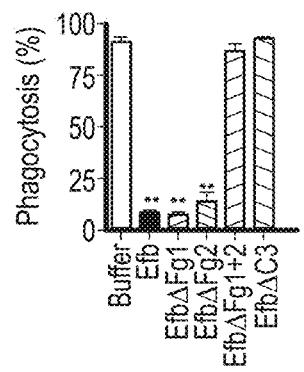
FIG. 2B    FIG. 2C

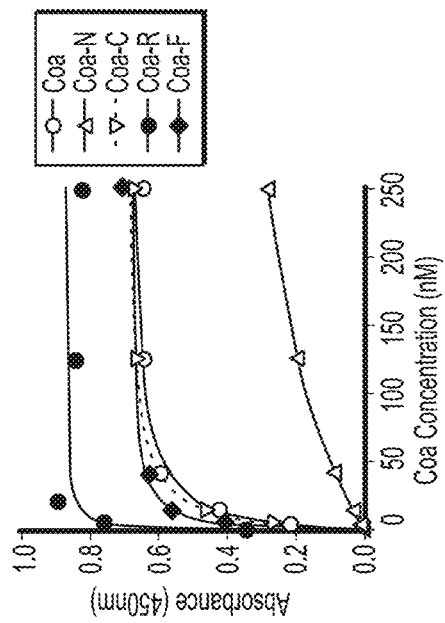
*FIG. 9B*
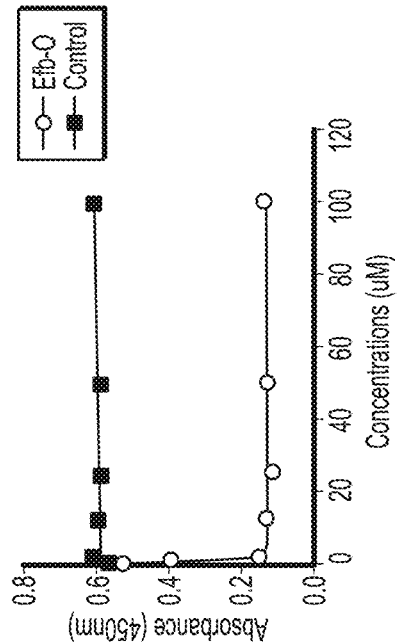
*FIG. 9D*
| Protein | $K_m$(nM) | $R^2$ |
|---|---|---|
| Coa | 8.9 | 0.995 |
| Coa-N | 203.6 | 0.991 |
| Coa-C | 7.5 | 0.996 |
| Coa-R | 0.8 | 0.994 |
| Coa-F | 3.2 | 0.986 |
*FIG. 9C*

| SEQ ID Number | PEPTIDE Sequence | Name |
|---|---|---|
| SEQ ID NO:1 | KYIKFKHDYNILEFNDGTFEYGARPQFNKPA | |
| SEQ ID NO: 2 | KYIKFKHDYNILEFNDGTFEYGARPQFN | 0 |
| SEQ ID NO: 3 | AYIKFKHDYNILEFNDGTFEYGARPQFN | 01 |
| SEQ ID NO: 4 | KAIKFKHDYNILEFNDGTFEYGARPQFN | 02 |
| SEQ ID NO: 5 | KYAKFKHDYNILEFNDGTFEYGARPQFN | 03 |
| SEQ ID NO: 6 | KYIAFKHDYNILEFNDGTFEYGARPQFN | 04 |
| SEQ ID NO: 7 | KYIKAKHDYNILEFNDGTFEYGARPQFN | 05 |
| SEQ ID NO: 8 | KYIKFAHDYNILEFNDGTFEYGARPQFN | 06 |
| SEQ ID NO: 9 | KYIKFKADYNILEFNDGTFEYGARPQFN | 07 |
| SEQ ID NO: 10 | KYIKFKHAYNILEFNDGTFEYGARPQFN | 08 |
| SEQ ID NO: 11 | KYIKFKHDANILEFNDGTFEYGARPQFN | 09 |
| SEQ ID NO: 12 | KYIKFKHDYAILEFNDGTFEYGARPQFN | 010 |
| SEQ ID NO: 13 | KYIKFKHDYNALEFNDGTFEYGARPQFN | 011 |
| SEQ ID NO: 14 | KYIKFKHDYNIAEFNDGTFEYGARPQFN | 012 |
| SEQ ID NO: 15 | KYIKFKHDYNILAFNDGTFEYGARPQFN | 013 |
| SEQ ID NO: 16 | KYIKFKHDYNILEANDGTFEYGARPQFN | 014 |
| SEQ ID NO: 17 | KYIKFKHDYNILEFADGTFEYGARPQFN | 015 |
| SEQ ID NO: 18 | KYIKFKHDYNILEFNAGTFEYGARPQFN | 016 |
| SEQ ID NO: 19 | KYIKFKHDYNILEFNDATFEYGARPQFN | 017 |
| SEQ ID NO: 20 | KYIKFKHDYNILEFNDGAFEYGARPQFN | 018 |
| SEQ ID NO: 21 | KYIKFKHDYNILEFNDGTAEYGARPQFN | 019 |
| SEQ ID NO: 22 | KYIKFKHDYNILEFNDGTFAYGARPQFN | 020 |
| SEQ ID NO: 23 | KYIKFKHDYNILEFNDGTFEAGARPQFN | 021 |
| SEQ ID NO: 24 | KYIKFKHDYNILEFNDGTFEYAARPQFN | 022 |
| SEQ ID NO: 25 | KYIKFKHDYNILEFNDGTFEYGSRPQFN | 023 |
| SEQ ID NO: 26 | KYIKFKHDYNILEFNDGTFEYGAAPQFN | 024 |
| SEQ ID NO: 27 | KYIKFKHDYNILEFNDGTFEYGARAQFN | 025 |
| SEQ ID NO: 28 | KYIKFKHDYNILEFNDGTFEYGARPAFN | 026 |
| SEQ ID NO: 29 | KYIKFKHDYNILEFNDGTFEYGARPQAN | 027 |
| SEQ ID NO: 30 | KYIKFKHDYNILEFNDGTFEYGARPQFA | 028 |

*FIG. 10A*

SEQ ID NO: 2 KYIKFKHDYNILEFNDGTFEYGARPQFN

Col-Newman SEQ ID NO:223 EGSSSKLEIK PQGTESTLKG TQGESSDIEV KPQATETTEA SQYGPRPQFN 470

Col-Newman SEQ ID NO: 224 KTPKYVKYRD AGTGIREYND GTFGYEARPR FNKPSETNAY NVTTHANKGQ 519
Efb-o SEQ ID NO: 62 KYIKFKHDYN ILEFNDGTFEYGARPQFNKPA Col-Newman SEQ ID NO:31 VSYGARPTYK KPSETNAYNVT 540

FIG. 11A

Coa SEQ ID NO:32 474 KYVKYRDAGTGIREYNDGTFGYEARPRFNKPS 505
Efb-O SEQ ID NO:2      KY_I_KFKHDYN-ILEFNDGTFEYGARP_QFN_---

FIG. 11B

Coa SEQ ID NO:33 506 ---ETNAYNVTHANGQVSYGARPTYKKPS 532
Efb-O SEQ ID NO:2      KYIKFKHDYNILEFNDGTFEYGARPQFN---

FIG. 11C

| | | |
|---|---|---|
| SEQ ID NO:34 | ETNAYNVTTHANGQVSYGARPTYKKPS | Coa-RI |
| SEQ ID NO:35 | ATNAYNVTTHANGQVSYGARPTYKKPS | Coa-RI-1 |
| SEQ ID NO:36 | EANAYNVTTHANGQVSYGARPTYKKPS | Coa-RI-2 |
| SEQ ID NO:37 | ETAAYNVTTHANGQVSYGARPTYKKPS | Coa-RI-3 |
| SEQ ID NO:38 | ETNSYNVTTHANGQVSYGARPTYKKPS | Coa-RI-4 |
| SEQ ID NO:39 | ETNAANVTTHANGQVSYGARPTYKKPS | Coa-RI-5 |
| SEQ ID NO:40 | ETNAYAVTTHANGQVSYGARPTYKKPS | Coa-RI-6 |
| SEQ ID NO:41 | ETNAYNATTHANGQVSYGARPTYKKPS | Coa-RI-7 |
| SEQ ID NO:42 | ETNAYNVATHANGQVSYGARPTYKKPS | Coa-RI-8 |
| SEQ ID NO:43 | ETNAYNVTAHANGQVSYGARPTYKKPS | Coa-RI-9 |
| SEQ ID NO:44 | ETNAYNVTTAANGQVSYGARPTYKKPS | Coa-RI-10 |
| SEQ ID NO:45 | ETNAYNVTTHSNGQVSYGARPTYKKPS | Coa-RI-11 |
| SEQ ID NO:46 | ETNAYNVTTHAAGQVSYGARPTYKKPS | Coa-RI-12 |
| SEQ ID NO:47 | ETNAYNVTTHANAQVSYGARPTYKKPS | Coa-RI-13 |
| SEQ ID NO:48 | ETNAYNVTTHANGAVSYGARPTYKKPS | Coa-RI-14 |
| SEQ ID NO:49 | ETNAYNVTTHANGQASYGARPTYKKPS | Coa-RI-15 |
| SEQ ID NO:50 | ETNAYNVTTHANGQVAYGARPTYKKPS | Coa-RI-16 |
| SEQ ID NO:51 | ETNAYNVTTHANGQVSAGARPTYKKPS | Coa-RI-17 |
| SEQ ID NO:52 | ETNAYNVTTHANGQVSYAARPTYKKPS | Coa-RI-18 |
| SEQ ID NO:53 | ETNAYNVTTHANGQVSYGSRPTYKKPS | Coa-RI-19 |
| SEQ ID NO:54 | ETNAYNVTTHANGQVSYGAAPTYKKPS | Coa-RI-20 |
| SEQ ID NO:55 | ETNAYNVTTHANGQVSYGARATYKKPS | Coa-RI-21 |
| SEQ ID NO:56 | ETNAYNVTTHANGQVSYGARPAYKKPS | Coa-RI-22 |
| SEQ ID NO:57 | ETNAYNVTTHANGQVSYGARPTAKKPS | Coa-RI-23 |
| SEQ ID NO:58 | ETNAYNVTTHANGQVSYGARPTYAKPS | Coa-RI-24 |
| SEQ ID NO:59 | ETNAYNVTTHANGQVSYGARPTYKAPS | Coa-RI-25 |
| SEQ ID NO:60 | ETNAYNVTTHANGQVSYGARPTYKKAS | Coa-RI-26 |
| SEQ ID NO:61 | ETNAYNVTTHANGQVSYGARPTYKKPA | Coa-RI-27 |

*FIG. 12A*

```
Efb-O   SEQ ID NO:1   KYIKFKHDYNILEFNDGTFEYGARPQFNKPA
Coa-RI  SEQ ID NO:34  -----ETNAYNVTTHANGQVSYGARPTYKKPS
```

FIG. 12C

```
SEQ ID NO:63   474  KYVKYRDAGTGIREYNDGTFGYEARPRFNKPS  506
SEQ ID NO:225  506  -----ETNAYNVTTHANGQVSYGARPTYKKPS  532
SEQ ID NO:226  533  -----ETNAYNVTTHANGQVSYGARPTQNKPS  559
SEQ ID NO:227  560  -----KTNAYNVTTHGNGQVSYGARPTQNKPS  586
SEQ ID NO:228  587  -----KTNAYNVTTHANGQVSYGARPTYKKPS  613
SEQ ID NO:229  614  -----KTNAYNVTTHADGTATYGPRVT--K--  636
```

FIG. 12D

| | | |
|---|---|---|
| sCoa RI$_4$ Coa$_{499-525}$ | SEQ ID NO: 64 | PRFNKPSETNAYNVTTHANGQVSYGAR |
| sCoa RI$_3$ Coa$_{502-528}$ | SEQ ID NO: 65 | NKPSETNAYNVTTHANGQVSYGARPTY |
| sCoa RI  Coa$_{506-532}$ | SEQ ID NO: 34 | ETNAYNVTTHANGQVSYGARPTYKKPS |
| sCoa RI$_2$ Coa$_{509-535}$ | SEQ ID NO: 66 | AYNVTTHANGQVSYGARPTYKKPSETN |
| sCoa RV$_1$ Coa$_{610-636}$ | SEQ ID NO: 67 | KKPSKTNAYNVTTHADGTATYGPRVTK |
| sCoa RV$_2$ Coa$_{605-631}$ | SEQ ID NO: 68 | ARPTYKKPSKTNAYNVTTHADGTATYG |
| sCoa RV$_3$ Coa$_{602-628}$ | SEQ ID NO: 69 | SYGARPTYKKPSKTNAYNVTTHADGTA |
| sCoa RV$_4$ Coa$_{599-625}$ | SEQ ID NO: 70 | GQVSYGARPTYKKPSKTNAYNVTTHAD |

FIG. 13A

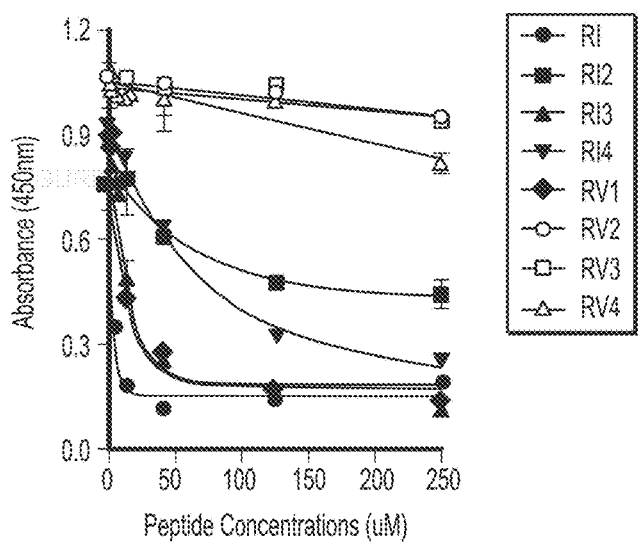

FIG. 13B

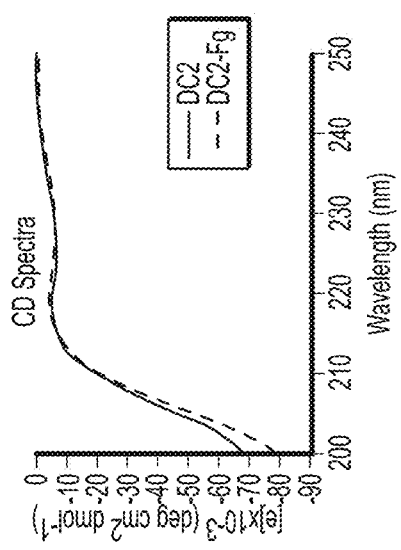
FIG. 16B
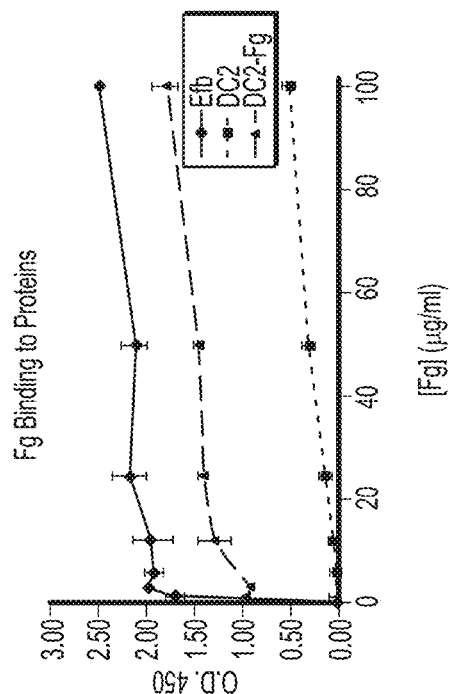
FIG. 16D
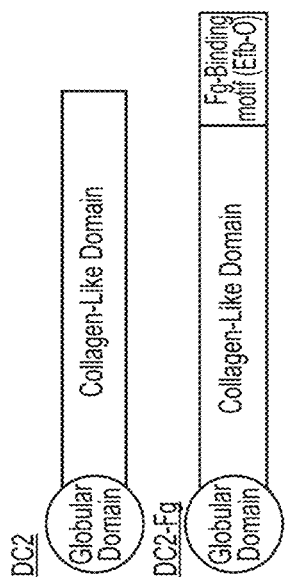
FIG. 16A
FIG. 16C

| ANTIBODY | $K_d$ app (M) for CoaC | $K_d$ app (M) for CoaF | $K_d$ app (M) for CoaR0 |
|---|---|---|---|
| FBE5-A5 | $5.34 \times 10^{-9}$ | $1.47 \times 10^{-9}$ | $1.86 \times 10^{-9}$ |
| FBE5-A6 | $1.24 \times 10^{-9}$ | $1.15 \times 10^{-9}$ | $1.9 \times 10^{-9}$ |
| FBE5-A12 | $5.55 \times 10^{-10}$ | $6.47 \times 10^{-10}$ | $2.44 \times 10^{-9}$ |
| FBE5-B9 | $1.74 \times 10^{-9}$ | $1.12 \times 10^{-9}$ | $2.19 \times 10^{-9}$ |
| FBE5-C1 | $1.13 \times 10^{-9}$ | $4.59 \times 10^{-9}$ | $2.43 \times 10^{-8}$ |
| FBE5-C8 | $1.35 \times 10^{-8}$ | $7 \times 10^{-9}$ | $1.93 \times 10^{-7}$ |
| FBE5-D9 | $7.79 \times 10^{-10}$ | $5.36 \times 10^{-10}$ | $1.14 \times 10^{-9}$ |
| FBE5-D10 | $1.4 \times 10^{-9}$ | $9.5 \times 10^{-10}$ | $8.56 \times 10^{-10}$ |
| FBE5-E5 | $6.27 \times 10^{-9}$ | $9.5 \times 10^{-9}$ | $8.64 \times 10^{-7}$ |
| FBE5-F9 | $2.85 \times 10^{-9}$ | $1.63 \times 10^{-9}$ | $3.16 \times 10^{-9}$ |
| FBE5-F11 | $5.13 \times 10^{-10}$ | $2.44 \times 10^{-10}$ | $2.13 \times 10^{-10}$ |

FIG. 19

| ANTIBODY | $K_d$ app (M) for EfbN | $K_d$ app (M) for EfbA | $K_d$ app (M) for EfbO |
|---|---|---|---|
| FBE5-A5 | $3.24 \times 10^{-9}$ | $4.38 \times 10^{-9}$ | $4.27 \times 10^{-9}$ |
| FBE5-A6 | $3.54 \times 10^{-9}$ | $8.54 \times 10^{-9}$ | $1.3 \times 10^{-8}$ |
| FBE5-A12 | $8.66 \times 10^{-9}$ | $7.28 \times 10^{-8}$ | $3.51 \times 10^{-8}$ |
| FBE5-B9 | $3.45 \times 10^{-9}$ | $2.59 \times 10^{-8}$ | $8.27 \times 10^{-9}$ |
| FBE5-C1 | $2.44 \times 10^{-8}$ | $4.09 \times 10^{-8}$ | ND |
| FBE5-C8 | $1.7 \times 10^{-7}$ | ND | ND |
| FBE5-D9 | $1.31 \times 10^{-9}$ | $4.48 \times 10^{-9}$ | $2.68 \times 10^{-9}$ |
| FBE5-D10 | $1.97 \times 10^{-9}$ | $1.57 \times 10^{-9}$ | $3.65 \times 10^{-9}$ |
| FBE5-E5 | ND | ND | $4.34 \times 10^{-7}$ |
| FBE5-F9 | $6.01 \times 10^{-9}$ | $2.15 \times 10^{-8}$ | $7.97 \times 10^{-9}$ |
| FBE5-F11 | $2.19 \times 10^{-10}$ | $4.83 \times 10^{-10}$ | $3.96 \times 10^{-10}$ |

FIG. 21

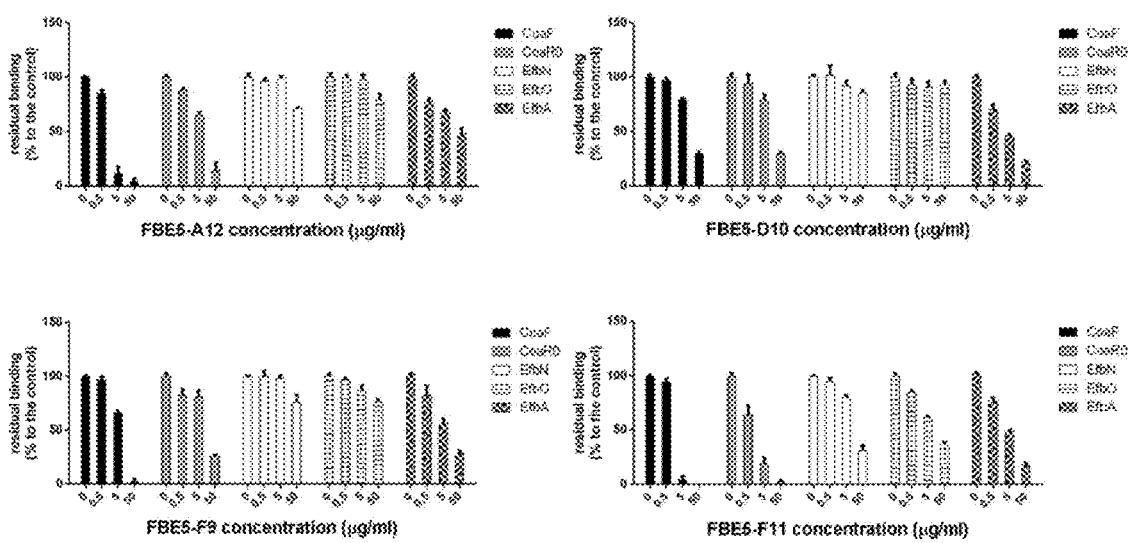

FIG. 22

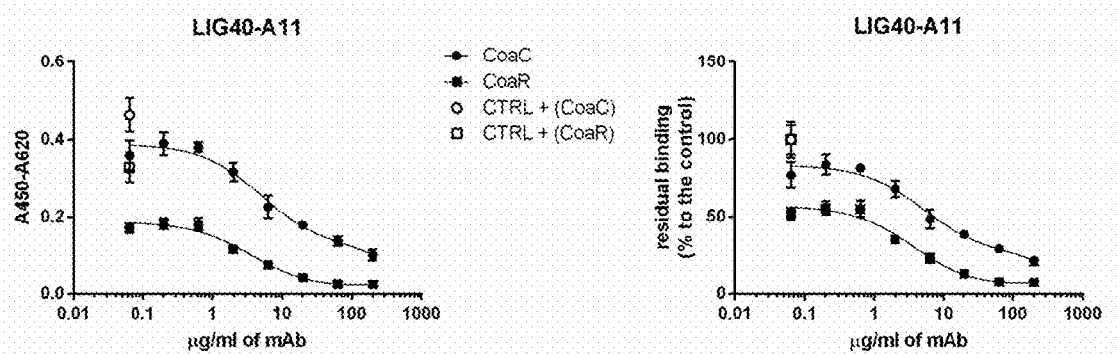
FIG. 25
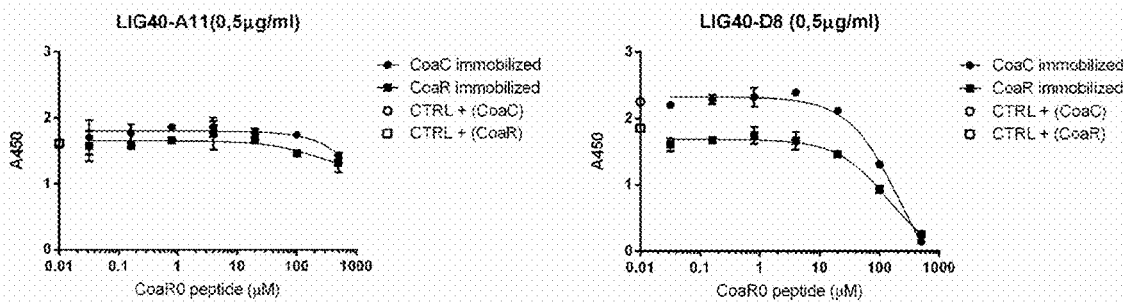
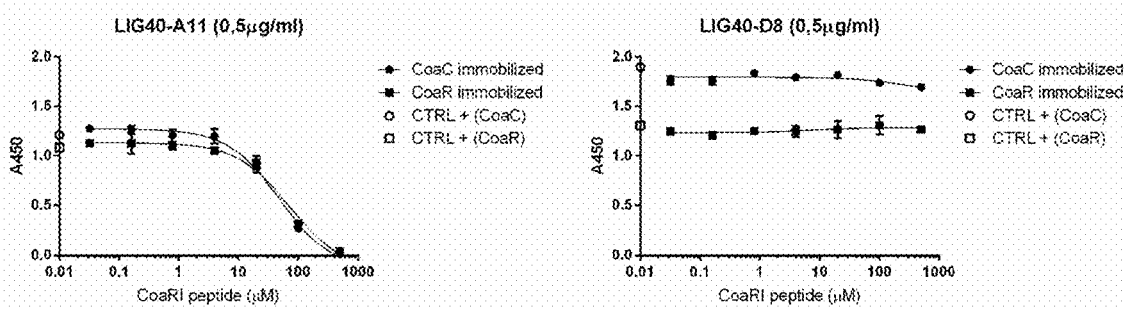
FIG. 26

| ANTIBODY | $K_d$ app (M) for CoaC | $K_d$ app (M) for CoaR | $K_d$ app (M) for CoaF | $K_d$ app (M) for CoaR0 |
|---|---|---|---|---|
| LIG40-A11 | $1.33 \times 10^{-10}$ | $7.05 \times 10^{-11}$ | ND | ND |
| LIG40-D8 | $9.39 \times 10^{-11}$ | $8.62 \times 10^{-11}$ | $1.12 \times 10^{-10}$ | $2.52 \times 10^{-9}$ |

FIG. 27

COMPOSITIONS AND USE OF A FIBRINOGEN BINDING MOTIF PRESENT IN EFB AND COA FOR THERAPEUTICS AND VACCINES AGAINST *STAPHYLOCOCCUS AUREUS*

CROSS-REFERENCE TO RELATED APPLICATIONS

The present application is a Continuation-in-Part of U.S. 371 patent application Ser. No. 15/029,896, filed Apr. 15, 2016, now abandoned, which is a National Stage of International Application No. PCT/US2014/060772, filed Oct. 15, 2014, which claims the benefit of U.S. Provisional Application No. 61/891,233, filed Oct. 15, 2013. The contents of each of which are incorporated by reference in their entirety.

STATEMENT OF FEDERALLY FUNDED RESEARCH

Not applicable.

REFERENCE TO A SEQUENCE LISTING

The present application includes a Sequence Listing which has been submitted in ASCII format via EFS-Web and is herby incorporated by reference in its entirety. Said ASCII copy, created on Jun. 11, 2021 is named TAMU1055CIP_SL_TXT_061121 and is 106 KB in size.

TECHNICAL FIELD OF THE INVENTION

The present invention relates generally to compositions and methods for preventing and treating human and animal diseases including, but not limited to, pathogens.

BACKGROUND OF THE INVENTION

Without limiting the scope of the invention, its background is described in connection with compositions and methods of treating infection by pathogens. Pathogens present serious health concerns for all animals, including humans, farm livestock, and household pets. These health threats are exacerbated by the rise of strains that are resistant to antibiotic treatment. *Staphylococcus aureus* is a leading cause of severe bacterial infections in both hospital and community settings. Due to its increasing resistance to antibiotics, development of additional therapeutic strategies like vaccination is required to control this pathogen. Vaccination attempts against *S. aureus* have not been successful so far and an important reason may be the pathogen's elaborate repertoire of molecules that dampen the immune response. These evasion molecules not only suppress natural immunity but also hamper the current attempts to create effective vaccines.

SUMMARY OF THE INVENTION

In one embodiment, the present includes an antibody or antigen binding fragment thereof that specifically binds an extracellular fibrinogen binding protein, wherein the antibody or antigen binding fragment thereof comprises: (a) a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165; and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222. In one aspect, antibody is a full-length antibody. In another aspect, antibody or antigen binding fragment thereof is a humanized antibody. In another aspect, the antigen binding fragment comprises an Fab, a Fab', a F(ab')$_2$, a single chain Fv (scFv), a disulfide linked Fv, an IgG-CH$_2$, a F(ab')$_3$, a tetrabody, a triabody, a diabody, a (scFv)$_2$, or a scFv-Fc. In another aspect, the extracellular fibrinogen binding protein is selected from Efb, Coa or both. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In another aspect, the variable heavy chain and the variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130. In another aspect, antibody or antigen binding fragment thereof further comprises a collagen-like domain, a globular domain, or both. In another aspect, the antibody or antigen binding fragment thereof further comprises a label selected from the group consisting of: a radiolabel, a fluorophore, a chromophore, an imaging agent and a metal ion, wherein the labeled antibody is a diagnostic reagent. In another aspect, the antibody or antigen binding fragment thereof further comprises a therapeutic agent selected from an analgesic, an anti-histamine, an anti-inflammatory agent, an antibiotic, a chemotherapeutic, an immunosuppressant, a cytokine, an anti-proliferative, an antiemetic, or a cytotoxin.

In another embodiment, the present includes a method of making the antibody or antigen binding fragment thereof comprising: (a) culturing a cell expressing said antibody or antigen binding fragment thereof, wherein the antibody or antigen binding fragment thereof comprises: a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165); and a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; and (b) isolating the antibody or antigen binding fragment thereof from the cultured cell, wherein the cell is a eukaryotic cell. In one aspect, the variable heavy chain and the variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present includes an immunoconjugate having the formula (A)-(L)-(C), wherein: (A) is the antibody or antigen binding fragment of claim 1; (L) is a linker; and (C) is a cytotoxic agent; wherein the linker (L) links (A) to (C) wherein the antibody or antigen binding fragment thereof comprises: a heavy chain CDR1 comprising the amino acid sequence selected from SEQ ID NOS: 131-134; a heavy chain CDR2 comprising the amino acid sequences selected from SEQ ID NOS:135-138; and a heavy chain CDR3 comprising the amino acid sequences selected from SEQ ID NOS:139-165); and a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222. In one aspect, the linker is selected from the group consisting of a cleavable linker, a non-cleavable linker, a hydrophilic linker, and a dicarboxylic acid-based linker. In another aspect, the linker is selected from the group consisting: N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol] ester (NHS-PEG4-maleimide). In another aspect, the immunoconjugate further comprises a therapeutic agent selected from an analgesic, an anti-histamine, an anti-inflammatory agent, an antibiotic, a chemotherapeutic, an immunosuppressant, a cytokine, an anti-proliferative, an antiemetic, or a cytotoxin. In another aspect, the immunoconjugate comprises: 2-6 (C), 3-4 (C), or has an average of about 3 to about 4 (C) per (A) or an average of about 3.5+/−0.5 (C) per (A). In another aspect, the e immunoconjugate further comprises a pharmaceutically acceptable carrier.

In another embodiment, the present includes a pharmaceutical composition comprising an antibody or antigen binding fragment thereof that specifically binds an extracellular fibrinogen binding protein, wherein the antibody or antigen binding fragment thereof comprises: (a) a heavy chain CDR1 comprising the amino acid sequence selected from SEQ ID NOS:131-134; a heavy chain CDR2 comprising the amino acid sequences selected from SEQ ID NOS: 135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; and a pharmaceutically acceptable carrier. In one aspect, the variable heavy chain and the variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present includes a pharmaceutical composition for use in the treatment of an infection comprises: a pharmacologically effective amount of a modified extracellular fibrinogen binding protein in a pharmaceutically acceptable excipient, wherein the modified extracellular fibrinogen binding protein comprises at least a portion of a N-terminus fibrinogen binding region, at least a portion of a C-terminus complement protein binding region, or both, wherein the modified extracellular fibrinogen binding protein results in inhibiting the fibrinogen binding, C3 binding, the surface-bound complement protein, an antibody or combination thereof; or a pharmacologically effective amount of a monoclonal and/or polyclonal antibody or antigen-binding fragment thereof that can specifically bind to a portion of a extracellular fibrinogen binding protein comprising a heavy and light chain variable regions that bind at least a portion of a N-terminus fibrinogen binding region of a extracellular fibrinogen binding protein, at least a portion of a C-terminus complement protein binding region of a extracellular fibrinogen binding protein, or both and results in the inhibition of fibrinogen binding, of complement protein binding, inhibition of the shielding of the staphylococcus bacterium from recognition by a phagocytic receptor or a combination thereof. In another aspect, the at least a portion of a N-terminus fibrinogen binding region is selected from SEQ ID NO: 3-61, preferably SEQ ID NO: 3-30 or SEQ ID NO: 35-61. In another aspect, the at least a portion of a N-terminus fibrinogen binding region is selected from SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40, 41, 42, 43, 44, 45, 46, 47, 48, 49, 50, 51, 52, 53, 54, 55, 56, 57, 58, 59, 60, and 61. In another aspect, the fibrinogen binding protein is Efb, Coa or both. In another aspect, the composition further comprises an antigen selected from SpA, SpA variant, Emp, EsxA, EsxB, EsaC, Eap, EsaB, Coa, vWbp, vWh, Ma, SdrC, SdrD, SdrE, IsdA, IsdB, IsdC, ClfA, ClfB, SasF, Sta006, Sta011, Hla, and EsxA-EsxB.

In another embodiment, the present includes a method for making a monoclonal antibody comprising the steps of: providing an effective amount of a composition comprising a modified extracellular fibrinogen binding protein having a N-terminus modified fibrinogen binding protein that does not bind fibrinogen, a C-terminus modified complement binding protein that does not bind a complement protein or both; producing an antibody pool of the modified extracellular fibrinogen binding protein, the C-terminus modified complement binding protein, or both; screening the antibody pool to detect active antibodies; wherein the active antibodies inhibit the fibrinogen binding to extracellular fibrinogen binding protein, wherein the antibody or antigen binding fragment thereof comprises: a heavy chain CDR1 comprising the amino acid sequence selected from SEQ ID NOS: 131-134; a heavy chain CDR2 comprising the amino acid sequences selected from SEQ ID NOS:135-138; and a heavy chain CDR3 comprising the amino acid sequences selected from SEQ ID NOS:139-165); and a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; separating the active antibodies; and adding the active antibodies to a pharmaceutically acceptable carrier.

In another embodiment, the present includes a method for making a vaccine comprising the steps of: providing an effective amount of a composition comprising a modified extracellular fibrinogen binding protein having a N-terminus modified fibrinogen binding protein that does not bind fibrinogen, a C-terminus modified complement binding protein that does not bind a complement protein or both and further comprising an antigen selected from SpA, SpA variant, Emp, EsxA, EsxB, EsaC, Eap, EsaB, Coa, vWbp, vWh, Hla, SdrC, SdrD, SdrE, IsdA, IsdB, IsdC, ClfA, ClfB, SasF, Sta006, Sta011, Hla, and EsxA-EsxB.

In another embodiment, the present includes a method of treating of a *Staphylococcus* bacterium infection comprising: providing a pharmacologically effective amount of a monoclonal and/or polyclonal antibody or antigen-binding fragment thereof that can specifically bind to a portion of a extracellular fibrinogen binding protein comprising antibody or antigen binding fragment thereof that specifically binds an extracellular fibrinogen binding protein, wherein the antibody or antigen binding fragment thereof comprises: a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165); and a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222, that inhibits fibrinogen binding, complement protein binding, inhibition of the shielding of the *Staphylococcus* bacterium from recognition by a phagocytic receptor, or a combination thereof. In one aspect, the variable heavy chain and the variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

The present invention provides vaccine comprising: (a) a pharmacologically effective amount of a vaccine in a pharmaceutically acceptable excipient, comprising a modified extracellular fibrinogen binding protein comprising at least a portion of a modified N-terminus fibrinogen binding region, at least a portion of a modified C-terminus complement protein binding region, or both, wherein the modified extracellular fibrinogen binding protein results in inhibiting the fibrinogen binding, C3 binding, or both; (b) a pharmacologically effective amount of a vaccine in a pharmaceutically acceptable excipient, comprising a modified extracellular fibrinogen binding protein comprising at least a portion of a modified N-terminus fibrinogen binding region, at least a portion of a modified C-terminus complement protein binding region, or both, wherein the modified extracellular fibrinogen binding protein does not shield the surface-bound complement protein, an antibody or both from recognition by a phagocytic receptor; or (c) a pharmacologically effective amount of a vaccine in a pharmaceutically acceptable excipient, comprising a modified extracellular fibrinogen binding protein comprising at least a portion of a modified N-terminus fibrinogen binding region, at least a portion of a modified C-terminus complement protein binding region, or both, wherein the modified extracellular fibrinogen binding protein does not shield the staphylococcus bacterium from recognition by a phagocytic receptor.

The present invention provides a chimeric molecule of an extracellular fibrinogen binding protein (Efb) comprising: a N-terminus fibrinogen binding region that binds a fibrinogen; and a C-terminus complement protein binding region that binds a complement protein, wherein the chimeric molecule can modulate complement activity, modulate antibody binding, modulate recognition by a phagocytic receptor or a combination thereof.

The present invention provides a monoclonal and/or polyclonal antibody or antigen-binding fragment thereof that can specifically bind to a portion of a extracellular fibrinogen binding protein comprising a heavy and light chain variable regions that bind at least a portion of a N-terminus fibrinogen binding region of a extracellular fibrinogen binding protein, at least a portion of a C-terminus complement protein binding region of a extracellular fibrinogen binding protein, or both and results in the inhibition of fibrinogen binding, of complement protein binding, inhibition of the shielding of the staphylococcus bacterium from recognition by a phagocytic receptor or a combination thereof.

The present invention provides a pharmaceutical composition comprising a pharmacologically effective amount of a modified extracellular fibrinogen binding protein in a pharmaceutically acceptable excipient, wherein the modified extracellular fibrinogen binding protein comprises at least a portion of a N-terminus fibrinogen binding region, at least a portion of a C-terminus complement protein binding region, or both, wherein the modified extracellular fibrinogen binding protein results in inhibiting the fibrinogen binding, C3 binding, the surface-bound complement protein, an antibody or combination thereof.

The present invention provides a pharmaceutical composition comprising a monoclonal and/or polyclonal antibody or antigen-binding fragment thereof that can specifically bind to a portion of a extracellular fibrinogen binding protein comprising a heavy and light chain variable regions that bind at least a portion of a N-terminus fibrinogen binding region of a extracellular fibrinogen binding protein, at least a portion of a C-terminus complement protein binding region of a extracellular fibrinogen binding protein, or both and results in the inhibition of fibrinogen binding, of complement protein binding, inhibition of the shielding of the staphylococcus bacterium from recognition by a phagocytic receptor or a combination thereof.

The present invention provides a pharmaceutical composition for use in the treatment of an infection comprising (a) a pharmacologically effective amount of a modified extracellular fibrinogen binding protein in a pharmaceutically acceptable excipient, wherein the modified extracellular fibrinogen binding protein comprises at least a portion of a N-terminus fibrinogen binding region, at least a portion of a C-terminus complement protein binding region, or both, wherein the modified extracellular fibrinogen binding protein results in inhibiting the fibrinogen binding, C3 binding, the surface-bound complement protein, an antibody or combination thereof, or (b) a pharmacologically effective amount of a monoclonal and/or polyclonal antibody or antigen-binding fragment thereof that can specifically bind to a portion of a extracellular fibrinogen binding protein comprising a heavy and light chain variable regions that bind at least a portion of a N-terminus fibrinogen binding region of a extracellular fibrinogen binding protein, at least a portion of a C-terminus complement protein binding region of a extracellular fibrinogen binding protein, or both and results in the inhibition of fibrinogen binding, of complement protein binding, inhibition of the shielding of the staphylococcus bacterium from recognition by a phagocytic receptor or a combination thereof.

In another aspect, at least a portion of a N-terminus fibrinogen binding region may be selected from SEQ ID NO: 3-61, preferably SEQ ID NO: 3-30 or SEQ ID NO: 35-61. In one aspect, at least a portion of a N-terminus fibrinogen binding region may be selected from SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40, 41, 42, 43, 44, 45, 46, 47, 48, 49, 50, 51, 52, 53, 54, 55, 56, 57, 58, 59, 60, and 61. The fibrinogen binding protein may be Efb, Coa or both. The composition may further include an antigen selected from SpA, SpA variant, Emp, EsxA, EsxB, EsaC, Eap, EsaB, Coa, vWbp, vWh, Hla, SdrC, SdrD, SdrE, IsdA, IsdB, IsdC, ClfA, ClfB, SasF Sta006, Sta011, Hla and EsxA-EsxB.

The present invention provides a pharmaceutical composition for the targeted delivery of an active agent comprising a pharmacologically effective amount of a modified extracellular fibrinogen binding protein connected to a collagen-like domain, a globular domain or both and disposed in a pharmaceutically acceptable carrier, wherein the modified extracellular fibrinogen binding protein comprises a N-terminus fibrinogen binding region that binds a fibrinogen delivering the collagen-like domain, a globular domain or both to the fibrinogen. In another aspect, at least a portion of a N-terminus fibrinogen binding region may be SEQ ID NO: 2 or SEQ ID NO: 34. The collagen-like domain, a globular domain or both may form a hydrogel. The composition may further include an antigen selected from SpA, SpA variant, Emp, EsxA, EsxB, EsaC, Eap, EsaB, Coa, vWbp, vWh, Hla, SdrC, SdrD, SdrE, IsdA, IsdB, IsdC, ClfA, ClfB, SasF Sta006, Sta011, Hla and EsxA-EsxB.

The present invention provides a method for making a monoclonal antibody comprising the steps of: providing an effective amount of a composition comprising a modified extracellular fibrinogen binding protein having a N-terminus modified fibrinogen binding protein that does not bind fibrinogen, a C-terminus modified complement binding protein that does not bind a complement protein or both; producing an antibody pool of the modified extracellular fibrinogen binding protein, the C-terminus modified complement binding protein, or both; screening the antibody pool to detect active antibodies; wherein the active antibodies inhibit the fibrinogen binding to extracellular fibrinogen binding protein; separating the active antibodies; and adding the active antibodies to a pharmaceutically acceptable carrier.

The present invention provides a method for making a vaccine comprising the steps of: providing an effective amount of a composition comprising a modified extracellular fibrinogen binding protein having a N-terminus modified fibrinogen binding protein that does not bind fibrinogen, a C-terminus modified complement binding protein that does not bind a complement protein or both and further comprising an antigen selected from SpA, SpA variant, Emp, EsxA, EsxB, EsaC, Eap, EsaB, Coa, vWbp, vWh, Ha, SdrC, SdrD, SdrE, IsdA, IsdB, IsdC, ClfA, ClfB, SasF Sta006, Sta011, Hla and EsxA-EsxB. The N-terminus modified fibrinogen binding protein may have 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9, or 99.99% homology to SEQ ID NO: 2; SEQ ID NO: 34; or both. In another aspect, at least a portion of a N-terminus fibrinogen binding region is selected from SEQ ID NO: 3-30; from SEQ ID NO: 35-61; or both. In another aspect, at least a portion of a N-terminus modified fibrinogen binding protein is selected from SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, and 30 or from SEQ ID NO: 35, 36, 37, 38, 39, 40, 41, 42, 43, 44, 45, 46, 47, 48, 49, 50, 51, 52, 53, 54, 55, 56, 57, 58, 59, 60, 61.

The present disclosure provides a method of vaccinating a host against staphylococcus bacterium by administering to a subject a pharmacologically effective amount of a vaccine in a pharmaceutically acceptable excipient, comprising a modified extracellular fibrinogen binding protein comprising at least a portion of a N-terminus region, at least a portion of a C-terminus region, or both, wherein the modified extracellular fibrinogen binding protein results in inhibiting the fibrinogen binding, C3 binding, or both or administering to a subject a pharmacologically effective amount of a vaccine in a pharmaceutically acceptable excipient, comprising a modified extracellular fibrinogen binding protein comprising at least a portion of a N-terminus region, at least a portion of a C-terminus region, or both, wherein the modified extracellular fibrinogen binding protein results in inhibiting the surface-bound complement protein, an antibody or both from shielding the staphylococcus bacterium from recognition by a phagocytic receptor.

The present disclosure provides a vaccine having a pharmacologically effective amount of a vaccine in a pharmaceutically acceptable excipient, comprising a modified extracellular fibrinogen binding protein comprising at least a portion of a N-terminus fibrinogen binding region, at least a portion of a C-terminus complement protein binding region, or both, wherein the modified extracellular fibrinogen binding protein results in inhibiting the fibrinogen binding, C3 binding, or both or having a pharmacologically effective amount of a vaccine in a pharmaceutically acceptable excipient, comprising a modified extracellular fibrinogen binding protein comprising at least a portion of a N-terminus fibrinogen binding region, at least a portion of a C-terminus complement protein binding region, or both, wherein the modified extracellular fibrinogen binding protein results in inhibiting the surface-bound complement protein, an antibody or both from shielding the staphylococcus bacterium from recognition by a phagocytic receptor.

The present disclosure also provides a monoclonal antibody or antigen-binding fragment thereof that can specifically bind to a portion of a extracellular fibrinogen binding protein comprising heavy and light chain variable regions that bind at least a portion of a N-terminus region of a extracellular fibrinogen binding protein that binds a fibrinogen, at least a portion of a C-terminus region of a extracellular fibrinogen binding protein that binds a complement protein, or both and results in the inhibition of the shielding of the staphylococcus bacterium from recognition by a phagocytic receptor.

One embodiment of the present disclosure provides a method for eliciting an immune response against a staphylococcus bacterium in a subject by identifying a subject having a staphylococcus bacterium; providing to the subject an effective amount of a composition comprising a modified extracellular fibrinogen binding protein (Efb) having a N-terminus binds that binds fibrinogen and a C-terminus binds a complement protein, wherein the Efb does not shield a surface-bound complement protein, an antibody or both from recognition by a phagocytic receptor.

Another embodiment of the present disclosure provides a vaccine made by combining a pharmaceutically acceptable excipient and an effective amount of a composition comprising a modified extracellular fibrinogen binding protein (Efb) having a N-terminus binds that binds fibrinogen and a C-terminus binds a complement protein, wherein the Efb does not shield a surface-bound complement protein, an antibody or both from recognition by a phagocytic receptor.

Another embodiment of the present disclosure provides a chimeric molecule of a extracellular fibrinogen binding protein (Efb) having a N-terminus that binds a fibrinogen; and a C-terminus that binds a complement protein, wherein the chimeric molecule can modulate complement activity, modulate antibody binding, modulate recognition by a phagocytic receptor or a combination thereof. The chimeric molecule may be capable of inhibiting or enhancing complement binding, antibody binding, recognition by a phagocytic receptor or a combination thereof.

Fibrinogen (Fg) is a plasma dimeric glycoprotein that is best known for its role in the blood coagulation cascade where thrombin proteolytically converts Fg to fibrin which then spontaneous assembles into the core of the clot. Coagulase (Coa) is a secreted staphylococcal protein and is a virulence determinant contributing to pathogenesis of staphylococcal diseases. Coa was named for its ability to support the conversion of Fg to insoluble fibrin. This activity involves Coa capturing and activating prothrombin in a non-proteolytic manner subsequently allowing the cleavage of Fg to fibrin by the activated protease. Coa also binds Fg directly independent of prothrombin. However, the molecular details underlying the Coa-Fg interaction remain elusive. The instant disclosure shows that the Fg binding activity of Coa is functionally related to that of staphylococcal Extracellular fibrinogen binding protein (Efb). In the competition ELISA assay, Coa and Efb compete with each other in binding to Fg suggesting these two staphylococcal proteins harbor similar Fg motif and are likely bind to the similar site(s) in Fg. Biochemical analyses allowed us to identify the critical residues for Fg binding in Efb and showed that the core of these residues are conserved in Fg binding motifs in Coa. This motif locates to an intrinsically disordered section of the protein and is unusually long covering 25-27 residues. Competition ELISA and isothermal titration calorimetry analyses demonstrate that Coa from Newman strain contains multiple Fg binding sites in which one locates in residues 474-505 and the others are in 5 tandem repeats which immediately follow the first binding site (residues 474-505). Binding of the Efb/Coa motif to Fg likely induces a conformational change in the plasma protein which might be the bases for the proteins ability to induce the formation of a Fg containing barrier around staphylococci that protects the bacteria from clearance by phagocytes.

DESCRIPTION OF THE DRAWINGS

For a more complete understanding of the features and advantages of the present invention, reference is now made to the detailed description of the invention along with the accompanying figures and in which:

FIGS. 1A-1F show the full-length Efb inhibits phagocytosis of S. aureus in human plasma.

FIG. 2A shows the domain organization of Efb, and 2B and 2C show the simultaneous binding to Fg and C3 is essential for phagocytosis inhibition by Efb.

FIGS. 9A to 9D illustrate a schematic presentation of recombinant Coa fragments generated in this study. Coa is depicted in its secreted form Coa (27-636) lacking the signal peptide (1-26). FIG. 9B illustrates an ELISA assays of GST-tagged Coa fragments binding to immobilized Fg, Coa (Coa 27-636); Coa-N(Coa 27-310); Coa-C(Coa 311-636); Coa-R (Coa 506-636); Coa-F (Coa 311-505). FIG. 9C is a table that shows the protein concentration at which the reaction rate is half of Vmax (Km) and the goodness of fit (R2).

FIG. 9D illustrates the effect of peptide Efb-O on inhibition of recombinant Coa (rCoa) binding to Fg. Increasing concentration of Efb-O were incubated with 4 nM GST-tagged Coa proteins in Fg-coated microtiter wells. Control, BSA.

FIG. 10A is a table of the Efb-O variant peptides were synthesized where each residue in the sequence is individually replaced with Ala (or Ser when the native a.a. is Ala). FIG. 10A includes SEQ ID NOS:1-30. FIG. 10 includes SEQ ID NO:2-30 Wells were coated with 0.25 µg/well Fg. Peptides (2 µM) were mixed with rEfb-O proteins (5 nM) and incubated in the Fg wells for 1 hour.

FIG. 11A is an image of a ClustalW alignment of amino acid sequence from Efb-O (Efb 68-98) and Coa from Newman strain (col-Newman). FIG. 11A includes SEQ ID NOS:62, 223, 224. FIGS. 11B and 11C show a comparison of amino acid sequence of Efb-O with Coa 474-505 (FIG. 11B) and Coa 506-532 (FIG. 11C). FIG. 11B includes SEQ ID NOS. 2 and 32. FIG. 11C includes SEQ ID NOS:2 and 33.

FIG. 12A is a panel of Coa-RI variant peptides were synthesized where each residue in the sequence is individually replaced with Ala (or Ser when the native a.a. is Ala). FIG. 12A includes SEQ ID NOS: 34-61. FIG. 12B includes SEQ ID NO: 34-61. Labels -1, -2, -3, -4, -5, -6, -7, -8, -9, -10, -11, -12, -13, -14, -15, -16, -17, -18, -19, -20, -21, -22, -23, -24, -25, -26, -27 refer to Coa-RI-1, Coa-RI-2, Coa-RI-3, Coa-RI-4, Coa-RI-5, Coa-RI-6, Coa-RI-7, Coa-RI-8, Coa-RI-9, Coa-RI-10, Coa-RI-11, Coa-RI-12, Coa-RI-13, Coa-RI-14, Coa-RI-15, Coa-RI-16, Coa-RI-17, Coa-RI-18, Coa-RI-19, Coa-RI-20, Coa-RI-21, Coa-RI-22, Coa-RI-23, Coa-RI-24, Coa-RI-25, Coa-RI-26, Coa-RI-27, respectively. Wells were coated with 0.25 µg/well Fg. FIG. 12C is a comparison of amino acid sequence of Efb-O with Coa-RI. FIG. 12C includes SEQ ID NOS:1 and 34. FIG. 12D is a Fg-binding register of tandem repeats in Coa. Bold letters denote the residues that are important for Fg binding. FIG. 12D includes SEQ ID NOS:63 and 225-229.

FIG. 13A is a schematic presentation of Coa R peptides. FIG. 13A includes SEQ ID NOS:34, 64, 65, 66-70. FIG. 13B is a plot of the effect of Coa peptides on inhibition of rCoa-C binding to fibrinogen.

FIG. 16A is a Schematic representation of DC2-Fg with fibrinogen (Fg) binding motif Efb-O. FIG. 16B is an image of a circular dichroism (CD) spectra of DC2 and DC2-Fg. Peak at 220 nm is indicative of triple helix. FIG. 16C is plot of the integrin α1 and α2 subunit expressing C2C12 cell adhesion to DC1 (no integrin binding site), DC2 (binding site for integrins α1 and α2), DC2-Fg (DC2 with fibrinogen binding site), and collagen (multiple binding sites for integrins α1 and α2). FIG. 16D is a graph showing fibrinogen binding to DC2, DC2-Fg, and Efb, as determined by solid phase binding assay.

FIG. 19 is a table that shows the apparent $K_d$ of anti-CoaC mAbs to different truncated recombinant Coa proteins determined through $EC_{50}$ calculation in ELISA. Apparent affinity values were generated through analysis of the half maximum binding in ELISA, using GRAPHPAD PRISM® Version 6.01. Apparent $K_d$ values in the range of $10^{-9}$-$10^{-10}$ M were obtained for most antibodies against all three Coa fragments tested (Coa-$C_{311-636}$, Coa-$F_{311-505}$. Coa-$R0_{474-505}$). The antibody FBE5-F11 has the highest affinity to all the three proteins tested and FBE5-C8, conversely was the weakest binder to the three fragments of Coa tested.

FIG. 21 is a table with the apparent $K_d$ of anti-CoaC mAbs to Efb fragments determined through $EC_{50}$ calculation in ELISA. Apparent affinity values were generated through analysis of the half maximum binding in ELISA, using GRAPHPAD PRISM® Version 6.01. In most cases, apparent $K_d$ values in the range of $10^{-8}$-$10^{-9}$ M were obtained for antibodies against all three Efb fragments tested (namely Efb-$N_{30-105}$, Efb-$A_{30-67}$ and Efb-$O_{68-98}$). FBE5-F11 was the only exception, since it displayed apparent affinities in the range of $10^{-10}$ M against all three Efb fragments. Weak binders, FBE5-C1, FBE5-C8, FBE5-E5, showed very modest binding and in some cases an estimation of apparent affinities was not possible (ND, not determinable).

FIG. 22 shows the FBE 5 mAbs that efficiently inhibit binding of Coa and Efb to Fg in a dose-dependent manner. To assess the inhibitory activity of anti-Coa scFv-Fc antibodies, 0.5 µg/well of human Fg was immobilized at 4° C. overnight in 50 mM Carbonate Buffer, pH 9.6. Indicated amounts (50, 5, 0.5 µg/ml) of scFv-Fcs prepared in 2% BSA+1×TBS+0.05% TWEEN® 20 were pre-incubated for 1 hour with a constant concentration of Coa or Efb fragments also prepared in 2% BSA+1×TBS+0.05% TWEEN® 20 at room temperature, 250 rpm shaking. Specifically, Coa-F, Coa-R0, Efb-N and Efb-O were at a fixed concentration of 10 nM; whereas Efb-A was at 750 nM. Fg-binding activity of each protein alone was also checked (no mAb control—0 µg/ml). The Fg-coated plate was blocked with 2% BSA-TBST and washed with PBST. The pre-incubated mixture of Coa/Efb and anti-Coa scFv-Fc was transferred on the Fg-coated plate and incubated for 1 hour at room temperature with shaking at 250 rpm. Residual bound Coa and Efb fragments were detected with HRP-conjugated (HorseRadish Peroxidase-conjugated) α-GST-tag antibody, except for Efb-N, where an HRP-conjugated α-HIS-tag was used (see FIG. 18). HRP-tagged antibodies were diluted in 2% BSA+1×TBS+0.05% TWEEN® 20 and used at 1:10000 dilution. Antibodies were incubated for 1 hour at room temperature with shaking at 250 rpm. HRP signal was developed using SIGMAFAST™ OPD tablets using manufacturer's guidelines. Binding of Coa and Efb fragments to Fg (no mAb control) was set to 100% and residual binding to Fg of Coa and Efb fragments in the presence of different concentrations of antibodies was calculated and represented. FBE5-A12, FBE5-D10, FBE5-F9 and FBE5-F11 did show a dose dependent inhibition of all proteins tested. In particular FBE5-F11 showed a marked inhibition against all fragments of Coa and Efb. FBE5-A12, FBE5-D10 and FBE5-F9 showed a clear inhibition of CoaF, CoaRO and EfbA, being less efficient in inhibiting EfbN and EfbO.

overnight in 50 mM Carbonate Buffer, pH 9.6. A fixed concentration of mAbs (0.5 µg/ml) in 2% BSA+1×TBS+ 0.05% TWEEN® 20 was added to the wells along with indicated amounts of CoaRO and CoaRI peptides diluted in 1×TBS. Incubation for 1 hour, room temperature, 250 rpm shaking followed. Bound scFv-Fcs were detected using a polyclonal α-human IgG HRP-conjugated Ab diluted 1:10000 in 2% BSA+1×PBS+0.05% TWEEN® 20. Antibody was incubated in the 96 well plate for 1 hour at room temperature with shaking at 250 rpm. HRP signal was developed using SIGMAFAST™ OPD following manufacturer's guidelines. An irrelevant, isotype-matched scFv-Fc served as a control (FBE3-X). All FBE5 antibodies were inhibited by peptide CoaRO in a fashion dependent of the peptide concentration. Instead, peptide CoaRI was unable to affect FBE5 mAbs binding to CoaC. An irrelevant isotype-matched antibody (FBE3-X) was tested. As shown, no binding to Coa-C was detected for this latter antibody, nor did the presence of CoaRO or CoaRI peptide affect this antibody.

Figure 24:
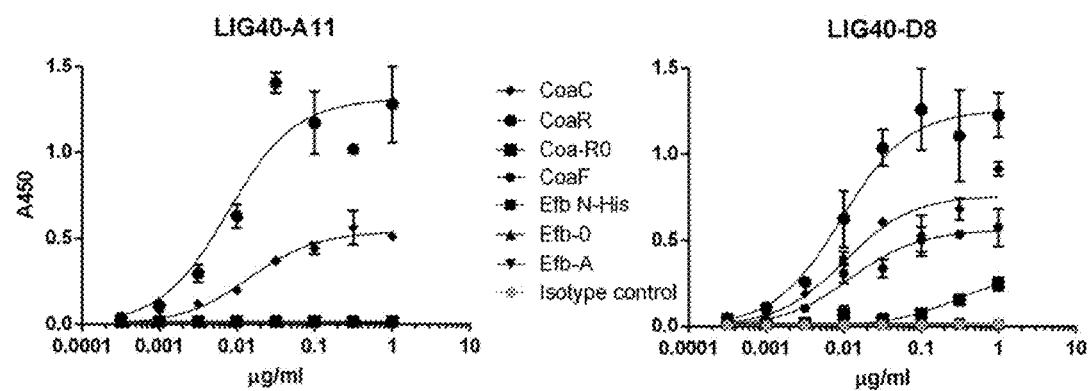

FIG. 24 shows the dose-dependent binding of LIG40 antibodies to Coa and Efb fragments. The 2 monoclonal antibodies selected against Coa-$R_{506-636}$ were titrated on different portions of the N-terminal part of Efb protein (Efb-$N_{30-105}$, Efb-$A_{30-67}$ and Efb-$O_{68-98}$), that, as reported in the parent patent, has sequence and functional homology to Coagulase. As well, binding was tested against Coa fragments, namely Coa-$C_{311-636}$. Coa-$F_{311-505}$. Coa-$RO_{474-505}$ and Coa-$R_{506-636}$. Recombinant proteins Efb-$N_{30-105}$, Efb-$A_{30-67}$, Efb-$O_{68-98}$, Coa-$C_{311-636}$, Coa-$F_{311-505}$, Coa-$RO_{474-505}$ and Coa-$R_{506-636}$ were diluted in 50 mM sodium carbonate pH 9.6 and immobilized at the concentration of 200 ng/well for 1 hour at room temperature. Immobilized proteins were probed for recognition in a solid-phase binding assay with different quantities of LIG40 antibodies after blocking and washing. After washing, varying concentrations of LIG40 scFv-Fc antibodies were diluted in 2% BSA+1×PBS+0.05% TWEEN® 20 and incubated with the immobilized proteins for 1 hour at room temperature with shaking at 250 rpm. Bound scFv-Fcs were detected using polyclonal α-human IgG HRP-conjugated Ab diluted to 1:10000 in 2% BSA+1×PBS+0.05% TWEEN® 20. HRP-conjugated Ab was incubated for 1 hour at room temperature with shaking at 250 rpm. HRP signal was developed with SIGMAFAST™ OPD using manufacturers guidelines. These 2 antibodies bound only Coa fragments in a dose dependent manner. No binding to truncated recombinant Efb proteins was observed. LIG40-A11 recognized specifically Coa-$R_{506-636}$ and, reasonably, Coa-$C_{311-636}$, even though the latter with lower apparent affinity. No binding to all other proteins has been detectable for LIG40-A11. LIG40-D8 also bound Coa-$R_{506-636}$ and Coa-$C_{311-636}$ but also binding of Coa-$F_{311-505}$ and Coa-$RO_{474-505}$ was detected to a minor extent. Both antibodies did not show binding to BSA and an irrelevant isotype-matched antibody (isotype control) did not show binding to the immobilized proteins.

FIG. 25 shows that LIG40-A11 mAb inhibits binding to Fg of Coa-$C_{311-636}$ and Coa-$R_{506-636}$ in a dose-dependent manner. To assess the inhibitory activity of LIG40-A11 antibody, 0.5 µg/well of human Fg was immobilized at 4° C. overnight in 50 mM Carbonate Buffer, pH 9.6. Indicated amounts of LIG40-A11 prepared in 2% BSA+1×TBS+ 0.05% TWEEN® 20 were pre-incubated for 1 hour with a constant concentration of CoaC or CoaR (10 nM) also prepared in prepared in 2% BSA+1×TBS+0.05% TWEEN® 20 at room temperature with shaking at 250 rpm. Fg-binding activity of each protein at 10 nM was also checked in the absence of antibody, referred as CTRL+(CoaC) and CTRL+ (CoaR) in the figure (no mAb control—CTRL+). The Fg-coated plate was blocked with 2% BSA-TBST and washed with TBST. The pre-incubated mixture of CoaC/CoaR and LIG40-A11 was transferred on the Fg-coated plate. Residual bound CoaC and CoaR were detected with HRP-conjugated α-GST-tag antibody, diluted 1:10000 in 2% BSA-1×TBS+ 0.05% TWEEN® 20, incubated for 1 hour, room temperature, 250 rpm. Binding of CoaC and CoaR to Fg in the absence of mAb (referred as CTRL+(CoaC) and CTRL+ (CoaR) in the figure) (no mAb control—CTRL+) was set to 100% and residual binding to Fg of CoaC and CoaR in the presence of different concentrations of antibodies was calculated and represented. LIG40-A11 showed a dose-dependent inhibition of CoaC and CoaR, being more potent against CoaR.

FIG. 26 shows that peptides CoaRO and CoaRI differentially inhibit LIG40 mAbs (LIG40-A11 and LIG40-D8) binding to CoaC and CoaR. To investigate if LIG40 mAbs could be inhibited by CoaRO and CoaRI peptides, CoaC and CoaR (200 ng/well) was immobilized at 4° C. overnight in 50 mM Carbonate Buffer, pH 9.6. A fixed concentration of mAbs (0.5 µg/ml) prepared in 2% BSA+1×TBS+0.05% TWEEN® 20 was added to the wells along with indicated amounts of CoaRO and CoaRI peptides prepared in 1X TBS. Incubation for 1 hour, room temperature, 250 rpm shaking followed. After washing, the levels of bound mAbs were determined using a polyclonal α-human IgG HRP-conjugated Ab diluted 1:10000 in 2% BSA+1×TBS+0.05% TWEEN® 20. Incubation lasted 1 hour at room temperature with shaking at 250 rpm. The development was performed through SIGMAFAST™ OPD tablets following manufacturer's protocol. Surprisingly, LIG40-A11 and LIG40-D8 behaved differently in the presence of the two peptides. First, to achieve appreciable inhibition high concentration of peptides needed to be used (above 100 µM). Secondly and most importantly, LIG40-A11 was inhibited only by CoaRI peptide, both when mAb binding was tested against CoaC and CoaR. In symmetrical opposite way, LIG40-D8 was only impaired in its binding activity by CoaRO peptide, suggesting that the differential role of the two repeats.

FIG. 27 is a table that shows the apparent $K_d$ of anti-Coa-$R_{506-636}$ mAbs to Coa fragments determined through $EC_{50}$ calculation in ELISA. Apparent affinity values were generated through analysis of the half maximum binding in ELISA, using GRAPHPAD PRISM® Version 6.01. For both antibodies, values in the range of $10^{-10}$-$10^{-11}$ M were obtained. LIG40-A11 showed the highest apparent affinity for CoaR ($7.05 \times 10^{-11}$ M) whereas LIG40-D8 was the one that showed the highest half-maximum binding to CoaC ($9.39 \times 10^{-11}$ M). Only LIG40-D8 showed minor binding to CoaRO and CoaF, instead for LIG40-A11 there was no detectable binding (apparent affinity not determinable, ND).

DESCRIPTION OF EMBODIMENTS

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

Upon contact with human plasma, bacteria are rapidly recognized by the complement system that labels their surface for uptake and clearance by phagocytic cells. *Staphylococcus aureus* secretes the 16 kD Extracellular fibrinogen binding protein (Efb) that binds two different plasma proteins using separate domains: the Efb N-terminus binds to fibrinogen, while the C-terminus binds complement C3. Efb blocks phagocytosis of *S. aureus* by human neutrophils. In vitro, Efb blocks phagocytosis in plasma and in human whole blood. Using a mouse peritonitis model, Efb effectively blocks phagocytosis in vivo, either as a purified protein or when produced endogenously by *S. aureus*. Mutational analysis revealed that Efb requires both its fibrinogen and complement binding residues for phagocytic escape. Using confocal and transmission electron microscopy it can be see that Efb attracts fibrinogen to the surface of complement-labeled *S. aureus* generating a 'capsule'-like shield. This thick layer of fibrinogen shields both surface-bound C3b and antibodies from recognition by phagocytic receptors. This information is critical for future vaccination attempts, since opsonizing antibodies may not function in the presence of Efb. Efb from *S. aureus* uniquely escapes phagocytosis by forming a bridge between a complement and coagulation protein.

The present disclosure describes a novel mechanism by which *S. aureus* can prevent uptake by phagocytic immune cells. Specifically, the secreted *S. aureus* protein Extracellular fibrinogen binding protein (Efb) generates a 'capsule'-like shield around the bacterial surface through a dual interaction with the plasma proteins complement C3b and fibrinogen. The Efb-dependent fibrinogen shield masks important opsonic molecules like C3b and antibodies from binding to phagocyte receptors. This information is critical for future vaccination attempts, since opsonizing antibodies may not function in the presence of this anti-phagocytic shield.

Phagocytosis by neutrophils is crucial to the host innate defense against invading bacteria since it leads to intracellular destruction of bacteria by production of oxygen radicals and proteolytic enzymes. Bacterial engulfment by neutrophils is strongly enhanced by the labeling or 'opsonization' of bacteria with plasma factors such as antibodies and complement activation products (C3b, iC3b). Complement activation takes place at the bacterial surface and is initiated by recognition molecules (C1q, Mannose Binding Lectin (MBL)) that interact with bacterial surface structures like sugars or proteins. Complement activation occurs through three different pathways (classical, lectin and alternative) that converge in the formation of C3 convertase enzymes that cleave the central complement protein C3. This cleavage step leads to massive decoration of the bacterial surface with covalently deposited C3b and iC3b molecules, which are recognized by complement receptor 1 and 3 (CR1 and CR3) on neutrophils. Complement activation proceeds by formation of C5 convertase enzymes that cleave C5 to release the potent chemoattractant C5a and C5b, which initiates formation of the membrane attack complex.

*Staphylococcus aureus* is an important human pathogen notorious for its ability to cause both community- and hospital-acquired diseases, ranging from mild skin infections to bacteremia, sepsis and endocarditis. Although Methicillin-resistant *S. aureus* (MRSA) was previously considered as an opportunistic pathogen causing hospital-acquired infections in immune-compromised patients, the emergence of the highly virulent community-associated (CA-) MRSA showed that this bacterium could also cause serious infections in otherwise healthy persons. Due to the rapid emergence of antibiotic resistance strains, alternative therapy options are now being explored. Vaccination has not been successful so far and an important reason may be the bacteria's elaborate immune evasion repertoire. Therefore, immune evasion proteins are now considered as important vaccination targets. One proposed vaccine candidate is the *S. aureus* Extracellular fibrinogen binding protein (Efb), a 16-kD secreted protein with a presumable role in disease pathogenesis, which is found in 85% of *S. aureus* strains. The secreted Efb protein consists of two functionally distinct domains: a disordered 9 kD N-terminus (Efb-N) that harbors two binding sites for fibrinogen (Fg) and a folded 7 kD C-terminus (Efb-C) that binds to the C3d domain of complement C3 (which is also present in C3b and iC3b). Although previous papers described various functions for the isolated N- and C-terminal domains of Efb, it is currently not understood why the full-length Efb protein harbors both a Fg and C3d binding site. The present disclosure shows Efb potently blocks phagocytosis of bacteria via a novel mechanism linking the complement and coagulation proteins.

Full-length Efb inhibits phagocytosis in the presence of plasma. FIG. 1A shows phagocytosis of fluorescently labeled *S. aureus* by purified human neutrophils in the presence of human serum or plasma and Efb (0.5 µM). FIG. 1B shows a histology image of human neutrophils incubated with *S. aureus* and 2.5% plasma in the presence or absence of Efb (0.5 µM). Cells were stained using Diff-Quick. FIG. 1C shows dose-dependent phagocytosis inhibition by Efb in the presence of 2.5% human plasma. $IC_{50}$ was calculated using non-linear regression analysis, $R^2=0.95$. FIGS. 1D-1F show phagocytosis in the presence of 5% human serum supplemented with either full-length human Fg (FIG. 1D), the D domain of human Fg (1 µM or 86 µg/ml) (FIG. 1E) or mouse Fg (WT or lacking the Mac-1 binding site) (FIG. 1F). A, C-F are mean f se of three independent experiments. B is a representative image. *$P<0.05$, **$P<0.005$ for Efb versus buffer (two-tailed Student's t-test).

The present disclosure provides potential role for full-length Efb in phagocytosis escape, fluorescently labeled *S. aureus* was mixed with purified human neutrophils, Efb (0.5 µM) and human serum or plasma as a source for complement and analyzed bacterial uptake by flow cytometry. In the presence of serum, Efb did not affect bacterial uptake by neutrophils (FIG. 1A). However, when human plasma as a complement source was used, Efb strongly prevented phagocytosis (FIGS. 1A and 1B) and subsequent bacterial killing by neutrophils. Phagocytosis inhibition in plasma occurred in a dose-dependent fashion with a calculated $IC_{50}$ of 0.08 µM (FIG. 1C). Since the main difference between plasma and serum lies in the presence of coagulation proteins, it was investigated whether the observed differences in phagocytosis inhibition were caused by the fact that serum lacks Fg. The supplementation of serum with physiological concentrations of Fg led to phagocytosis inhibition by Efb (FIG. 1D). Fg is a large (340 kD) dimeric protein that comprises one central E-fragment and two lateral D-fragments. Since Efb binds to the D-fragment of Fg, it was examined if supplementing serum with Fg-D would also lead to phagocytosis inhibition by Efb. Interestingly, Efb could not block phagocytosis in the presence of Fg-D (FIG. 1E) indicating that full-length Fg is required for phagocytosis inhibition by Efb. Since Fg is a ligand for CR3 (or Mac-1) on neutrophils, it was examined whether the binding of Fg to this receptor is important for the anti-phagocytic effect of Efb. Therefore, purified Fg from wild-type mice or Fgγ$^{390-396A}$ mice (ΔMac-1 Fg) mice that express a mutated form of Fg lacking the Mac-1 binding site but retaining clotting function. FIG. 1F shows that supplementation of human serum with both forms of mouse Fg led to inhibition by Efb, indicating that Fg binding to Mac-1 is not important for inhibition. In conclusion, Efb interferes with phagocytosis in a plasma environment and the presence of full-length Fg is required for this inhibition.

FIG. 2A shows a schematic overview of Efb mutants generated in this study. Efb is depicted in its secreted form (30-165) lacking the signal peptide (1-29). Bounding boxes indicate Fg- and C3-binding domains. The N-terminus of Efb (9 kD) harbors two Fg binding sites named Fg1 (residues 30-67) and Fg2 (residues 68-98). The C-terminus of Efb (7 kD) harbors the C3 binding site (residues R131 and N138). EfbΔFg1 has deletion of residues 30-45, resulting in non-functional binding Fg1; whereas EfbΔFg2 has deletion of residues 68-76, resulting in non-functional binding Fg2. In the figure, SP represents the signal peptide, N shows the N-terminus of the protein, C represents the C-terminus of the protein, the light grey box represents the His tag and the dark grey box represents the GST tag. FIG. 2B shows phagocytosis of fluorescent S. aureus by human neutrophils in the presence of 5% human plasma and Efb fragments (B) or Efb mutants (C) (all at 1 μM). B&C are mean f se of three independent experiments. **P<0.005 for Efb versus buffer (two-tailed Student's t-test).

Simultaneous binding to Fg and C3 is essential for phagocytosis inhibition by Efb. To get more insight into the mechanism of inhibition, panel of Efb mutants was constructed (FIG. 2A). FIG. 2A shows a schematic representation of domain organization of Efb protein. From the N-terminus Efb contains a signal peptide (SP), N-terminus domain that binds fibrinogen is labeled as EfbN and a C-terminus domain that binds complement protein is labeled as EfbC. The individual N or C termini of Efb could not block phagocytosis in plasma (FIG. 2B). In addition, mixing the N and C terminal fragments of Efb did not markedly affect phagocytosis, indicating that full-length Efb is required. Second, mutants of full-length Efb lacking the previously characterized binding sites for Fg and C3 were generated (FIG. 2A). Three different Fg-binding mutants were created: EfbΔFg1 lacking residues 30-45, EfbΔFg2 lacking residues 68-76 and EfbΔFg1+2 lacking both these Fg binding sites. Furthermore, EfbΔC3 were created in which the C3d-binding residues R131 and N138 were each replaced with a glutamic acid (E) (also known as Efb-RENE). Using ELISA's it can be seen that EfbΔFg1+2 could no longer bind Fg, while the single EfbΔFg1 and EfbΔFg2 mutants and EfbΔC3 still bound Fg. As expected, all mutants except EfbΔC3 to bound to C3b. Next, these mutants in the neutrophil phagocytosis assay were compared in the presence of human plasma. EfbΔFg1+2 and EfbΔC3 could no longer block phagocytosis (FIG. 2C), indicating that a simultaneous interaction with both Fg and complement C3 (products) is essential for the anti-phagocytic action of Efb. The finding that EfbΔFg1 and EfbΔFg2 were still active indicates that Efb requires only one of its two Fg binding sites to block phagocytosis.

Figure 3A:
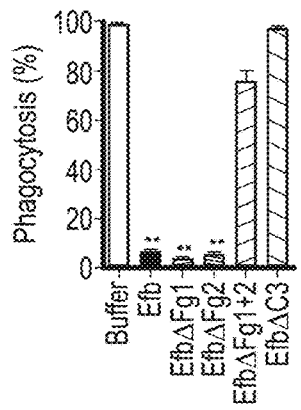
FIGS. 3A-3C show the purified Efb blocks phagocytosis ex vivo and in vivo.
Figure 3B:
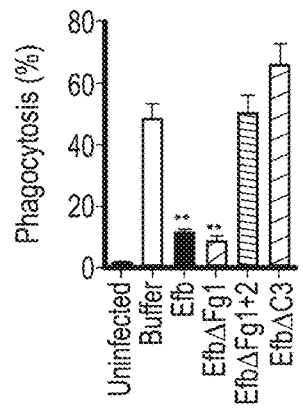
Figure 3C:
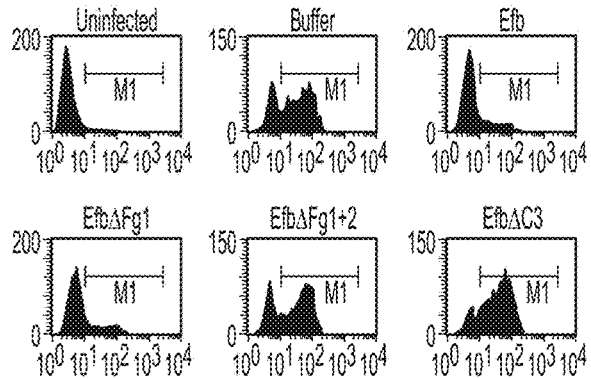

FIG. 3A shows Ex vivo phagocytosis of fluorescent S. aureus incubated with 50% human whole blood and Efb (1 μM). Neutrophils were gated based on forward and side scatter properties. FIG. 3B shows In vivo phagocytosis of fluorescent S. aureus by human neutrophils in the mouse peritoneum. Neutrophils were attracted to the peritoneal cavity using carrageenan (i.p.) and subsequently challenged with 10$^8$ heat-inactivated fluorescent S. aureus and Efb (1 μM) for 1 hour. The peritoneal lavage was collected, and neutrophil phagocytosis was analyzed by flow cytometry. Neutrophils were gated based on Gr-1 expression. The mouse studies were carried out three times. 3 mice per group were used and the cells of these 3 mice were pooled for phagocytosis analysis. FIG. 3C shows a representative histograms of FIG. 3B. A, B are mean f se of three independent experiments. *P<0.05, **P<0.005 for Efb versus buffer (two-tailed Student's-test).

Efb blocks phagocytosis ex vivo and in vivo. To study whether Efb can also block phagocytosis in a natural environment, its activity in ex vivo and in vivo was examined using phagocytosis models. In an ex vivo human whole blood model, fluorescent S. aureus was incubated with 50% human whole blood and Efb. After 25 minutes, neutrophil phagocytosis was analyzed by flow cytometry. Full-length Efb potently blocked phagocytosis by human neutrophils in whole blood (FIG. 3A) and that this inhibition depends on the interaction of Efb with both Fg and C3. Phagocytosis of S. aureus in an in vivo mouse peritonitis model was examined. To this end, mice were treated with carrageenan (i.p.) to induce neutrophil infiltration into the peritoneal cavity and subsequently challenged with 10$^8$ heat-inactivated fluorescent S. aureus in the presence or absence of Efb (1 μM). One hour later, mice were sacrificed, and the peritoneum was lavaged with sterile PBS. Neutrophils were stained and phagocytosis of fluorescent bacteria was analyzed by flow cytometry. It can be seen that Efb blocked phagocytosis in the peritoneum (FIGS. 3B and 3C). Efb mutants showed that inhibition of phagocytosis in vivo also depends on the Fg and C3 binding domains of Efb.

Figure 4A:
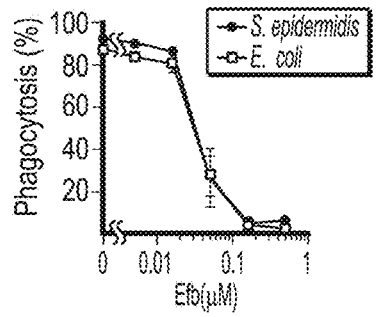
FIGS. 4A-4D show phagocytosis inhibition by Efb is independent of complement inhibition.
Figure 4B:
Figure 4C:
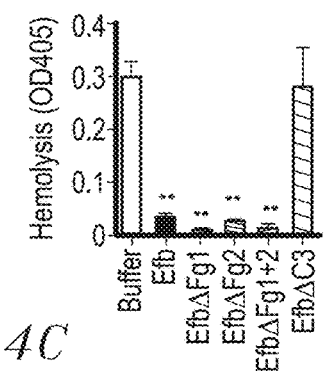
Figure 4D:
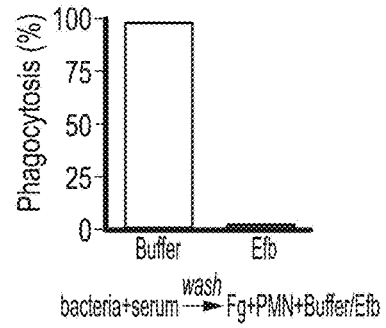

FIG. 4A shows phagocytosis of fluorescently labeled S. epidermidis and E. coli by purified human neutrophils in the presence of human plasma (5%) and Efb. FIG. 4B shows an immunoblot detecting surface-bound C3b after incubation of S. aureus with 5% human plasma in the presence of 5 mM EDTA or 0.5 μM Efb. Blot is a representative of 3 independent experiments. FIG. 4C shows alternative pathway hemolysis of rabbit erythrocytes in 5% human plasma and Efb (mutants) (1 μM). Bars are the mean t se of three independent experiments. **P<0.005 for Efb versus buffer (two-tailed Student's t-test). FIG. 4D shows phagocytosis with a washing step. Fluorescent S. aureus was first incubated with 5% serum to deposit complement. Bacteria were washed and subsequently mixed with neutrophils and Fg in the presence or absence of Efb (0.5 μM).

Phagocytosis inhibition by Efb is independent of complement inhibition. Studies shown above indicate that Efb requires an interaction with both complement and Fg to block phagocytosis. To study whether Efb also interacts with S. aureus specifically, it was analyzed whether purified Efb can block phagocytosis of other bacteria as well. Fluorescent S. epidermidis or E. coli were mixed with human plasma and phagocytosis by neutrophils was evaluated. Efb potently inhibits the uptake of these bacteria as well, indicating that Efb can block phagocytosis independently of S. aureus (FIG. 4A). The C-terminal domain of Efb is a complement inhibitor that inactivates C5 convertases to prevent cleavage of C5. Efb-C did not affect C3b labeling of bacteria in conditions where all complement pathways are active. However, since the effects of Efb on complement were performed with serum instead of plasma, it was examined whether full-length Efb might affect C3b labeling of bacteria in a plasma environment. S. aureus was incubated with human plasma and Efb and quantified surface-bound C3b using immunoblotting. As a control, EDTA was added to prevent activation of all complement routes (which are calcium and magnesium dependent). Lower amounts of C3b was not found on the bacterial surface in the presence of Efb compared to buffer (FIG. 4B), indicating that Efb does not interfere with C3b labeling in plasma. Subsequently, the inhibition of C5 convertases by Efb (mutants) in plasma using an alternative pathway hemolytic assay was examined. Rabbit erythrocytes were incubated with human plasma and C5 cleavage was measured by means of C5b-9 dependent lysis of erythrocytes. In conjunction with previous results in serum, it can be see that all Efb mutants except for EfbΔC3 inhibited C5 cleavage in plasma (FIG. 4C). Since this inhibition exclusively depends on the C-terminal domain (all Fg binding mutants of Efb could still block C5 cleavage), this proves that interference with C5 cleavage is at least not sufficient for phagocytosis inhibition by Efb. To further show that the effects of Efb on complement activation are dispensable for phagocytosis inhibition a washing step was added to the phagocytosis assay. Bacteria were first incubated with serum (in the absence of Efb) to deposit C3b. After washing away unbound serum proteins (including C5a), these pre-opsonized bacteria were incubated with Fg and neutrophils. In this assay, Efb could potently block phagocytosis (FIG. 4D). In conclusion, these results indicate that the anti-phagocytic activity of Efb is not related to its complement-inhibitory effect.

Figure 5A:
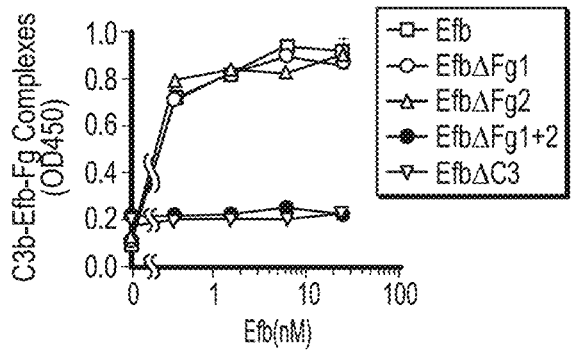
FIGS. 5A-5D show that Efb attracts Fg to the bacterial surface.
Figure 5B:
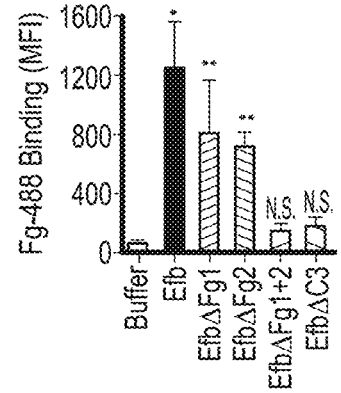
Figure 5C:
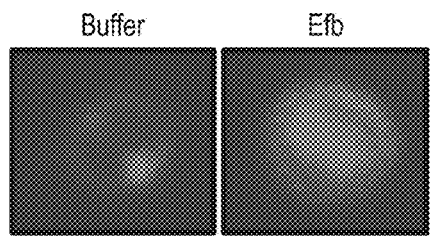
Figure 5D:
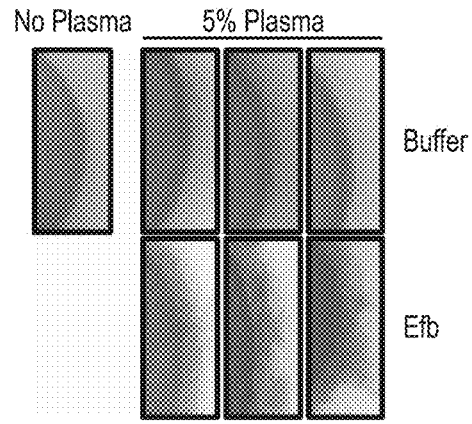

FIG. 5A shows an ELISA showing that Efb can bind Fg and C3b at the same time. C3b-coated microtiter wells were incubated with Efb (mutants) and, after washing, incubated with 50 nM Fg that was detected with a peroxidase-conjugated anti-Fg antibody (Abcam). Graph is a representative of two independent studies performed in duplicate. FIG. 5B shows binding of ALEXA FLUOR™ 488-labeled Fg (60 μg/ml) to serum-opsonized S. aureus in the presence of Efb (mutants) (0.5 μM). Graph represents mean±se of three independent experiments. *P<0.05, **P<0.005 for Efb versus buffer (two-tailed Student's t-test). N.S. is not significant. FIG. 5C shows confocal analysis of samples generated in B (representative images). FIG. 5D shows TEM pictures of S. aureus incubated with 5% human plasma in the absence or presence of Efb (0.5 μM).

Efb covers S. aureus with a shield of Fg. To determine whether Efb might bind to C3b-labeled bacteria and then attract Fg to the surface, full-length Efb binding to Fg and C3b at the same time. C3b-coated microtiter plates were incubated with Efb and, after a washing step, treated with Fg. FIG. 5A shows that Efb is able to form a complex with C3b and Fg. Also, the EfbΔFg1 and EfbΔFg2 mutants could still form Fg-C3b complexes. In contrast, complex formation was not detected for the mutants that lack either both Fg (EfbΔFg1+2) or the C3 binding domains (EfbΔC3) (FIG. 5A). Then Efb binding and attracting Fg to pre-opsonized bacteria was examined. Therefore, S. aureus was pre-opsonized with human serum to deposit complement and subsequently incubated with Efb. After washing, bacteria were incubated with ALEXA FLUOR™ 488 conjugated Fg. Using both flow cytometry and confocal microscopy it can be seen that Efb mediates Fg binding to pre-opsonized bacteria (FIGS. 5B, 5C). Consistent with the ELISA data for complex formation, no Fg binding was detected in the presence of EfbΔFg1+2 or EfbΔC3. Confocal analyses indicated that Efb covers the complete bacterial surface with Fg (FIG. 5C). Using Transmission Electron Microscopy this Fg layer created by Efb and be seen in more detail. After incubation of S. aureus with plasma and Efb, a diffuse outer layer formed around the bacteria (FIG. 5D). Altogether these studies show that Efb binds to C3b on the bacterial surface and subsequently attracts Fg forming a shield around the bacterial surface.

Figure 6A:
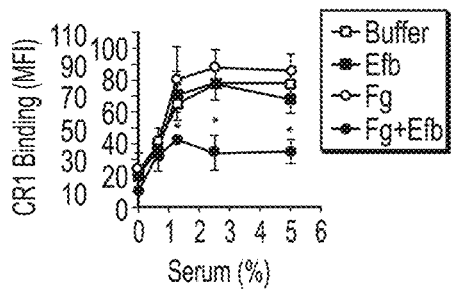
FIGS. 6A-6C show that Efb prevents recognition of opsonic C3b and IgG.
Figure 6B:
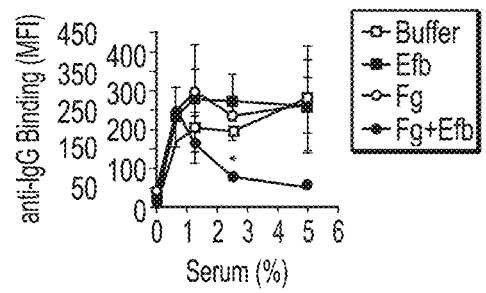
Figure 6C:
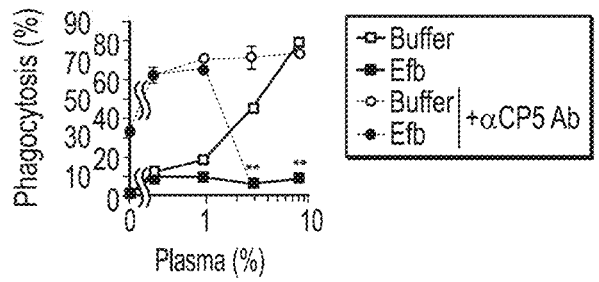

Flow cytometry assay detecting binding of soluble CR1 (FIG. 6A) or anti-IgG antibody (FIG. 6B) to pre-opsonized S. aureus in the presence of buffer, Efb (0.5 μM) and/or Fg (200 μg/ml). FIG. 6C shows Efb inhibits phagocytosis of encapsulated S. aureus by human neutrophils. FITC-labeled S. aureus strain Reynolds (high capsule CP5 expressing strain) was incubated with human plasma and/or Efb (0.5 μM) in the presence (dotted line) or absence (solid line) of polyclonal rabbit anti-CP5 antibody. All figures represent the mean f se of three separate experiments. *P<0.05, **P<0.005 for Efb+Fg versus buffer (A, B) or Efb versus buffer (for dotted lines) (two-tailed Student's t-test).

Efb blocks recognition of C3b and IgG on the surface. Since Efb covers bacteria with a shield of Fg, which would frustrate the binding of phagocytic receptors to their ligands on the bacterial surface using flow cytometry, it was first analyzed whether C3b-labeled bacteria were still recognized by CR1. Pre-opsonized S. aureus was incubated with soluble CR1 in the presence of Fg and Efb. Clearly, binding of CR1 to pre-opsonized bacteria was blocked by the presence of both Fg and Efb (FIG. 6A). Addition of Fg or Efb alone did not affect CR1 binding. Next, it was investigated whether the Fg shield specifically blocks C3b-CR1 interactions or whether it also disturbs the binding of neutrophil Fc receptors to opsonic antibodies. To analyze this, it was determined whether the Fc part of bacterium-bound IgG could still be recognized by specific antibodies and found that incubation of pre-opsonized bacteria with Efb and Fg disturbs recognition of the antibody Fc domain on the surface (FIG. 6B), suggesting that Fc receptors can no longer recognize their target. This information is crucial for future vaccine development since opsonic antibodies against S. aureus may not function when Efb hides these antibodies underneath an Fg shield. To further prove that Efb functionally blocks opsonization, phagocytosis of an encapsulated S. aureus strain in the presence or absence of anti-capsular antibodies was analyzed. The encapsulated S. aureus strain Reynolds was grown for 24 hours in Columbia agar supplemented with 2% NaCl (for optimal capsule expression) and subsequently labeled with FITC. Capsule expression after FITC-labeling was confirmed using specific antibodies. In low plasma concentrations (0-1%), it was observed that anti-capsular antibodies caused a 6-fold increase in phagocytic uptake of encapsulated S. aureus (FIG. 6C). At these plasma concentrations, Efb could not block phagocytosis. However, at higher plasma concentrations (3% and more), Efb potently impeded phagocytosis in the presence of anti-capsule antibody (FIG. 6C). These data support our idea that the Fg shield created by Efb prevents recognition of important opsonins like C3b and IgG, also in the context of a capsule-expressing strain that is targeted by specific antibodies.

Figure 7A:
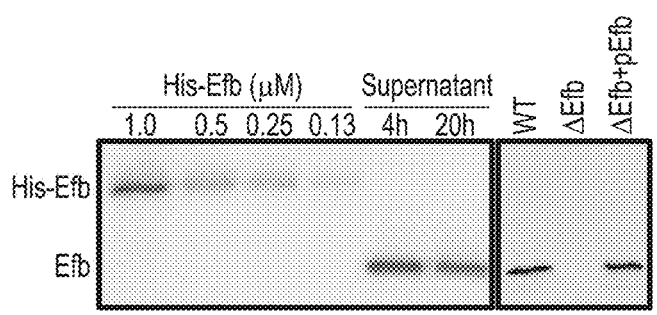
FIGS. 7A-7D show endogenously produced Efb blocks phagocytosis via complex formation.
Figure 7B:
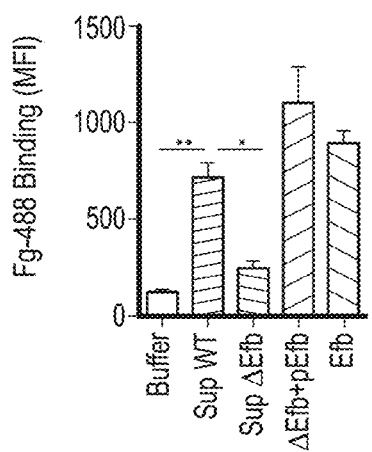
Figure 7C:
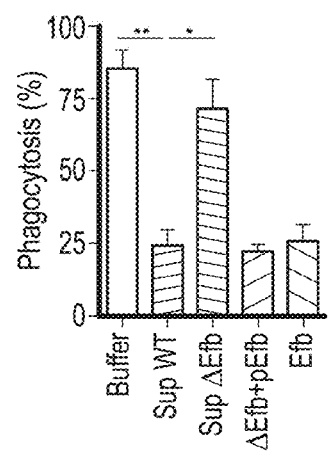
Figure 7D:
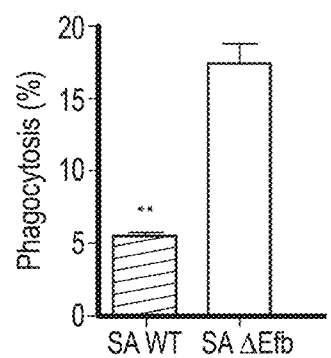

FIG. 7A left shows immunoblot detecting Efb in 4 h and 20 h culture supernatants of S. aureus Newman; fixed concentrations of His-tagged Efb were loaded as controls. FIG. 7A right shows immunoblot of 4 h culture supernatants of S. aureus Newman (WT), an isogenic Efb deletion mutant (ΔEfb) and its complemented strain (ΔEfb+pEfb). Blots were developed using polyclonal sheep anti-Efb and Peroxidase-labeled donkey anti-sheep antibodies. Blot is a representative of two independent experiments. FIG. 7B shows flow cytometry analysis of the binding of ALEXA FLUOR™ 488-labeled Fg to pre-opsonized S. aureus in the presence of 4 h culture supernatants (2-fold diluted) or purified Efb (250 nM). FIG. 7C shows in vitro phagocytosis of fluorescently labeled S. aureus by purified human neutrophils. Pre-opsonized S. aureus was first incubated with 4 h culture supernatants (2-fold diluted) or purified Efb (250 nM) and subsequently mixed with Fg and neutrophils. FIG. 7D shows in vivo phagocytosis of GFP-expressing wild-type or Efb-deficient S. aureus strains by neutrophils in the mouse peritoneal cavity. Neutrophils were attracted to the peritoneal cavity using carrageenan (i.p.) and subsequently injected with 300 µl of GFP-expressing wild-type (SA WT) or Efb-deficient (SAΔEfb) S. aureus strains during the exponential phase of growth. The peritoneal lavage was collected 1 hour thereafter and neutrophil phagocytosis was analyzed by flow cytometry. Neutrophils were gated based on Gr-1 expression. Graphs in B-D represent mean f se of three independent experiments. *P<0.05, **P<0.005 for Buffer versus WT Sup or WT (Sup) versus ΔEfb (Sup) (two-tailed Student's t-test).

Endogenous Efb blocks phagocytosis in vitro and in vivo. To study whether endogenous expression of Efb leads to impaired phagocytosis of S. aureus via complex formation, the analyses was extended with (supernatants of) an isogenic Efb-deletion mutant in S. aureus Newman. First immunoblotting was performed to semi-quantify the production levels of Efb in liquid bacterial culture supernatants. Supernatants of wild-type (WT) S. aureus Newman were subjected to Immunoblotting and developed using polyclonal anti-Efb antibodies (FIG. 7A). Efb expression in the supernatant was quantified using ImageJ software and compared with fixed concentrations of purified (His-tagged) Efb using linear regression analysis ($R^2$=0.986). Efb levels in 4 hours and 20 hours supernatants contained 1.1 µM and 0.9 µM Efb respectively. Although the Efb levels in strain Newman are suspected to be higher than in other S. aureus strains (up to 10-fold, due to a point mutation in the SaeR/S regulatory system that drives expression of immune evasion genes), the fact that these levels are >10 times higher than the calculated $IC_{50}$ needed for phagocytosis inhibition (0.08 µM, FIG. 1C), suggests that Efb concentrations required for phagocytosis inhibition can be reached in vivo. In a separate Immunoblot, the presence of Efb was checked in 4 hours supernatants of the WT, Efb-deficient (ΔEfb) and the complemented strain (ΔEfb+pEfb) confirming the lack of Efb expression in the mutant (FIG. 7A). Next these supernatants were used to study whether endogenous Efb can mediate C3b-Fg complex formation on the bacterial surface. S. aureus was first incubated with serum to deposit C3b, then mixed with bacterial supernatants and subsequently incubated with fluorescently labeled Fg. Whereas WT supernatants attracted Fg to the surface of pre-opsonized bacteria, Efb-deficient supernatants did not mediate complex formation (FIG. 7B). This phenotype was restored in the complemented strain. Then it was studied whether endogenous Efb could inhibit phagocytosis by neutrophils in vitro. Therefore, it was repeated the latter study (but using fluorescent bacteria and unlabeled Fg) and subsequently mixed the bacteria with human neutrophils. That supernatants of WT and complemented strains were found to inhibit phagocytosis, while Efb-deficient supernatants did not influence this process (FIG. 7B). To mimic bacterial phagocytosis during a natural infection, carrageenan-treated mice were injected i.p. with GFP-expressing WT S. aureus or the Efb-deficient mutant in their original broth culture and sacrificed 1 h thereafter. Mice were subjected to peritoneal lavage and the percentage of neutrophils with internalized staphylococci was determined by flow cytometry. As depicted in FIG. 7D, the Efb-deficient S. aureus strain was phagocytosed by neutrophils to a significantly higher extent than the WT strain despite of the fact that the amount of inoculated bacteria was comparable in both groups (app. $2\times10^7$). These observations demonstrate that the levels of Efb produced by S. aureus are sufficient for preventing phagocytosis in vivo.

Figure 8:
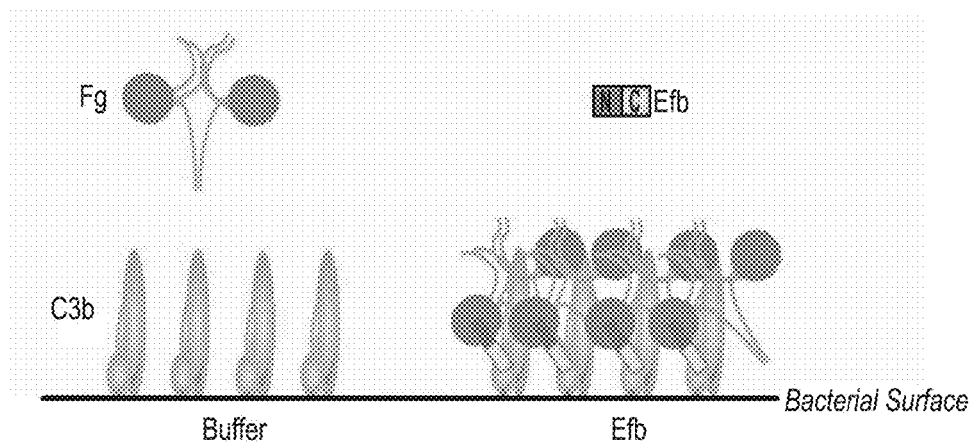
FIG. 8 shows a mechanism for phagocytosis inhibition by Efb.

FIG. 8 shows a schematic picture of the phagocytosis escape mechanism by Efb. Left, Complement activation on the bacterial surface results in massive labeling of S. aureus with C3b molecules, while Fg stays in solution. Right, S. aureus secretes Efb, which binds to surface-bound C3b via its C-terminal domain. Using its N-terminus, Efb attracts Fg to the bacterial surface. This way, S. aureus is covered with a shield of Fg that prevents binding of phagocytic receptors to important opsonins like C3b and IgG.

The coagulation system has a dual role in the host defense against bacterial infections. On one hand, coagulation supports innate defenses by entrapment and killing of invading bacteria inside clots or via the formation of small antibacterial and pro-inflammatory peptides. On the other hand, bacterial pathogens can utilize coagulation proteins to protect themselves from immune defenses. It was found that S. aureus effectively protects itself from immune recognition by secreting Efb that specifically attracts Fg from the solution to the bacterial surface creating a capsule-like shield (FIG. 8). To accomplish this, Efb forms a multimolecular complex of soluble Fg and surface-bound C3b. The fact that the levels of C3b at the bacterial surface are high and that Fg is an abundant plasma protein (1.5-4.0 g/L) makes this a very efficient anti-phagocytic mechanism. The Fg shield created by Efb effectively protects S. aureus from recognition by phagocyte receptors. The attracted Fg was found not only to block the binding of C3b to its receptor, but also hides the important opsonin IgG underneath the Fg shield. This information is critical for vaccine development against S. aureus. Generation of protective 'opsonizing' antibodies recognizing S. aureus surface structures was considered to be an important goal of vaccination. However, these antibodies will not function if they are protected underneath a layer of Fg. Including Efb in future vaccines might be beneficial as it could prevent formation of this anti-phagocytic shield and enhance the function of opsonizing antibodies. The fact that Efb is conserved among S. aureus strains may make it a suitable vaccine candidate.

In addition to Efb, S. aureus secretes two other proteins that specifically interact with the coagulation system: the S. aureus 'coagulases' named Coagulase and Von Willebrand factor binding protein are secreted proteins that activate prothrombin in a nonproteolytic manner and subsequently convert Fg into fibrin. Thereby, coagulases embed bacteria within a network of fibrin, protecting them from immune recognition and facilitate formation of S. aureus abscesses and persistence in host tissues. Coagulase and Efb are expressed at the same time during infection since they are both regulated by the SaeRS regulator for secreted (immune evasion) proteins. Efb is highly important for proper functioning of Coagulase since Efb can attract Fg to the bacterial surface. This way, Efb may aid Coagulase-dependent fibrin formation to occur close to the bacterial surface instead of in solution. Nevertheless, these studies show that Efb can block phagocytosis in the absence of prothrombin and Coagulase. However, in a more complex environment the anti-phagocytic mechanisms of Efb and S. aureus Coagulase might work synergistically. Furthermore, it seems tempting to speculate that the ability of Efb to attract Fg to the bacterial surface is also beneficial in other infection processes like adhesion. Since, Fg is an important constituent of the extracellular matrix (ECM), Efb might also facilitate binding of C3b-opsonized bacteria to the ECM. In fact, Efb was previously classified as an adhesion molecule belonging to the group of SERAMs (secreted expanded repertoire adhesive molecules). However, as a secreted protein, Efb cannot facilitate bacterial adhesion if it solely binds to Fg in the ECM without interacting with the bacterial surface. Binding to C3b-labeled bacteria via the Efb C-terminus might therefore be crucial for effective bacterial adhesion to Fg.

The pathogenic potential of *S. aureus* is a result of its versatile interactions with multiple host factors, evidenced by the fact that it can survive at multiple sites of the body causing a wide range of infections. At most body sites, *S. aureus* has to deal with cellular and humoral components of the immune system. However, increasing evidence now suggests that *S. aureus* protects itself from immune defense by forming abscess communities surrounded by capsule-like structures that prevent neutrophil invasion. This study shows that Efb might be crucial in the formation of these capsules. Furthermore, these whole blood assays show that Efb may also play an important role in *S. aureus* survival in the blood allowing it to spread to other sites of the body. Previous studies using animal models have highlighted the critical role of Efb in *S. aureus* pathogenesis. For instance, Efb delays wound healing in a rat wound infection model and is important for *S. aureus* pneumonia and abscess formation in kidneys. The in vivo studies corroborate the in vitro findings and show that complex formation can occur under physiological conditions in vivo, however, the available mouse models do not closely mimic this process during clinical infections in humans. Efb is produced in later stages of bacterial growth, thus the bacteria need time to produce Efb before they come into contact with neutrophils. Since neutrophils need to be recruited from the blood to the site of the infection, there normally is time for Efb production and complex formation, especially in the human host where an infection starts with a low number of bacteria. In contrast, in available mouse models the timing is much different as a high inoculum (up to $10^8$ bacteria) is required to establish an infection and these high numbers of bacteria trigger a strong inflammatory response resulting in that the bacteria are already phagocytized before Efb is produced. For this reason, the bacteria were mixed with their supernatants to ensure the presence of endogenous Efb during the course of the studies and chosen a model in which neutrophils are already attracted to the infection site to focus on the anti-phagocytic activity of the molecule. Future studies are needed to design and execute appropriate animal studies that overcome the limitations of current models and better reflect the clinical situation. The present disclosure provides that full-length Efb can inhibit phagocytosis in a unique way through its dual interaction with complement and Fg. Our studies indicate that Efb is a highly effective immune escape molecule that blocks phagocytosis of *S. aureus* in vivo.

Fg is a major plasma dimeric glycoprotein composed of three polypeptides, Aα, Bβ, and γ. Fg is best known for its role in the later stages in the blood coagulation cascade where thrombin proteolytically converts Fg to fibrin which then spontaneous assemble into the ultrastructural core of the clot. However, Fg is also a critical participant in a number of different physiological processes such as thrombosis, wound healing, and angiogenesis and in innate immune defense against pathogens. A role for Fg in inflammation is evident from analysis of Fg knockout mice, which exhibit a delayed inflammatory response as well as defects in wound healing. Furthermore, the fibrinopeptides, generated by thrombin cleavage of Fg, are potent chemoattractants, which can act as modulators in inflammatory reactions. A genetically engineered mouse expressing a mutant form of Fg that is not recognized by the leukocyte integrin $\alpha_M\beta_2$ has profound impediment in clearing *S. aureus* following intraperitoneal inoculation. This study highlights the importance of Fg interactions with the leukocyte integrin $\alpha_M\beta_2$/Mac-1/complement receptor 3 in the clearance of staphylococci. Fg also interacts with the complement system and modulates complement dependent clearance of bacteria.

Recent studies of some of the secreted Fg binding *S. aureus* virulence factors point to yet another mechanism of Fg dependent inhibition of bacterial clearance. In a mouse model of *S. aureus* abscess formation, Fg accumulates and is co-localized with coagulase (coa) and von Willebrand factor binding protein (vWbp) within the staphylococcal abscess lesions. The profound amount of Fg in the periphery of the abscess forms a capsule-like structure that borders the uninfected tissue and prevents phagocytes from accessing and clearing bacteria in the center of the abscess. Coagulase (Coa) is an "old" *S. aureus* hall mark protein best known for its ability to induce blood/plasma coagulation which allows the classification of the staphylococcal genus into coagulase positive and negative species. More recent studies have shown that Coa is a critical virulence factor in some staphylococcal diseases. Coa dependent blood coagulation is initiated when Coa activates the zymogen prothrombin by insertion of the $Ile^1$-$Val^2$ residues present at the N-terminus of Coa into the $Ile^{16}$ pocket of prothrombin, inducing a conformational change and a functional active site in the serine protease. This activation process does not involve proteolytic cleavage of prothrombin which is required in physiological blood coagulation. The Coa/prothrombin complex then recognizes Fg as a specific substrate and converts it into fibrin. The crystal structure of Coa/prothrombin complex reveals that the exosite 1 of α-thrombin, the Fg recognition site, is blocked by D2 domain of Coa. This information raises questions concerning the nature of Fg recognition and subsequent cleavage by the complex. Coa can interact with Fg directly without the aid of prothrombin and this interaction site(s) was tentatively located to the C-terminus of Coa. The C-terminal region of Coa is comprised of tandem repeats of a 27-residue sequence that is relatively conserved among strains but the numbers of repeats varies from 5 to 8 in different strains. The Fg-binding activity of Coa was characterized and show that Coa contains multiple copies of a Fg binding motif that is structurally and functionally related to the Fg binding motifs in Efb. The interaction of this common motif with Fg is analyzed in some detail.

Figure 9A:
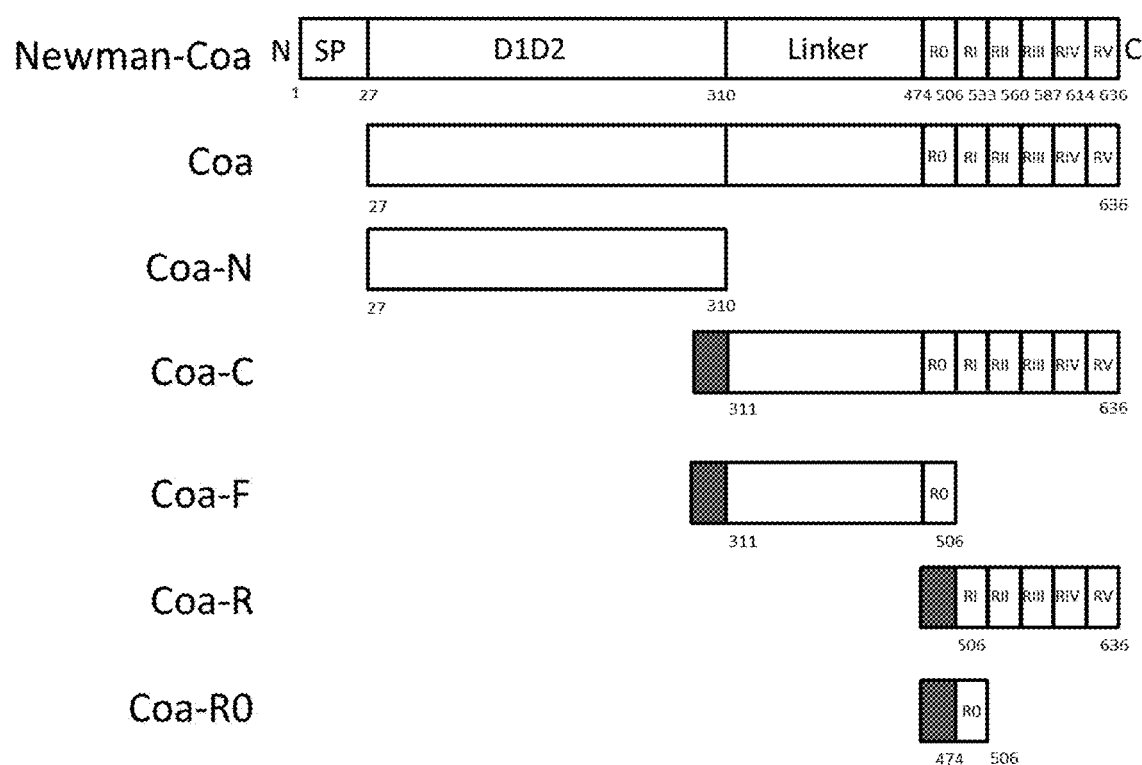

FIG. 9A illustrates a schematic presentation of recombinant Coa fragments generated in this study. Coa is depicted in its secreted form Coa (27-636) lacking the signal peptide (1-26). The N-terminus of Coa (Coa-N; Coa 27-310) constitutes D1D2 prothrombin binding domain. The C-terminus of Coa (Coa-C; Coa 311-636) includes the central region and the tandem-repeat region. The Coa-C further divides into two parts, the Coa-R is corresponding to the tandem-repeat region covering residue 506-636, and the Coa-F fragment covering residues 311-505. Recombinant protein Coa-R0 corresponds to the residues 474-506 residues. In the figure, SP represents the signal peptide, N shows the N-terminus of the protein, C represents the C-terminus of the protein and the dark grey box represents the GST tag. FIG. 9B illustrates an ELISA assays of GST-tagged Coa fragments binding to immobilized Fg. Open circle, Coa (Coa 27-636); open upright triangle, Coa-N(Coa 27-310); open inverted triangle, Coa-C(Coa 311-636); closed circle, Coa-R (Coa 506-636); closed diamond, Coa-F (Coa 311-505). FIG. 9C is a table that shows the protein concentration at which the reaction rate is half of Vmax (Km), and the goodness of fit ($R^2$). FIG. 9D illustrates the effect of peptide Efb-O on inhibition of rCoa binding to Fg. Increasing concentration of Efb-O were incubated with 4 nM GST-tagged Coa proteins in Fg-coated microtiter wells. Control, BSA.

Staphylococcal Coagulase contains multiple Fibrinogen binding sites. With the goal to identify the Fg-binding motifs in Coa we first sought to locate the Fg-binding site(s) in the protein. To this end, a panel of recombinant proteins covering different segments of Coa (FIG. 9A) was constructed and examined their Fg-binding activities in an ELISA-type binding assay. Earlier observations that Coa interacts with Fg primarily through the disordered C-terminal part of the protein (Coa-C, corresponding to residues Coa 27-636) were confirmed. Fg-binding to recombinant Coa-C is a concentration dependent process that exhibits saturation kinetics and shows half maximum binding at 7.5 nM (FIG. 9B). The tandem repeat region of Coa (fragment Coa-R, corresponding to residues Coa 506-636) binds to Fg in a similar way but with a higher apparent affinity (0.8 nM) compared to that of the whole C terminus (Coa-C). A recombinant protein containing the segment between the D1D2 domain and Coa-R was therefore constructed (fragment Coa-F, corresponding to residues Coa 311-505) and that recombinant Coa-F also binds Fg (FIG. 9B). The N-terminal D1D2 domain of Coa (Coa-N) that contains the prothrombin binding activity also interacts with Fg. However, the apparent affinity observed for Coa-N binding to Fg was much lower than that exhibited by Coa-C and the Fg-binding activity of the Coa-N was therefore not further examined in this study.

The fibrinogen binding activities in Coagulase and Efb are functionally related. Fg-binding activity of Efb protein has been located to a disordered region in the N-terminal part of the protein. Two related Fg-binding segments in Efb named Efb-O (corresponding to Efb 68-98) and Efb-A (corresponding to Efb 30-67) were identified (FIG. 2A). The Efb-O segment was determined to have a higher affinity for Fg compared to Efb-A but that the two motifs likely bound to the same region in Fg since recombinant Efb-O (rEfb-O) effectively inhibited rEfb-A binding to the host protein. Because the Fg-binding activities in Efb and Coa are both located to disordered regions and both proteins can induce a protective Fg containing barrier we explored the possibility that the Fg-binding motifs in the two proteins are functionally related. To this end it was used a competition ELISA where the binding of recombinant Coa to Fg coated wells was quantitated in the presence of increasing concentrations of the synthetic peptide Efb-O (sEfb-O) that mimics the high affinity Fg-binding motif in Efb. Peptide sEfb-O effectively inhibited recombinant Coa binding to Fg (FIG. 9D), suggesting that Coa and Efb are functionally related and that the dominant Fg-binding motifs found in the two proteins likely bind to the same or overlapping sites in Fg.

Figure 10B:
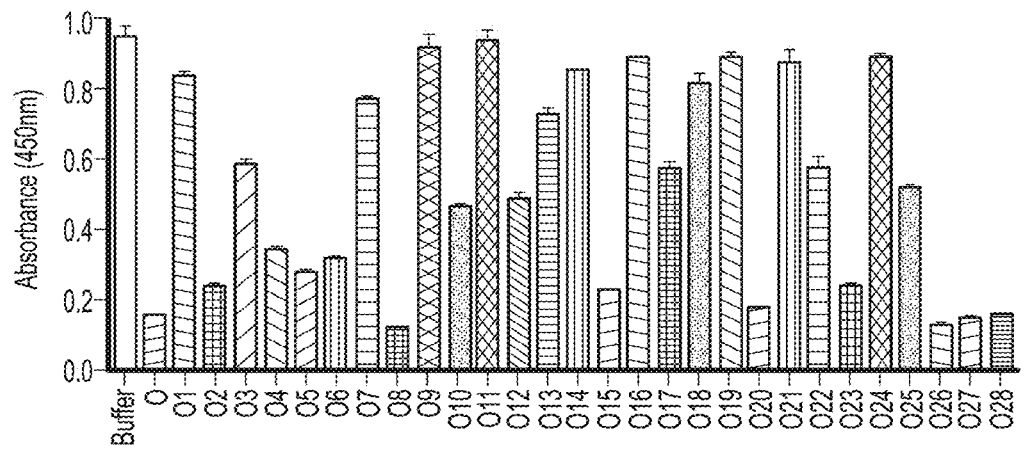
FIG. 10B is a plot of the Efb-O variant peptides inhibit rEfb-O (5 nM) binding to immobilized Fg in solid phase assay.
Figure 10C:
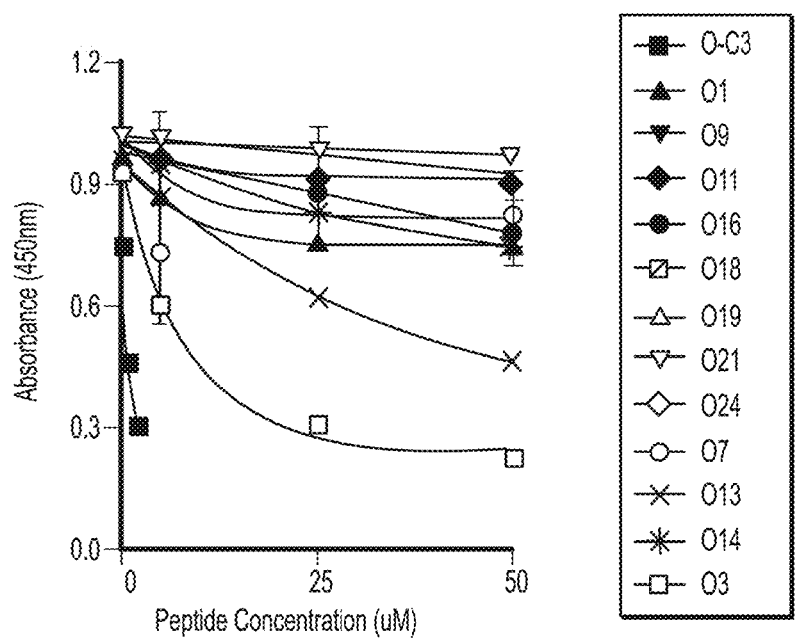
FIG. 10C is a plot showing selected peptides inhibit rEfb-O binding to immobilized Fg. Increasing concentrations of Efb peptides were incubated with 5 nM rEfb-O in Fg-coated microtiter wells.

FIG. 10A is a table of the Efb-O variant peptides were synthesized where each residue in the sequence is individually replaced with Ala (or Ser when the native a.a. is Ala). FIG. 10B is a plot of the Efb-O variant peptides inhibit rEfb-O (5 nM) binding to immobilized Fg in solid phase assay. Wells were coated with 0.25 µg/well Fg. Peptides (2 µM) were mixed with rEfb-O proteins (5 nM) and incubated in the Fg wells for 1 hour. FIG. 10C is a plot showing selected peptides inhibit rEfb-O binding to immobilized Fg. Increasing concentrations of Efb peptides were incubated with 5 nM rEfb-O in Fg-coated microtiter wells. To identify the residues in Efb-O that are important for Fg binding an Alanine scanning approach was used. A panel of Efb-O variant peptides were synthesized where each residue in the sequence is individually replaced with Ala (or Ser when the native a.a. is Ala; FIG. 10A). The individual peptides are then examined for their ability to compete with the binding of rEfb-O (5 nM) to immobilized Fg. The inhibitory activity of the peptides was compared at a fixed concentration (2 µM) for each peptide (FIG. 10B) and at increasing concentrations for selected peptides (FIG. 10C). As the Efb-O sequence is found in a disordered segment of the protein, the peptides are likely to be very flexible in solution. Therefore, a peptide's inhibitory activity reflects its relative affinity for Fg.

As expected, the control wild-type peptide sEfb-O efficiently blocked the corresponding recombinant protein rEfb-O from binding to Fg, demonstrating that peptide sEfb-O has full Fg binding activity compared to rEfb-O. Surprisingly Ala substitution of over 15 residues distributed throughout the 25 amino acid long Efb-O motif resulted in loss or significant reduction in inhibitory activity (FIG. 10B), suggesting that residues throughout the entire segment are involved in Fg-binding. The results revealed that peptides in which Ala replaces residues $K^1$, $I^3$, $H^7$, $Y^9$, $I^{11}$, $E^{13}$, $F^{14}$, $D^{16}$, $G^{17}$, $T^{18}$, $F^{19}$, $Y^{21}$, $G^{22}$, $R^{24}$ and $P^{25}$ lose their ability to inhibit rEfb-O binding (shown in red color in FIG. 10B), indicating that these residues are critical for Efb-O to bind to Fg (FIG. 10B). Ala replacement of residues $Ile^3$ and $Glu^{13}$ resulting in peptides sEfb-03 (I3A) and sEfb-013 (E13A), respectively, showed a markedly reduced yet significant dose dependent inhibitory activity suggesting that the residues $Ile^3$ and $Glu^{13}$ play some but less important roles in the Fg interaction (FIG. 10C).

Figure 11E:
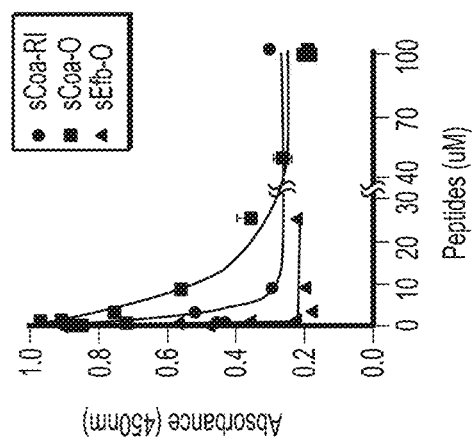
FIGS. 11D and 11E show the effect of Coa and Efb peptides on inhibition of rEfb-N (Efb 30-104) (FIG. 11D) and rCoa-C (Coa 311-636) (FIG. 11E) binding to Fg by the inhibition ELISA assays.
Figure 11D:
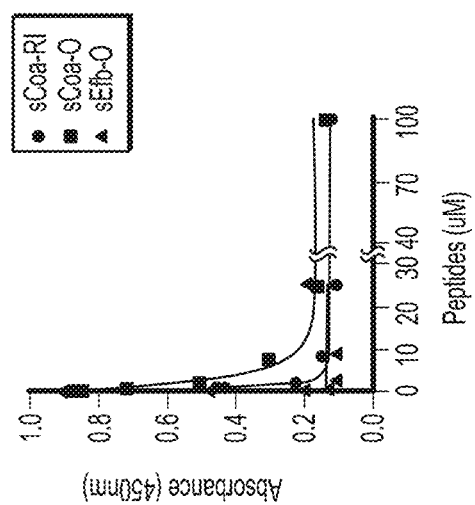

Coa-F contains an Efb like fibrinogen binding motif. FIG. 11A is an image of a ClustalW alignment of amino acid sequence from Efb-O (Efb 68-98) and Coa from Newman strain (col-Newman). Sequence similarity was identified at Coa 474-505. Bold letters denote conserved residues and underlined letters represent similar residues. FIGS. 11B and 11C show a comparison of amino acid sequence of Efb-O with Coa 474-505 (FIG. 11B) and Coa 506-532 (FIG. 11C). Large letters in Efb-O indicate the residues important for Fg binding. The red letters show the identical residues and the yellow letters indicate the similar residues. FIGS. 11D and 11E shows the effect of Coa peptides on inhibition of rEfb-N (Efb 30-104) (FIG. 11D) and rCoa-C(Coa 311-636) (FIG. 11E) binding to Fg by the inhibition ELISA assays. Increasing concentration of Coa peptides was incubated with 2 nM GST fusion proteins in Fg-coated microtiter wells. Closed square, sCoa-O; closed circle, sCoa-RI; closed triangle, sEfb-O.

Next, sequences similar to the Fg-binding motifs in Efb were identified in Coa by comparing the amino acid sequence of Efb-O with Coa and found that a segment corresponding to residues Coa 474-505, named Coa-O, showed 56% amino acid identity and 75% similarity to that of the Efb-O sequence (FIG. 11A). Strikingly, of the residues in Efb-O determined to be important for Fg-binding (FIG. 10B) and FIG. 11B all but three are conserved in Coa-O (FIG. 10B, shown in large red and orange letters), indicating that Coa-O likely constitutes an Efb-like Fg-binding motif. A peptide was synthesized that corresponds to the Coa-O sequence (sCoa-O) and determined its Fg binding activity in a competition ELISA. Microtiter wells were coated with Fg and binding of the recombinant N-terminal segment of Efb (rEfb-N), that harbors the two Fg binding sites, was quantitated in the presence of increasing concentration of different synthetic peptides. As expected, the control peptide sEfb-O potently inhibited rEfb-N binding to the Fg surface (FIG. 11D). Peptide sCoa-O also acted as a potent inhibitor of the rEfb-N/Fg interaction (FIG. 11D), demonstrating that the Coa segment covered by residues 474-505 contains a Fg-binding site. The result also suggested that Coa-O likely competed with Efb-O for the same site in Fg.

It is noted that the repeated sequence of Coa contains remnants of the Efb Fibrinogen binding motif. The C-terminus of Coa harbors tandem repeats of a 27-residues segment and this region has been shown to bind Fg (FIGS. 9A and 9B). However, a Fg-binding motif has not been identified in the repeat region of Coa. An initial blast search failed to identify an Efb like Fg-binding motif in the Coa repeats but when the Efb-O sequence and the first repeat sequence were over-layered and showed that remnants of the Efb motif are also found in the Coa repeat sequences (FIG. 11C). Importantly the common residues are some of the ones shown to be critical for Efb-O binding to Fg (Bold letters represent the identical residues and underlined residues represent the similar residues). This observation suggests that the Coa repeats may bind Fg and possibly help define a functional register in the repeats. To investigate if the Coa repeats indeed have Fg binding activity, a peptide that constitutes the first 27 residues (Coa 506-532) (named sCoa-RI) was synthesized. This assumes that the functional Fg-binding repeats are directly following onto Coa-O (474-505). The Fg-binding activity of sCoa-RI was compared with those of sCoa-O and sEfb-O in competition ELISAs (FIGS. 11D, 11E) where increasing concentrations of the peptides were used to inhibit the binding of rEfb-N (FIG. 11D) or rCoa-C (FIG. 11E) to Fg. All three peptides effectively inhibited rEfb-N binding to Fg, suggesting that the sCoa-RI also contains a Fg binding site likely targeting the same site in Fg as that recognized by Efb and Coa-O. Furthermore, sCoa-RI was a somewhat more effective inhibitor than sCoa-O despite the fact that the Coa-O sequence is more similar to that of Efb-O than Coa-RI. This observation suggests that some of the residues unique to Coa-RI are also participating in the Fg interaction. To determine what residues in Coa-RI are important for Fg-binding the Ala scanning approach was again used.

Figure 12B:
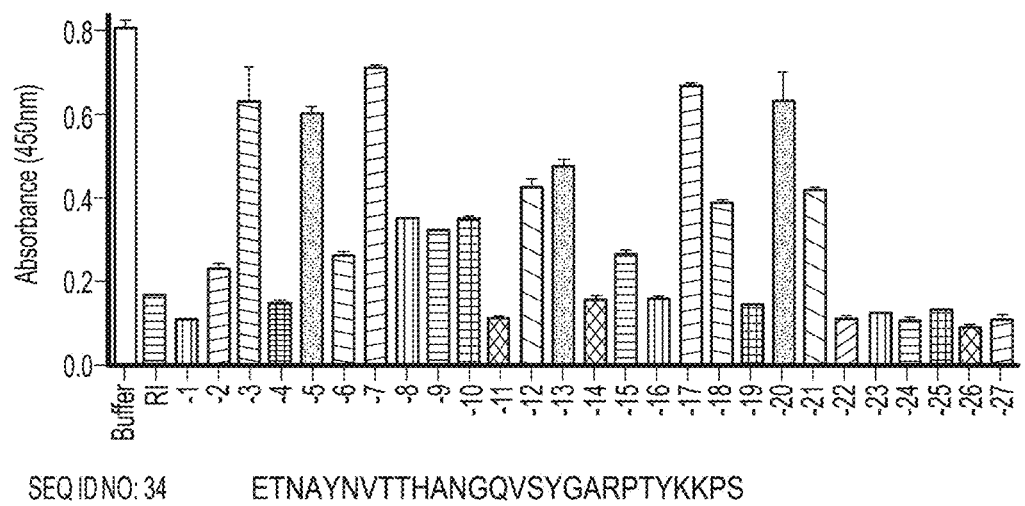
FIG. 12B is shows sCoa-RI variant peptides (50 µM) inhibit GST-tagged rCoa-C(Coa 311-636) (2 nM) binding to immobilized Fg in solid phase assay.

The residues in Coa-RI important for fibrinogen binding. FIG. 12A is a panel of coa-RI variant peptides were synthesized where each residue in the sequence is individually replaced with Ala (or Ser when the native a.a. is Ala). FIG. 12B shows inhibition of GST-tagged rCoa-C(Coa 311-636) (2 nM) binding to immobilized Fg in solid phase assay by sCoa-RI variant peptide (50 μM). Wells were coated with 0.25 μg/well Fg. Labels -1, -2, -3, -4, -5, -6, -7, -8, -9, -10, -11, -12, -13, -14, -15, -16, -17, -18, -19, -20, -21, -22, -23, -24, -25, -26, -27 refer to Coa-RI-1, Coa-RI-2, Coa-RI-3, Coa-RI-4, Coa-RI-5, Coa-RI-6, Coa-RI-7, Coa-RI-8, Coa-RI-9, Coa-RI-10, Coa-RI-11, Coa-RI-12, Coa-RI-13, Coa-RI-14, Coa-RI-15, Coa-RI-16, Coa-RI-17, Coa-RI-18, Coa-RI-19, Coa-RI-20, Coa-RI-21, Coa-RI-22, Coa-RI-23, Coa-RI-24, Coa-RI-25, Coa-RI-26, Coa-RI-27, respectively. FIG. 12C is a comparison of amino acid sequence of Efb-O with Coa-RI. FIG. 12D is a Fg-binding register of tandem repeats in Coa. Bold letters denote the residues that are important for Fg binding. The peptide panel generated and tested is shown in FIG. 12A. Binding of a fixed concentration of rCoa-C (2 nM) to immobilized Fg was determined in the presence of a fixed concentration of these peptides (50 uM) (FIG. 12B). Interestingly, results revealed a similar pattern to that observed for Efb-O showing that the Ala substitution of over 13 residues distributed throughout the 27 amino acid long Coa-RI motif resulted in loss or significant reduction in inhibitory activity (FIG. 12B). This result suggests that, similar to Efb-O, residues in the entire segment of Coa-RI are involved in Fg binding. The results also showed that peptides in which alanine replaces residues $N^3$, $Y^5$, $V^7$, $T^8$, $T^9$, $H^{10}$, $N^{12}$, $G^3$, $V^{15}$ $Y^{17}G^{18}$ $R^{20}$ and $P^{21}$ (FIG. 12B) lose their ability to inhibit rCoa-C binding (FIG. 12B, shown), indicating that these residues are critical for Coa-RI to bind to Fg. Efb-O and Coa-RI sequences were compared to see how the critical residues in the two motifs line up. Strikingly, despite difference in numbers of residues and no extensive sequence identities between them, the critical residues in Coa-RI correlate with similar residues in the corresponding position in Efb-O (FIG. 12C, bold, identical residues; underline, similar residues, italics, non-similar residues). Furthermore, sequence comparisons within the different 27 residues repeats showed that the identified critical residues are conserved or replaced by similar residues (FIG. 12D).

Figure 14A:
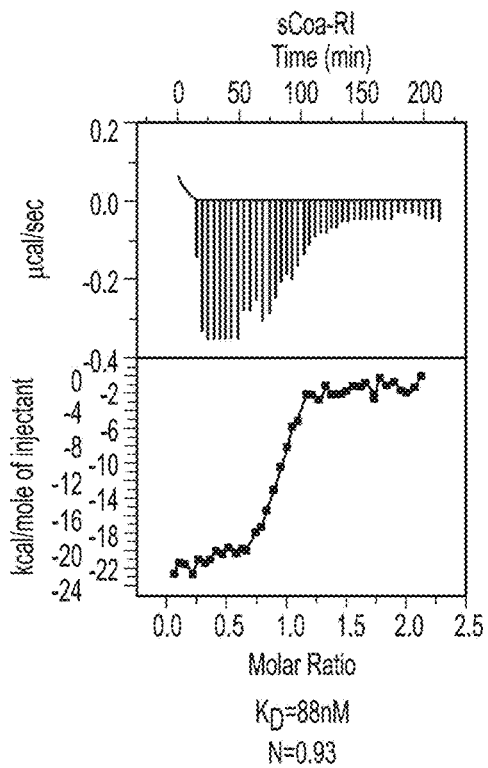
FIGS. 14A-14C show a characterization of the interaction of Fg-D fragment with Coa peptides by VP-ITC.
Figure 14B:
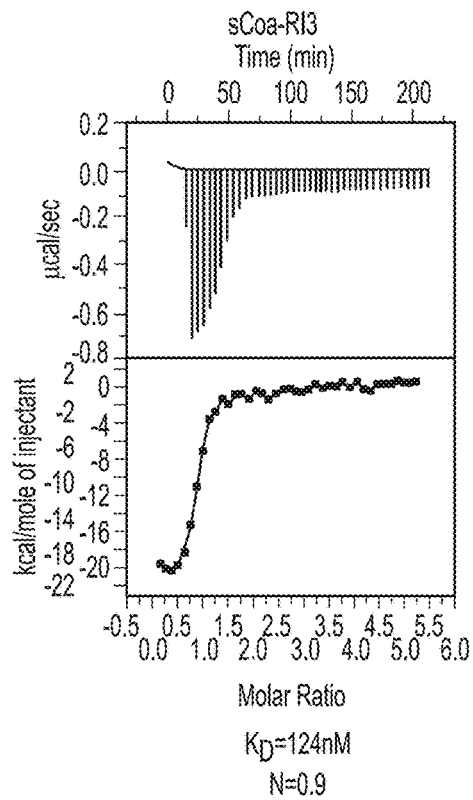
Figure 14C:
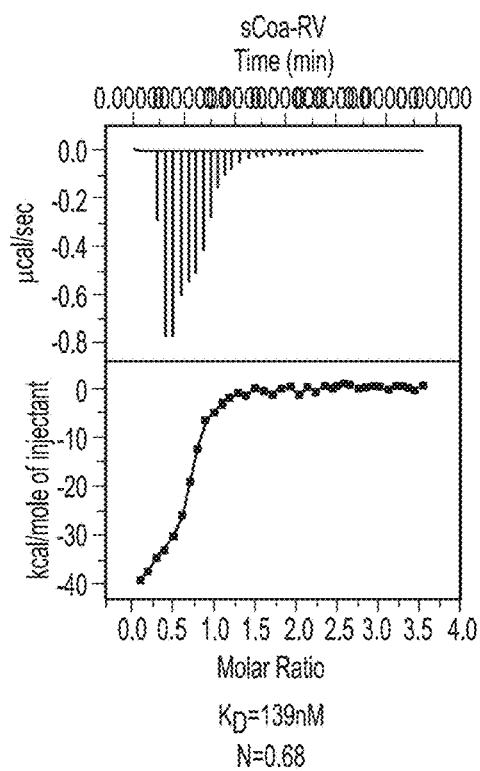

FIG. 13A is a schematic presentation of Coa peptides. FIG. 13B is a plot of the effect of Coa peptides on inhibition of rCoa-C binding to fibrinogen. Increasing concentrations of synthetic peptides were incubated with 4 nM GST fusion protein in Fg-coated microtiter wells. Peptide sCoa-RI appears to be the most potent inhibitor. Closed circle, sCoa-RI; closed square, coa-R12 peptide; closed upright triangle, coa-R13; closed inverted triangle, coa-RI4; closed diamond, coa-RV1; open circle, coa-RV2; open square, coa-RV3; open triangle, coa-RV4. In previous studies the repeated unit in Coa is proposed to start with residues alanine ($A^{497}$) in *S. aureus* strain Newman. This register was based exclusively on sequence comparisons of Coa from different strains. To experimentally define a register of the repeats based on their Fg-binding function a panel of 27-residues peptides was synthesized and each peptide has 22-24 residues overlapped and largely covering the repeat I (RI) and repeat V (RV) (FIG. 13A). The Fg binding activities of these peptides were then investigated in a competition ELISA where the binding of rCoa-C to Fg coated microtiter wells were determined in the presence of increasing concentrations of peptide (FIG. 13B). It was observed that although peptides sCoa-RI, —RI$_2$, —RI$_3$, —RI$_4$ and —RV$_1$ showed some inhibitory activity, peptide sCoa-RI appears to be the most potent inhibitor among these eight peptides, suggesting that sCoa-RI (Coa 506-532) has the highest affinity for Fg (FIG. 13B) and that sCoa-RI likely represents a functional repeat unit that interacts with Fg. Notably, peptide sCoa-RV$_2$ (Coa 605-631), representing the previously proposed register, did not inhibit Fg binding in the experimental condition tested (FIG. 13B), indicating that this peptide has very low, if any, Fg binding activity. The results show that the functional (Fg binding) register of the repeat section is as outlined in FIG. 12D.

sCoa-RI, -RI3 and -RV bind to fibrinogen Coa-RI binds with higher affinity than other Coa peptides to Fg-D. FIGS. 14A-C shows a characterization of the interaction of Fg-D fragment with Coa peptides by VP-ITC. Binding isotherms for the interaction of Fg-D with Coa peptide sCoa-RI (FIG. 14A), sCoa-R13 (FIG. 14B) and sCoa-RV (FIG. 14C) were generated by titrating the peptides (~200 μM) into an ITC cell containing 10 μM Fg-D. The top panels show heat difference upon injection of coa peptides, and the lower panels show integrated heat of injections. The data were fitted to a one-binding site model (bottom panels), and binding affinities are expressed as dissociation constants (K$_D$) or the reciprocal of the association constants determined by Microcal Origin software. N represents the binding ratio. To generate more quantitative binding data for the Coa peptide Fg interaction isothermal titration calorimetry and titrated the Coa peptides into a solution containing a fixed concentration of Fg-D fragments was used. Synthetic peptide sCoa-RI (Coa 506-532) bound to Fg-D fragment with a high affinity (K$_D$=88 nM) and a binding stoichiometry is 0.93 (FIG. 14A), suggesting that one molecule of sCoa-RI bound to one Fg-D molecule. Interactions between peptide sCoa-RI3 (Coa 502-528) and Fg-D fragments revealed an affinity of 124 nM (K$_D$); whereas sCoa-RV1 (Coa 610-636) had a K$_D$ of 139 nM (FIG. 14B and FIG. 14C, respectively). These results corroborated with our competition ELISA results (FIG. 13B) and showed that sCoa-RI (Coa 506-532) bound Fg-D stronger than sCoa-R13 (Coa 502-528) and sCoa-RV1 (Coa 610-636).

Figure 15:
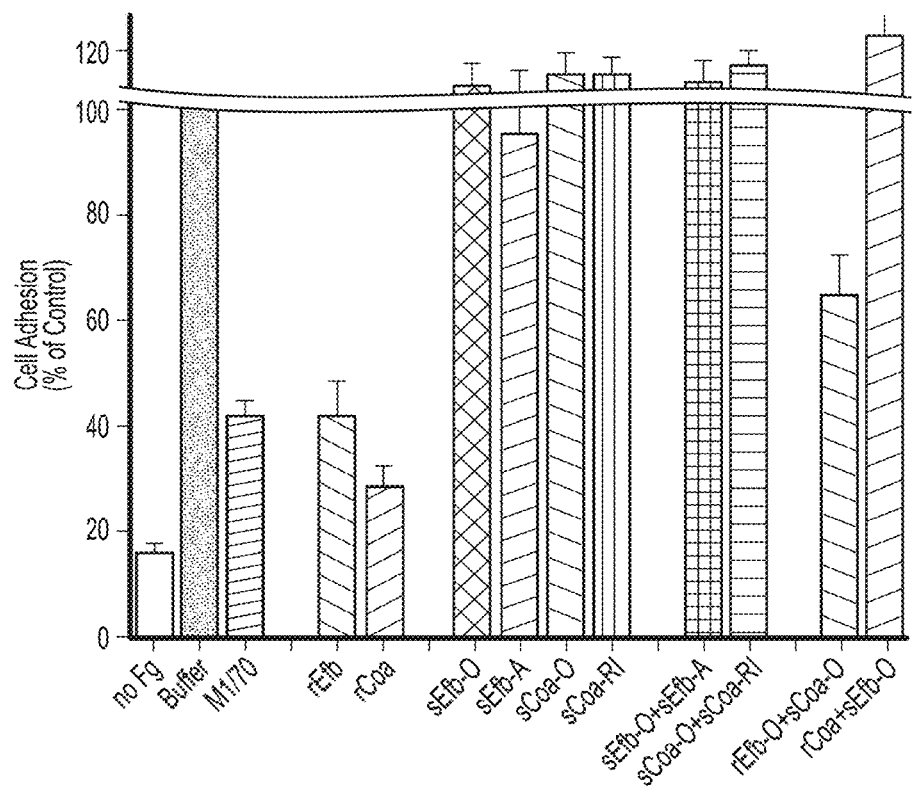
FIG. 15 shows Coa and Efb prevent monocytic cells from adherence to fibrinogen.
Figure 17:
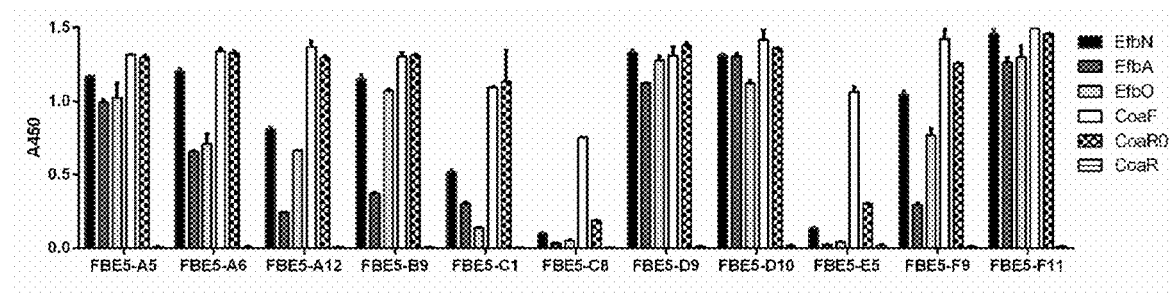
FIG. 17 shows the binding of FBE5 antibodies to Coa and Efb fragments. The 11 monoclonal antibodies, selected against Coa-$C_{311-636}$ were tested for binding to truncated recombinant proteins of the C-terminal part of Coagulase, namely Coa-$F_{311-505}$, Coa-$R0_{474-505}$ and Coa-$R_{506-636}$, and different fragments of Efb, namely Efb-$N_{30-105}$, Efb-$A_{30-67}$ and Efb-$O_{68-98}$. Coa-$F_{311-505}$, Coa-$R0_{474-505}$ and Coa-$R_{506-636}$, and Efb-$N_{30-105}$, Efb-$A_{30-67}$ and Efb-$O_{68-98}$ proteins were immobilized (200 ng/well) in a 96 well microtiter plate and probed with the indicated antibodies at a fixed concentration (0.5 µg/ml) in a solid-phase binding assay. Binding was observed for all of tested antibodies and it is noticeable that the antibodies displayed variable apparent affinities to the different Efb and Coa fragments. None of the FBE5 antibodies bound to Coa-$R_{506-636}$.
Figure 18:
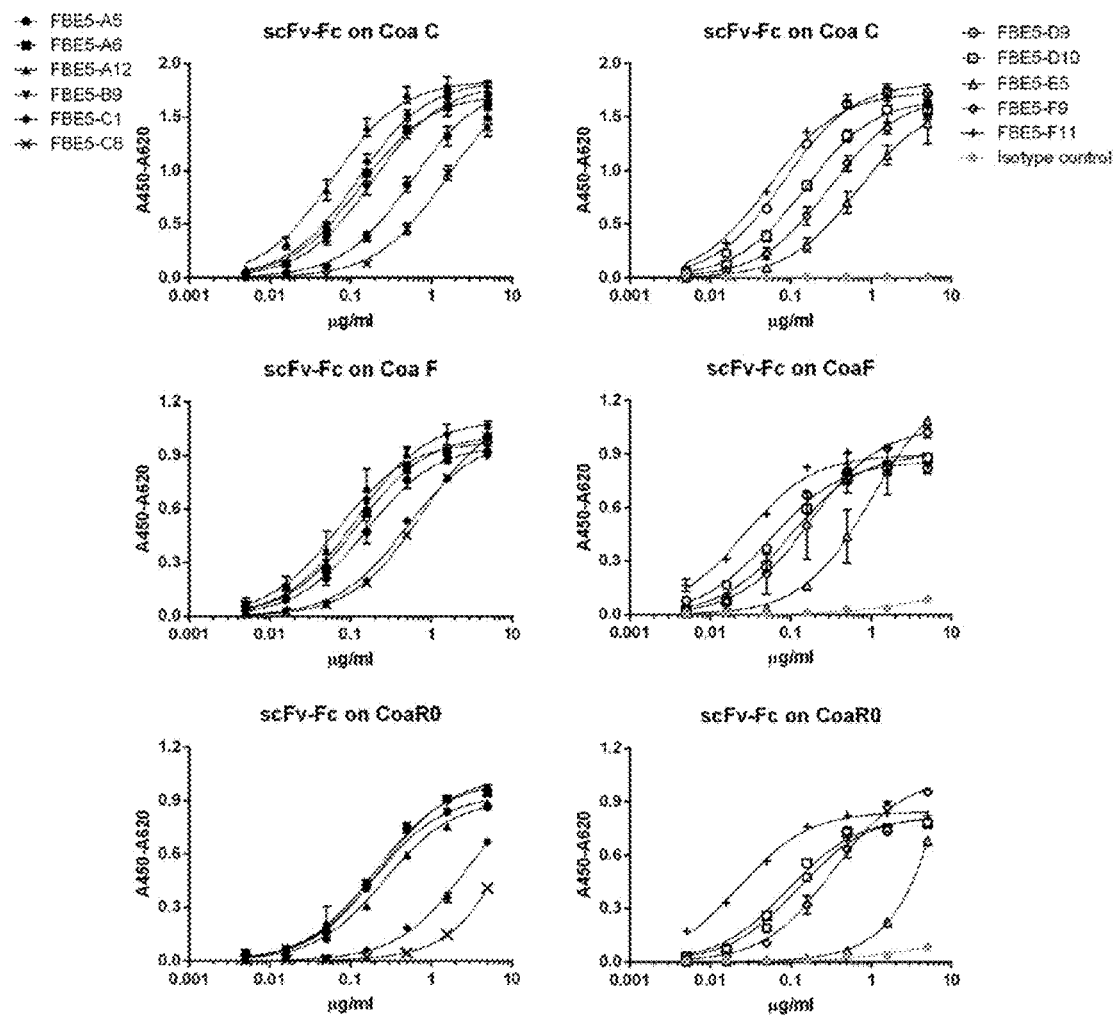
FIG. 18 shows the dose-dependent binding of FBE5 antibodies to Coa fragments. The 11 monoclonal antibodies selected against Coa-$C_{311-636}$ were titrated on different truncated recombinant proteins of the C-terminal part of Coagulase, namely Coa-$C_{311-636}$, Coa-$F_{311-505}$, Coa-$R0^{474-505}$. Recombinant Coa-$C_{311-636}$. Coa-$F_{311-505}$. Coa-$R0_{474-505}$ proteins were resuspended in 1×TBS buffer and immobilized (200 ng/well) in a 96 well microtiter plate overnight at 4° C. and probed with the selected antibodies in a solid-phase binding assay. Purified scFv-Fc were diluted in 2% BSA+1×PBS+0.05% TWEEN® 20 and a 10-fold serial dilution of each scFv-Fc was prepared. Varying concentration of scFv-Fcs' were incubated with Coa proteins for 1 hour at room temperature with shaking at 250 rpm. The bound scFv-Fv were detected using polyclonal α-human IgG HRP-conjugated Ab (P0214, Dako), diluted 1:10000 in 2% BSA+1×PBS+0.05% TWEEN® 20. SIGMAFAST™ OPD tablets (P9187, Sigma) were used for development as per manufacturer's instructions. Dose dependent binding was observed for all FBE5 antibodies and it is noticeable that the antibodies display variable apparent affinities to the different proteins. An irrelevant isotype-matched antibody (isotype control) was tested. As shown, no binding was detectable for this latter antibody.
Figure 20:
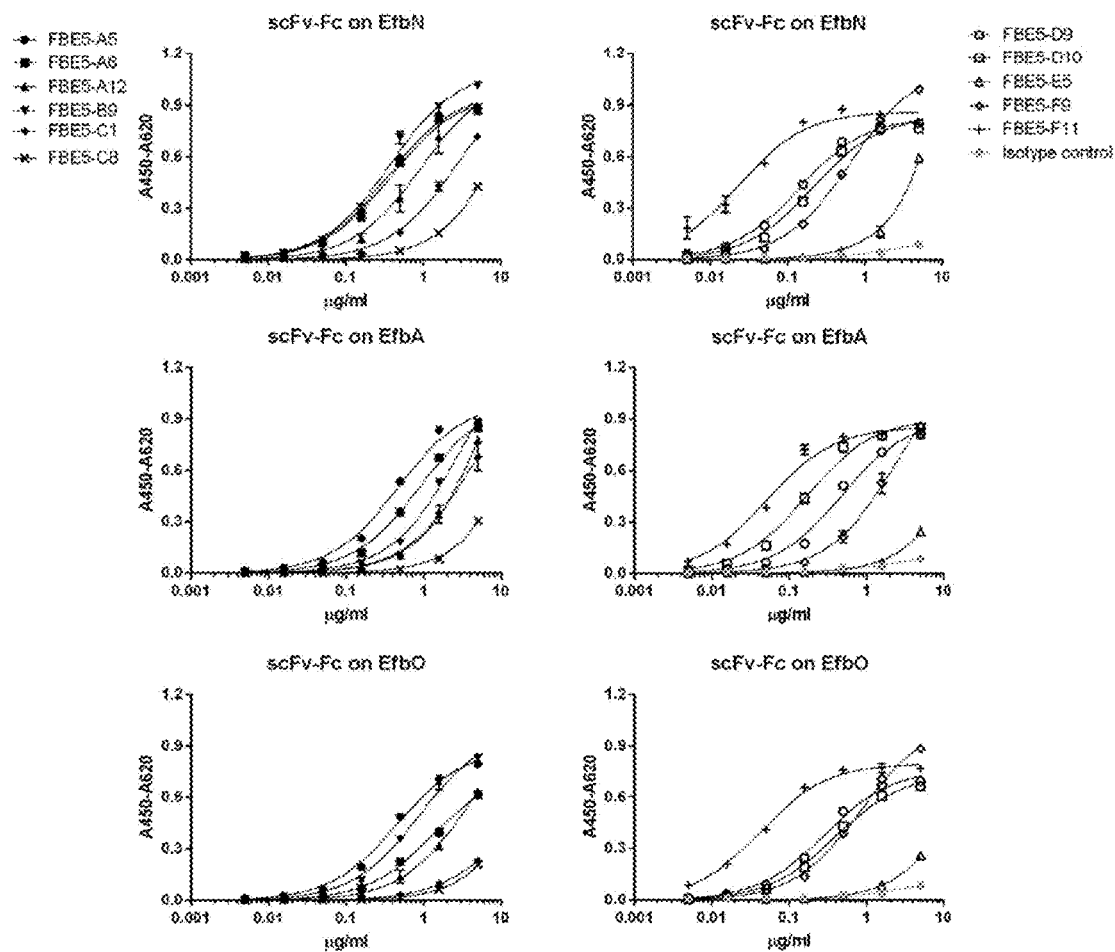
FIG. 20 shows the dose-dependent binding of FBE5 antibodies to recombinant truncated Efb proteins. The 11 monoclonal antibodies selected against Coa-$C_{311-636}$ were titrated on different portions of the N-terminal part of Efb protein, that, as reported in previous claims, has sequence and functional homology to Coagulase. Recombinant proteins Efb-$N_{30-105}$, Efb-$A_{30-67}$ and Efb-$O_{68-98}$ were resuspended in 50 mM sodium carbonate pH 9.6 and immobilized (200 ng/well) in 96 well microtiter plate overnight at 4° C. and probed for recognition in a solid-phase binding assay. These proteins were probed with different quantities of the selected antibodies. Ten-fold serial dilution of scFv-Fc were prepared in 2% BSA+1×PBS+0.05% TWEEN® 20 and incubated with immobilized protein for 1 hour at room temperate with shaking at 250 rpm. Bound scFv-Fc were detected using α-human IgG HRP-conjugated Ab (P0214, Dako) diluted 1:10000 in 2% BSA+1×PBS+0.05% TWEEN® 20. SIGMAFAST™ OPD tablets (P9187, Sigma) were used for development as per manufacturer's instructions. Dose dependent binding was observed for all the antibodies tested and it is noticeable that the antibodies display variable apparent affinities to the different proteins. An irrelevant isotype-matched antibody (isotype control) was tested. As shown, no binding was detectable for this latter antibody.

FIG. 15 shows Coa and Efb prevent monocytic cells from adherence to fibrinogen. Attachment of THP-1 cells to Fg immobilized on the 48-wells was inhibited by the addition of monoclonal αM antibody M1/70 (20 µg/ml), rEfb (0.2 µM) and rCoa (0.5 µM). Addition of single peptide alone (sEfb-O, sEfb-A as well as sCoa-RI and sCoa-O, respectively, 0.5 uM each) or combination of two peptides together (sEfb-A+sEfb-O) or (sCoa-O+sCoa-RI), 0.5 µM each, did not inhibit THP-1 adherence. However, preincubation of sCoa-O peptide (50 uM) with rEfb (0.2 uM) or sEfb-O (50 µM) with rCoa (0.2 µM) reverses the inhibitory activities elicited by rEfb or rCoa. Error bars, S.D., n>3. As Coa and Efb share similar Fg binding motif and could inhibit each other from binding to Fg, it was explored if Coa could also inhibit THP-1 monocytic cells adherence to Fg. THP-1 cells adhere to immobilized Fg primary through αMβ2 integrin (also named Mac-1, CR3). In consistent to previously reported, antibody against αM (M1/70) inhibits THP-1 adherence to immobilized Fg (FIG. 15), confirming adherence of THP-1 cells to Fg is primary mediated by αMβ2 integrin. Efb has been shown to block neutrophil-Fg interaction in an αMβ2 dependent mechanism. Here as expected, Efb also efficiently inhibited THP-1 binding to Fg (FIG. 15). Similar to Efb, rCoa protein, that harbors multiple Fg binding motif, could also inhibit cell adherence to Fg surface. Interestingly, application of single individual synthetic peptides efb-O or efb-a that each contains one single Fg binding motif or in combination of two peptides (sEfb-O+sEfb-A) together did not show an effect. Similar phenomena were observed for sCoa-O and sCoa-RI, suggesting that inhibition of THP-1 cells adherence to Fg requires more than one Fg binding sites in one molecule. This is further supported by the observation that an excess amount of single peptide can partially, if not all, resolve the inhibitory effect mediated by rEfb or rCoa proteins (FIG. 15). In this situation, an excess amount of peptide sEfb-O or sCoa-O (50 uM) was mixed with rCoa (0.5 uM) or rEfb-N (0.2 uM), respectively, in the adherence assay. Coa is functionally related to Efb and that similar to Efb and Coa also inhibits monocytic-Fg interaction in αMβ2 dependent process.

The pathogenic potential of *S. aureus* is a result of its multitude of virulence factors and their versatile interactions with multiple host factors. As a result *S. aureus* can survive and strive at many tissue sites in the host and cause a wide range of diseases. Fibrinogen is a surprisingly common target for many of the staphylococcal virulence factor proteins. The known Fg-binding staphylococcal proteins largely fall into two groups: a family of structurally related cell-wall anchored proteins of the MSCRAMM type that include ClfA, ClfB, FnbpA, FnbpB and Bbp/SdrE) and a group of secreted smaller proteins (sometimes referred to as the SERAMs) that include Efb, Coa, von Willebrand factor-binding protein (vWbp), extracellular matrix binding protein (Emp) and extracellular adherence protein (Eap). The Fg-binding sites in the MSCRAMs are located to a segment of the proteins composed of two IgG-folded sub-domains that bind Fg by variants of the so called "dock, lock, and latch" mechanism. In this mechanism a short, disordered segment of Fg docks in a trench formed between the two sub-domains through beta-complementation to a strand of the second sub-domain which subsequently triggers conformational changes in the MSCRAMM resulting in the subsequent steps.

The secreted proteins do not share a common domain organization and the mechanisms of Fg-binding used by these proteins remain largely unknown. However, these proteins do have some features in common. One, they all interact with multiple ligands and Fg is the common ligand among them. Two, they all contribute to *S. aureus* abscess formation in animal infection models. Three, an intrinsically disordered region represents a significant part of each protein and it has previously been shown that the Fg binding sites in Efb is located to its disordered region. A disordered protein is particularly suited for accommodating multiple ligands since several interacting motifs can fit in a short segment of the protein and these motifs can be overlapping because the segment has structural plasticity. Furthermore, amino acid sequence changes in a disordered protein segment are common since in these sections amino acid residue substitutions, deletions or additions can occur without interfering with a pre-existing structure. This tendency of sequence variations makes it particularly challenging to recognize interactive sequence motifs since these are often non-precise particularly if the motif is extended. The secreted staphylococcal Coa contains multiple copies of a Fg binding motif that functionally is similar to that previously identified in Efb's but that contains significant variations. Using an Alanine scanning approach, the residues in the motifs critical for Fg binding were identified. Comparing these critical residues in the Efb and the Coa motifs we find that these are largely conserved and that the Coa and Efb motifs are variants of the same motif. This Fg-binding motif has several unique characteristics. Firstly, the motif consists of 25-27 residues long peptide. This is unusual long compared to other known and well characterized interactive motifs. Secondly, along the length of the motif almost every other residue is important for Fg binding but exchange for similar residues is tolerated.

The Efb/Coa Fg-binding motif has been searched out in other eukaryotic and prokaryotic proteins including other staphylococcal SERAMs but so far without any hits. vWbp is structurally and functionally similar to Coa in the way that vWbp also activates prothrombin through the N-terminal D1D2 domain of the protein in a non-proteolytic manner and subsequently converts soluble Fg to insoluble fibrin clots. vWbp also binds Fg and this binding site was initially located to the C-terminal putatively disordered region but a recent study located the Fg-binding activity to the D1D2 domain of vWbp. No significant parts of the Efb/Coa Fg-binding motif is seen in any part of vWbp.

Efb is capable of escaping phagocytosis by formation of Fg containing shield surrounding the bacteria surface. This shield may protect the bacteria from clearance since opsonizing antibodies and phagocytes will not access the bacteria. In Efb dependent shield, Fg is brought to the surface of bacteria by Efb's ability to bind to microbial surface bound complement C3 through the C-terminal domains of the protein and recruits Fg through the N-terminal domain of the protein. Coa contains similar Efb's binding motif for Fg and therefore likely can form a Fg containing shield but Coa does not contain any known interaction with the bacterial surface. Therefore, the Fg shield may not be formed on the bacterial surface but surrounding the colony as seen in an abscess. In fact, Coa and Fg coincide in the core surrounding an abscess lesion and it is likely this core has a structural organization similar to the Fg protective shield formed by Efb. Also, some of the Fg binding MSCRAMMs can assemble a protective Fg containing shield around staphylococcal cells, a mechanism that could explain the virulence potential of proteins like ClfA.

It is likely that the interaction of staphylococcal proteins with Fg induces a conformational change in the host molecule which may in turn increase its tendency to aggregate. Efb binding to Fg results in a masking of the site in Fg recognized by the αMβ2/Mac-1 integrin. However, Efb effectively binds to a Fg variant where this site is mutated suggesting that this masking is not due to a direct competition for the site but possibly caused by an induced conformational change in Fg. Here experiments demonstrate that Coa harboring similar Fg binding motif can also inhibit THP-1 cell adherence through αMβ2/Mac-1 dependent mechanism suggesting that similar conformational changes can be induced by variants of the motif present in Efb and Coa. A more complete understanding of the molecular basis for the interaction of staphylococcal proteins interaction with Fg and the resulting Fg shield formed should lead to a better understanding of bacterial immune evasion strategies and may potential lead to novel strategies for the prevention and treatment of staphylococcal infections.

Secreted Fg binding proteins from *S. aureus* Coa and Efb are functionally related and locate Fg binding motifs to the intrinsically disordered section of the proteins. The residues in both the Efb and Coa Fg binding motifs were identified and it was concluded that these sequences are preserved and span a surprisingly long segment of the protein. Also, Coa contains multiples of this Fg-binding motif and define the functional register of the repeats in the disordered C-terminal region of Coa.

Bacterial Strains, Plasmids, and Culture Conditions—*Escherichia coli* XL-1 Blue was used as the host for plasmid cloning whereas *E. coli* BL21 or BL21(DE3)pLys were used for expression of GST- or His-tag fusion proteins. Chromosomal DNA from *S. aureus* strain Newman was used to amplify the Coagulase DNA sequence. *E. coli* XL-1 bule and BL21 containing plasmids were grown on LB media with ampicillin (100 µg/ml) and BL21(DE3)pLys containing plasmids were grown on LB media with ampicillin (100 µg/ml) and chloramphenicol (35 µg/ml).

Cloning of Coa construct—Chromosomal DNA from *S. aureus* strain Newman was used as template for all PCR reactions using the oligonucleotide primers described in supplement data. PCR products were digested with BamH I and Sal I and ligated into the pGEX-5x-1 vector or digested with BamHI and PstI and ligated into the pRSETA. Insertions were confirmed by DNA sequencing.

Expression and purification of recombinant Coa—Plasmids encoding N-terminal glutathione S-transferase (GST) or N-terminal 6×His-tagged Coa fusion proteins were expressed in either *E. coli* strain BL21 (GST tagged) or strain BL21(DE3)pLys (His-tagged). Bacteria were grown overnight at 37° C. in LB containing appropriate antibiotics as described above. The overnight cultures were diluted 1:20 into fresh LB medium and recombinant protein expression was induced with 0.2 mM IPTG for 2-3 hours. Bacteria were harvested by centrifugation and lysed using a French press. Soluble proteins were purified through glutathione-SEPHAROSE®-4B column or by Ni-chelating chromatography according to the manufacturer's manual. Purified proteins were dialysis into TBS and stored at −20° C. Protein concentrations were determined by the Bradford assay (Pierce). Recombinant Efb proteins were purified as previously described (12).

Enzyme-linked Immunosorbent Assay—96-well immulon 4HBX microtiter plates were coated with 0.25 µg/well full-length human Fibrinogen (diluted in PBS, Enzyme research) overnight at 4° C. unless otherwise indicated. After blocking the wells with 3% BSA/PBS, recombinant Coa proteins were added and the plates were incubated for one hour. Bound Coa proteins were detected through incubation with horseradish peroxidase (HRP)-conjugated anti-His antibodies (10,000×dilution) or HRP-conjugated anti-GST polyclonal antibodies (5000× dilution) for one hour and quantified after adding the substrate 0-phenylenediamine dihydrochloride by measuring the resulting absorbance at 450 nm in an ELISA microplate reader.

In the case of peptide inhibition assay, various concentration of Efb or Coa peptides were mixed with a fixed concentration of Coa-GST or Efb-GST fusion proteins (5-10 nM) in TBS and the bound GST fusion proteins were detected through incubation with HRP-conjugated rabbit anti-GST polyclonal antibodies (5000× dilution). All proteins were diluted in TBS containing 1% BSA and 0.05% TWEEN® 20 and the ELISA assays were carried out at room temperature.

Isothermal titration calorimetry—The interaction between Coa peptides and the soluble, isolated Fibrinogen-D fragment was further characterized by isothermal titration calorimetry (ITC) using a VP-ITC microcalorimeter. The Fibrinogen-D fragment used in these studies was generated by digesting full length Fibrinogen with plasmin for 4 h and fractionating the digestion products by gel filtration chromatography. The ITC cell contained 10 µM Fibrinogen-D fragments and the syringe contained 150-200 µM Coa peptides in TBS (25 mM Tris, 3.0 mM KCl and 140 mM NaCl, pH 7.4). All proteins were filtered through 0.22 µm membranes and degassed for 20 minutes before use. The titrations were performed at 27° C. using a single preliminary injection of 2 µl of Coa peptide followed by 30~40 injections of 5 µl with an injection speed of 0.5 µl s-1. Injections were spaced over 5-minute intervals at a stirring speed of 260 rpm. Raw titration data were fit to a one-site model of binding using MicroCal Origin version 5.0.

Cell adherence assay using cell lines—A monocytic cell line THP-1 cell stably expressing αMβ2 was maintained in RPMI1640 supplemented with 10% fetal bovine serum, 2 µM L-glutamine, 100 units/ml penicillin and 100 µg/ml streptomycin. Prior to use, cells were harvested by centrifuge, washed and suspended in RPMI 1640/1% human serum albumin. For cell adherence assays, 48-well plates were coated with 200 µl of Fibrinogen (10 µg/ml) overnight at 4° C. followed by 1 hour at 37° C. before blocking with 1% Polyvinylpyrrolidone (PVP 3600 kDa) for 45 minutes at 37° C. Subsequently, the cells were seeded $2 \times 10^5$/well in the presence or absence of Coa or Efb recombinant proteins or peptides and incubated at 37° C. for 25 minutes. Non-adherent cells were removed by washing gently three times with PBS/1% BSA. Adherent cells were quantitated with CyQuant kit according to the manufacturer's manual.

Bacterial strains, fluorescent labeling and supernatants—The present disclosure used the laboratory *S. aureus* strains Newman, SH1000, Reynolds and Wood 46 (with low expression of Protein A). The *S. aureus* strain KV27 and the *S. epidermidis* and *E. coli* strains were clinical isolates obtained within the UMCU. Targeted deletion (and complementation) of Efb in *S. aureus* Newman was described previously. All strains were cultured overnight on Tryptic Soy Blood Agar (BD) or Todd Hewitt Agar (with appropriate antibiotics) at 37° C. The capsule-expressing *S. aureus* strain Reynolds and its isogenic CP5-deficient mutant were a kind gift of Jean Lee (Harvard Medical School, Boston, USA). To optimize capsule expression, strain Reynolds was grown on Columbia Agar supplemented with 2% NaCl (CSA) for 24 hours at 37° C. For fluorescent labeling of strains, bacteria were resuspended in PBS and incubated with 0.5 mg/ml fluorescein isothiocyanate (FITC, Sigma) for 30 minutes on ice. Bacteria were washed twice with PBS, resuspended in RPMI medium 1o with HSA and stored at −20° C. until further use. For in vivo experiments, *S. aureus* Newman and the Efb mutant were transformed with the pCM29 plasmid (kindly provided by Alexander Horswill, University of Iowa) allowing constitutive expression of the superfolder green fluorescent protein (sGFP) via the sarAPI promoter. To isolate bacterial supernatants, WT and mutant strains were cultured overnight in Todd Hewitt Broth (THB) without antibiotics and subsequently sub-cultured in fresh THB for 4 hours or 20 hours. Cultures were centrifuged at 13,000 rpm and collected supernatants were stored at −20° C. until further use.

Protein expression and purification—Recombinant Efb proteins were generated in *E. coli* as described previously. Briefly, (parts of) the efb gene from *S. aureus* strain Newman (without the signal peptide) were amplified by PCR and ligated into either the pGEX-5x-1 vector or the pRSETB vector for N-terminal fusions with glutathione S-transferase (GST) or polyhistidine respectively. Mutations of the Fg and C3 binding domains were introduced in pGEX plasmids containing full-length GST-Efb as described previously. Recombinant proteins were expressed and purified according to the manufacturer's manual. In all studies where wild-type Efb was compared with mutants, GST-tagged Efb were used. Otherwise His-tagged Efb was used.

ELISA—Microtiter plates were coated with human C3b or Fg, blocked with 3% BSA-PBS, and incubated with 6 nM Efb for one hour at room temperature. Efb binding was detected using peroxidase-conjugated rabbit anti-GST polyclonal antibodies and quantified using 0-phenylenediamine dihydrochloride. To study formation of C3b-Efb-Fg complexes, C3b-coated plates were incubated with Efb for one hour at room temperature. After washing, human Fg (50 nM) was added and detected through incubation with peroxidase-conjugated anti-Fg antibodies.

Preparation of Fg-D fragments—D fragments of Fg were generated by digestion of human Fg (Enzyme research) with plasmin (Enzyme research, 10 µg/15 mg Fg) in TBS containing 10 mM $CaCl_2$) for 4 hours at 37° C. as described earlier with modifications. D fragments (85 kD) were purified by gel filtration on SEPHACRYL® S-200 and analyzed by SDS-PAGE.

Purification of human blood products—For preparation of plasma, venous blood from healthy volunteers was collected in glass vacutainers (BD) containing the anticoagulant lepirudin (50 µg/ml). To prepare serum, blood was collected in glass vacutainers (BD) without anticoagulant and allowed to clot for 15 minutes at room temperature. Plasma and serum were collected after centrifugation for 10 minutes at 4000 rpm at 4° C., pooled and subsequently stored at −80° C. Complement-inactivated serum was prepared by incubation of serum for 30 min at 56° C. Human neutrophils were isolated freshly from heparinized blood using the Ficoll-Histopaque gradient method and used on the same day.

Mice—C57BL/6 female mice were purchased from Harlan-Winkelmann and used in studies when they were between 8 and 10 weeks of age. They were housed in microisolator cages and given food and water ad libitum.

Phagocytosis assays—Whole blood phagocytosis. FITC-labeled *S. aureus* KV27 ($1\times10^8$/ml) was incubated with freshly isolated human lepirudin blood (50%) and buffer or Efb (0.5 µM) in RPMI-0.05% HSA for 25 minutes at 37° C. The reaction was stopped using FACS lysing solution; samples were washed with RPM1-0.05% HSA and analyzed by flow cytometry using a FACSCalibur (BD). Gating of cells occurred on basis of forward and side scatter; for each sample the fluorescence intensity of 10,000 gated neutrophils was measured. Phagocytosis was expressed as the percentage of neutrophils that became fluorescent.

Phagocytosis with purified neutrophils and plasma/serum—FITC-labeled bacteria ($5\times10^7$/ml) were mixed with human serum or plasma for 2 minutes at 37° C. in the presence or absence of Efb. Freshly isolated neutrophils ($5\times10^6$/ml) were added and phagocytosis was allowed for 15 minutes at 37° C. The reaction was stopped by formaldehyde fixation and analyzed by flow cytometry. Alternatively, phagocytosis mixtures were cytospinned on glass slides and stained using Giemsa-based Diff-Quick solution. To analyze killing, phagocytosis mixtures were not fixed but incubated for an additional 90 minutes before they were diluted into ice-cold water (pH 11) and incubated for 15 minutes on ice to enable neutrophil lysis. Viable bacteria were quantified by colony enumeration. For Fg supplementation, 5% serum was supplemented with 50-200 µg/ml human or mouse Fg (kindly provided by Dr. Jay L. Degen; purified from plasma of wild type and $Fg\gamma^{390-396A}$ mice). To analyze the influence of bacterial supernatants on phagocytosis, FITC-labeled *S. aureus* KV27 ($2.5\times10^7$ cfu) was pre-incubated with human serum for 30 min at 37° C. in Veronal Buffered Saline containing $Ca^{2+}$ and $Mg^{2+}$ ($VBS^{++}$). After washing in $VBS^{++}$-0.5% BSA, bacteria were incubated with (2-fold) diluted culture supernatants or purified Efb (250 nM) for 1 hour at 37° C. After washing, bacteria were incubated with purified Fg (60 µg/ml, Invitrogen) in RPMI-HSA for 1 hour at 37° C. and subsequently, neutrophils were added ($7.5\times10^3$ cells) and phagocytosis was allowed for 30 minutes at 37° C.

In vivo phagocytosis—*S. aureus* strain SH1000 was grown to mid-log phase, heat-inactivated for 60 minutes at 90° C., and fluorescently labeled with carboxyfluorescein. To induce infiltration of neutrophils within the peritoneal cavity, mice were intraperitoneally treated with 1 mg of carrageenan (Type IV1) 4 and 2 days prior to bacterial challenge. Subsequently, mice were intraperitoneally injected with 200 µl of a solution containing $10^8$ heat-inactivated carboxyfluorescein-labeled *S. aureus* SH1000 and Efb (1 µM). To compare WT and Δ Efb strains, mice were directly inoculated in the peritoneal cavity with 300 µl of GFP-expressing WT or Δ Efb *S. aureus* cultures grown to a late exponential phase. Mice were sacrificed 1 hour thereafter, and their peritoneum was lavaged with sterile PBS. Lavage samples were centrifuged, and pelleted cells were incubated with purified anti-CD32 antibodies to block the FcR, followed by PE-conjugated anti-mouse Gr-1 antibodies. Cells were washed and quenched with trypan blue (2 mg/ml). Samples were immediately subjected to flow-cytometric analysis using a FACScan. Neutrophils were gated according to their expression of Gr-1 antigen (FL2). Phagocytosis was expressed as the percentage of neutrophils that became fluorescent.

Alternative pathway hemolysis assay—Human serum (5%) was incubated with buffer or Efb proteins (1 µM) in HEPES-MgEGTA (20 mM HEPES, 5 mM MgCl$_2$, 10 mM EGTA) for 15 minutes at RT. Rabbit erythrocytes were added and incubated for 60 min at 37° C. Mixtures were centrifuged and hemolysis was determined by measuring the absorbance of supernatants at 405 nm.

Immunoblotting—To analyze C3b deposition on the bacterial surface, S. aureus strain Wood46 ($3\times10^8$/ml) was incubated with 5% human plasma in the presence of Efb (0.5 µM), EDTA (5 mM) or buffer (HEPES$^{++}$; 20 nM HEPES, 5 mM CaCl$_2$), 2.5 mM MgCl$_2$, pH 7.4) for 30 min at 37° C. shaking at 1100 rpm. Bacteria were washed twice with PBS-0.1% BSA and boiled in Laemmli sample buffer containing Dithiothreitol. Samples were subjected to SDS-PAGE and subsequently transferred to a nitrocellulose membrane. C3b was detected using a peroxidase-labeled polyclonal anti-human C3 antibody and developed using Enhanced Chemiluminescence. To quantify Efb in bacterial supernatants, His-Efb and supernatants were run together on an SDS-PAGE gel. After transfer, blots were developed using a polyclonal sheep anti-Efb antibody, peroxidase-labeled donkey anti-sheep antibodies (Fluka Analytical) and ECL.

Flow cytometry assays with S. aureus—S. aureus strain Wood46 ($3\times10^8$/ml) was pre-incubated with human serum for 30 min at 37° C. in VBS$^{++}$ buffer, washed with VBS$^{++}$-0.5% BSA and incubated with Efb (0.5 µM) or 2-fold diluted culture supernatants for 1 hour at 37° C. shaking. After another washing step, bacteria were incubated with ALEXA FLUOR™ 488 conjugated Fg (60 µg/ml, Invitrogen) for 1 hour at 37° C. shaking. Washed bacteria were analyzed by flow cytometry using a FACSCalibur (BD). Bacteria were gated on the basis of forward and side scatter properties and fluorescence of 10,000 bacteria was analyzed. Alternatively, pre-opsonized bacteria were incubated with Efb (0.5 µM) and/or unlabeled Fg (200 µg/ml) for 1 hour at 37° C. shaking. Washed bacteria were incubated with soluble rCR1 (10 µg/ml), FITC-labeled F(ab')$_2$ anti-human C3 antibody or anti-human IgG antibody for 30 min at 37° C. CR1 was detected using PE-labeled anti-CD35 antibodies; the IgG antibody was detected using goat-anti-mouse PE antibodies. Capsule expression on strain Reynolds was analyzed by incubating bacteria with polyclonal anti-CP5 rabbit serum and Phycoerythrin (PE)-conjugated goat anti-rabbit antibody.

Confocal microscopy—Samples were transferred to glass slides and air-dried. Membrane dye FM 5-95 was added and slides were covered with a coverslip. Confocal images were obtained using a Leica TCS SP5 inverted microscope equipped with a HCX PL APO 406/0.85 objective.

Transmission Electron Microscopy—S. aureus strain Wood 46 ($3\times10^8$) was incubated with human plasma (10%) in the presence or absence of Efb (0.5 µM) in HEPES' for 30 minutes at 37° C., washed once with PBS-1% BSA and adsorbed to 100 mesh hexagonal Formvar-carbon coated copper grids. Samples were contrasted with 0.4% uranyl acetate (pH 4.0) and 1.8% methylcellulose and analysed in a JEOL 1010 transmission electron microscope at 80 kV.

Recombinant proteins—The recombinant P163 protein was based upon the Scl2.28 sequence from S. pyogenes with the DNA codon optimized for E. coli expression. A hexa-histidine tag was introduced at the N-terminus for use in purification. The GFPGER-containing SEQ ID NO:230 variant described in Cosgriff-Hernandez, et al. and referred to as DC2 was utilized in these studies. The fibrinogen-binding DC2 variant (DC2-Fg) was generated using overlap extension polymerase chain reaction (PCR) with primers from Integrated DNA Technologies. The Fg binding motif Efb-O was inserted after position 301 Gln in DC2 shown in FIG. 16A. FIG. 16A is a Schematic representation of DC2-Fg with fibrinogen (Fg) binding motif Efb-O. The inserted Efb-O amino acid sequence is SEQ ID NO:1 KYLKFKH-DYN ILEFNDGTFE YGARPQFNKP A. The insertion was verified by sequencing (GENEWIZ, South Plainfield, N.J.). Recombinant proteins were expressed in E. coli BL21 (Novagen). Purification was carried out by affinity chromatography on a StrepTrap HP column and subsequent dialysis against 20 mM acetic acid (regenerated cellulose, MWCO=12-14 kDa). Protein purity was assessed by sodium dodecyl sulfate polyacrylamide gel electrophoresis (SDS-PAGE) followed by COOMASSIE® Blue staining. Protein concentrations were measured using the DC protein assay. Circular dichroism (CD) was utilized to confirm triple helix retention with the insertion as previously described.

Integrin interactions with DC2-Fg—All cell culture supplies were purchased from Life Technologies and used as received unless otherwise noted. To assess retention of integrin binding in DC2-Fg, adhesion of (i) C2C12 cells, which do not natively express integrin α1 or α2 subunits, (ii) C2C12 cells modified to stably express human integrin α1 subunits (C2C12-α1), and (iii) C2C12 cells modified to stably express human integrin α2 subunits (C2C12-α2) was measured. Mouse myoblast C2C12, C2C12-α1, and C2C12-α2 cells were cultured in Dulbecco's modified Eagle's medium (DMEM) with 10 vol % fetal bovine serum (FBS) and 1 vol % penicillin-streptomycin, 1 mg ml$^{-1}$ geneticin, or 10 µg ml$^{-1}$ puromycin, respectively. To assess C2C12 cell adhesion, 48 well tissue culture polystyrene (TCPS) plates were coated with 10 µg of DC1 (negative control—no integrin binding sites), DC2, DC2-Fg, or collagen type I (positive control) overnight at 4° C. Proteins were coated in triplicate for each cell type. Wells were blocked with 4 wt % bovine serum albumin (BSA) in PBS for 1 hour at room temperature and rinsed with sterile PBS. Cells were adapted to serum-free media (DMEM with 1 mM CaCl$_2$, 1 mM MgCl$_2$, and appropriate antibiotic) for 12 hours prior to trypsinization and seeding at 5,000 cells cm$^{-1}$. After 1 hour, cells were washed three times with warm PBS and lysed with 1% TRITON™-X 100 for 30 minutes at 37° C. Lysates from samples and from known standards were transferred to a 96 well plate, and cell numbers were measured with the CYTOTOX 96® NON-RADIOACTIVE CYTOTOXICITY ASSAY. Briefly, 50 µl of samples were incubated with 50 µl of substrate solution for 30 min at room temperature. Then, 50 µl of stop solution was added to each well, and the absorbance was read at 490 nm. Cell numbers were quantified using standards of known cell numbers for each cell line.

Solid phase binding assay-: Microtiter wells were coated with 1 µg of DC2, DC2-Fg, or Efb overnight at 4° C. to assess fibrinogen adhesion to DC proteins. Coated wells were blocked with 4 wt % BSA in PBS for 1 hour at room temperature. Fibrinogen was added to each protein-coated well in a serial dilution from 100 to 0 µg/well (0.3 to 0 µM). After 1 hour of incubation at room temperature, a sheep anti-fibrinogen antibody was applied to the wells (1:1000 dilution) for 1 hour at room temperature. An HRP-labelled secondary antibody to sheep was applied to the wells for 1 hour at room temperature, and SIGMAFAST™ OPD was utilized to detect bound fibrinogen via an absorbance reading at 450 nm on a THERMOMAX™ plate reader. Studies were performed in triplicate, and plates were washed three times between each step with 200 μl of PBS with 0.1 vol % TWEEN® 20.

FIG. 16B is an image of a circular dichroism (CD) spectra of DC2 and DC2-Fg. Peak at 220 nm is indicative of triple helix. DC2-Fg was successfully expressed and purified. The CD spectrum of DC2-Fg indicates that the protein retains the triple helical conformation of DC2 with the insertion, as demonstrated by the positive peak at ~220 nm. FIG. 16C is plot of the integrin α1 and α2 subunit expressing C2C12 cell adhesion to DC1 (no integrin binding site), DC2 (binding site for integrins α1 and α2), DC2-FN (DC2 with fibrinogen binding site), and collagen (multiple binding sites for integrins α1 and α2). Retention of integrin binding with the Fg-binding insertion was assessed using C2C12 cells that express integrin α1 or α2 subunits. DC2 demonstrated an increase in C2C12-α1 and C2C12-α2 adhesion relative to DC1 (non-integrin binding negative control), as expected. The insertion of the Fg-binding motif, Efb-O, did not interfere with integrin binding, as demonstrated by C2C12-α1 and C2C12-α2 adhesion. In fact, DC2-Fg had significantly increased C2C12-α1 and C2C12-α2 adhesion relative to DC2 ($p<0.05$). This could be due to cell production of fibrinogen and subsequent binding to the Fg-binding motif in addition to interacting with the integrin-binding site in DC2-Fg. FIG. 16D is a graph showing fibrinogen binding to DC2, DC2-Fg, and Efb, as determined by solid phase binding assay. Fibrinogen interactions with DC2 and DC2-Fg were assessed using a solid phase binding assay. DC2 exhibited minimal to no fibrinogen binding, with no saturation in binding within the tested range of concentrations. Insertion of the Fg-binding motif, Efb-O, provided a large increase in fibrinogen binding, with an apparent $K_D$ of ~10 nM. This binding affinity approached that of Fg to Efb-O, with an apparent $K_D$ of ~1 nM. These results indicate that the Efb-based fibrinogen binding site, Efb-O, was successfully inserted into DC2 to provide a triple helical protein with controlled integrin binding and fibrinogen interactions. Statistical analyses were performed using GRAPHPAD PRISM® 4.0 package and the differences between groups were analyzed for significance using the two-tailed Student's t-test.

FIG. 17 shows the binding of Coa and Efb fragments by FBE5 antibodies. The 11 monoclonal antibodies selected against Coa-$C_{311-636}$ were tested on different portions of the C-terminal part of Coagulase, namely Coa-$F_{311-505}$, Coa-$R0_{474-505}$ and Coa-$R_{506-636}$, and different fragments of Efb, namely Efb-$N_{30-105}$, Efb-$A_{30-67}$ and Efb-$O_{68-98}$. These proteins were immobilized (200 ng/well) and probed with the indicated antibodies at a fixed concentration (0.5 μg/ml) in a solid-phase binding assay. Binding was clearly observed for all of them and it is noticeable that the antibodies displayed variable apparent affinities to the different Efb and Coa fragments. None of the FBE5 antibodies bound to Coa-$R_{506-636}$.

Antibody generation and scFv-Fc production—Antibodies against Coa were selected in scFv-format from the human naïve antibody gene libraries HAL9 and HAL10 (Kügler et al., 2015). The selection and screening was performed as described before (Russo et al., 2018a). In brief, for antibody selection, scFv phage from HAL9 and HAL10 were mixed and incubated on Coa immobilized in Costar High Binding microtiter plates (SIGMA-ALDRICH® Chemie GmbH, Munich, Germany). Panning was performed at room temperature. After three rounds of panning, monoclonal soluble scFv were produced and screened for Coa binding by antigen-ELISA. DNA of binding candidates was isolated and sequenced. The unique scFv sequences were recloned into pCSE2.6-hIgG1-Fc-XP (Russo et al., 2018b) using NcoI/NotI (NEB) for mammalian production as scFv-Fc, an IgG-like antibody format. The production in HEK293-6E cells and subsequent protein A purification was performed as described before (Jager et al., 2013).

FIG. 18 shows the dose-dependent binding of Coa fragments by FBE5 antibodies. The 11 monoclonal antibodies selected against Coa-$C_{311-636}$ were titrated on different portions of the C-terminal part of Coagulase, namely Coa-$C_{311-636}$, Coa-$F_{311-505}$, and Coa-$R0_{474-505}$. Recombinant proteins Coa-$C_{311-636}$, Coa-$F_{311-505}$, and Coa-$R0_{474-505}$ were immobilized (200 ng/well) and probed with the selected antibodies in a solid-phase binding assay. Dose dependent binding was clearly observed for all of them and it is noticeable that the antibodies display variable apparent affinities to the different proteins. An irrelevant isotype-matched antibody (isotype control) was tested. As shown, no binding was detectable for this latter antibody.

FIG. 19 is a table that shows the apparent $K_d$ of anti-CoaC mAbs to Coa fragments determined through $EC_{50}$ calculation in ELISA. Apparent affinity values were generated through analysis of the half maximum binding in ELISA, using GRAPHPAD PRISM® Version 6.01. In most cases, values in the range of $10^{-9}$-$10^{-10}$ M were obtained for most antibodies against all three Coa fragments tested (Coa-$C_{311-636}$, Coa-$F_{311-505}$. Coa-$R0_{474-505}$). FBE5-F11 resulted to show the highest affinity to all the three proteins tested and FBE5-C8, conversely was the weakest binder of the three fragments of Coa tested.

FIG. 20 shows the dose-dependent binding of Efb fragments by FBE5 antibodies. The 11 monoclonal antibodies selected against Coa-$C_{311-636}$ were titrated on different portions of the N-terminal part of Efb protein, that has sequence and functional homology to Coagulase. Immobilized (200 ng/well) and probed for recognition in a solid-phase binding assay are Efb-$N_{30-105}$, Efb-$A_{30-67}$ and Efb-$O_{68-98}$. These proteins were probed with different quantities of the selected antibodies. Dose dependent binding is observed for all of them and it is noticeable that the antibodies display variable apparent affinities to the different proteins. An irrelevant isotype-matched antibody (isotype control) was tested. As shown, no binding was detectable for this latter antibody.

FIG. 21 is a table with the apparent $K_d$ of anti-CoaC mAbs to Efb fragments determined through $EC_{50}$ calculation in ELISA. Apparent affinity values were generated through analysis of the half maximum binding in ELISA, using GRAPHPAD PRISM® Version 6.01. In most cases, values in the range of $10^{-8}$-$10^{-9}$ M were obtained for most antibodies against all three Efb fragments tested (namely Efb-$N_{30-105}$, Efb-$A_{30-67}$ and Efb-$O_{68-98}$). FBE5-F11 was the only exception, since it displayed apparent affinities in the range of $10^{-10}$ M against all three Efb fragments. Weak binders, FBE5-C1, FBE5-C8, FBE5-E5, showed very modest binding and in some cases an estimation of apparent affinities was not possible (ND, not determinable).

FIG. 22 shows the FBE5 mAbs that efficiently inhibit binding to Fg of Coa and Efb in a dose-dependent manner. To assess the inhibitory activity of anti-Coa scFv-Fc antibodies, 0.5 μg/well of human Fg was immobilized at 4° C. overnight in 50 mM Carbonate Buffer, pH 9.6. Indicated amounts (0, 0.5, 5, and 50 μg/ml) of scFv-Fcs were preincubated for 1 hour with a constant concentration of Coa or Efb fragments. Specifically, Coa-F, Coa-R0, Efb-N and Efb-O were at a fixed concentration of 10 nM; whereas Efb-A was at 750 nM. Fg-binding activity of each protein alone was also checked (no mAb control—0 µg/ml). The Fg-coated plate was blocked with 2% BSA-PBST and washed with PBST. The pre-incubated mixture of Coa/Efb and anti-Coa scFv-Fc was transferred on the Fg-coated plate. Residual bound Coa and Efb fragments were detected with HRP-conjugated (HorseRadish Peroxidase-conjugated) α-GST-tag antibody, except for Efb-N, where an HRP-conjugated α-HIS-tag was used. Binding of Coa and Efb fragments to Fg (no mAb control) was set to 100% and residual binding to Fg of Coa and Efb fragments in the presence of different concentrations of antibodies was calculated and represented. FBE5-A12, FBE5-D10, FBE5-F9 and FBE5-F11 did show a dose dependent inhibition of all proteins tested. In particular FBE5-F11 showed a marked inhibition against all fragments of Coa and Efb. FBE5-A12, FBE5-D10 and FBE5-F9 showed a clear inhibition of CoaF, CoaRO and EfbA, being less efficient in inhibiting EfbN and EfbO.

Figure 23:
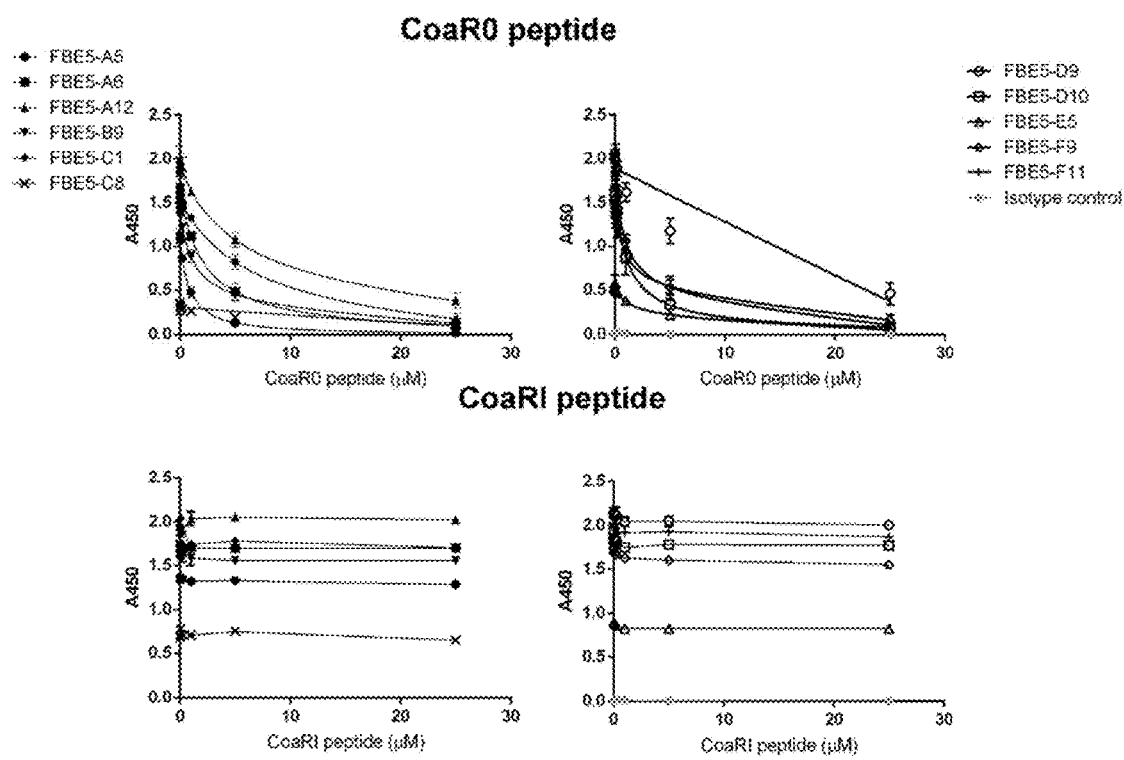
FIG. 23 shows that Peptide CoaRO, but not peptide CoaRI, inhibit FBE5 mAbs binding to CoaC. To investigate if FBE5 mAbs could be inhibited by CoaRO and CoaRI peptides, CoaC (200 ng/well) was immobilized at 4° C.

FIG. 23 shows that Peptide CoaRO, but not peptide CoaRI, inhibits FBE 5 mAbs binding to CoaC. To investigate if FBE5 mAbs could be inhibited by CoaRO and CoaRI peptides, CoaC (200 ng/well) was immobilized at 4° C. overnight in 50 mM Carbonate Buffer, pH 9.6. A fixed concentration of mAbs (0.5 µg/ml) was added to the wells along with indicated amounts of CoaRO and CoaRI peptides. Incubation for 1 hour at room temperature and 250 rpm shaking followed. After washing, towels were incubated with a polyclonal α-human IgG HRP-conjugated Ab. An irrelevant, isotype-matched scFv-Fc served as a control (FBE3-X). All FBE5 antibodies were inhibited by peptide CoaRO in a fashion dependent of the peptide concentration. Instead, peptide CoaRI was unable to affect FBE5 mAbs binding to CoaC.

FIG. 24 shows the dose-dependent binding of Coa and Efb fragments by LIG40 antibodies. The 2 monoclonal antibodies (LIG40-A11 and LIG40-D8) selected against Coa-$R_{506-636}$ were titrated on different portions of the N-terminal part of Efb protein (Efb-$N_{30-105}$, Efb-$A_{30-67}$ and Efb-$O_{68-98}$), that, as reported in the parent patent, has sequence and functional homology to Coagulase. As well, binding was tested against Coa fragments, namely Coa-$C_{311-636}$, Coa-$F_{311-505}$, Coa-$RO_{474-505}$ and Coa-$R_{505-636}$. Recombinant proteins Efb-$N_{30-105}$, Efb-$A_{30-67}$, Efb-$O_{68-98}$, Coa-$C_{311-636}$, Coa-$F_{311-505}$, Coa-$RO_{474-505}$ and Coa-$R_{506-636}$ were immobilized (200 ng/well) in a 96 well plate and probed for recognition in a solid-phase binding assay with different quantities of LIG40 antibodies. Dose dependent binding was observed for all of them. These 2 antibodies bound only Coa fragments. LIG40-A11 recognized specifically Coa-$R_{506-636}$ and, reasonably, Coa-$C_{311-636}$. even though the latter with lower apparent affinity. No binding to all other proteins has been detectable for LIG40-A11. LIG40-D8 also bound Coa-$R_{506-636}$ and Coa-$C_{311-636}$ but also binding of Coa-$F_{311-505}$ and Coa-$RO_{474-505}$ was detected to a minor extent. Both antibodies did not show binding to BSA and an irrelevant isotype-matched antibody (isotype control) did not show non-specific binding to the immobilized proteins.

FIG. 25 shows that LIG40-A11 mAb inhibits binding to Fg of Coa-$C_{311-636}$ and Coa-$R_{506-636}$ in a dose-dependent manner. To assess the inhibitory activity of anti-CoaR scFv-Fc antibody, 0.5 µg/well of human Fg was immobilized at 4° C. overnight in 50 mM Carbonate Buffer, pH 9.6. Indicated amounts of scFv-Fc were pre-incubated for 1 hour with a constant concentration of CoaC or CoaR (10 nM). Fg-binding activity of each protein at 10 nM in the absence of antibody was also checked, and referred as CTRL+(CoaC) and CTRL+(CoaR) in the figure (no mAb control—CTRL+). The Fg-coated plate was blocked with 2% BSA-PBST and washed with PBST. The pre-incubated mixture of CoaC/CoaR and anti-Coa scFv-Fc was transferred on the Fg-coated plate. Residual bound CoaC and CoaR was detected with an HRP-conjugated α-GST-tag antibody. Binding of 10 mM CoaC and CoaR to Fg in the absence of antibody, referred as CTRL+(CoaC) and CTRL+(CoaR) in the figure (no mAb control—CTRL+) was set to 100% and residual binding to Fg of CoaC and CoaR in the presence of different concentrations of antibodies was calculated and represented. LIG40-A11 showed a dose-dependent inhibition of CoaC and CoaR, being more potent against CoaR.

FIG. 26 shows that peptides CoaRO and CoaRI differentially inhibit LIG40 mAbs binding to CoaC and CoaR. To investigate if LIG40 mAbs could be inhibited by CoaRO and CoaRI peptides, CoaC and CoaR (200 ng/well) was immobilized at 4° C. overnight in 50 mM Carbonate Buffer, pH 9.6. A fixed concentration of mAbs (0.5 µg/ml) was added to the wells along with, indicated amounts of CoaRO and CoaRI peptides. Incubation for 1 hour, room temperature, 250 rpm shaking followed. After washing, towels were incubated with polyclonal α-human IgG HRP-conjugated Ab. Surprisingly, LIG40-A11 and LIG40-D8 behaved differently in the presence of the two peptides. First, to achieve appreciable inhibition high concentration of peptides needed to be used (above 100 µM). Secondly and most importantly, LIG40-A11 was inhibited only by CoaRI peptide, both when mAb binding was tested against CoaC and CoaR. In symmetrical opposite way, LIG40-D8 was only impaired in its binding activity by CoaRO peptide, suggesting that the differential role of the two repeats.

FIG. 27 is a table that shows the apparent $K_d$ of anti-Coa-$R_{506-636}$ mAbs to Coa fragments determined through $EC_{50}$ calculation in ELISA. Apparent affinity values were generated through analysis of the half maximum binding in ELISA, using GRAPHPAD PRISM® Version 6.01. For both antibodies, values in the range of $10^{-10}$-$10^{-11}$ M were obtained. LIG40-A11 showed the highest apparent affinity for CoaR ($7.05 \times 10^{-11}$ M) whereas LIG40-D8 was the one that showed the highest half-maximum binding to CoaC ($9.39 \times 10^{-11}$ M). Only LIG40-D8 showed minor binding to CoaRO and CoaF, instead for LIG40-A11 there was no detectable binding (apparent affinity not determinable, ND).

| FBE5 antibodies, raised against COA-C$_{(311-636)}$, shown in scFv-Fc format | | | | |
|---|---|---|---|---|
| Antibody name | VH amino acid sequence | SEQ ID NO | VL amino acid sequence | SEQ ID NO |
| FBE5-A5 | EVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKAGPDSYGYGMDVWGQGT TVTVSS | VH: 71 CDR1: 131 CDR2: 135 CDR3: 139 | QSVLTQPPSASGTPGQRVTISCSGSSSN IGSNTVNWYQQLPGTAPKLLIYSNNQRPS GVPDRFSGSKSGTSASLAISGLQSEDEAD YYCAAWDDSLNGVVFGGGTKLTVL | VL: 101 CDR1: 166 CDR2: 185 CDR3: 202 |

-continued

FBE5 antibodies, raised against COA-C(311-636), shown in scFv-Fc format

| Antibody name | VH amino acid sequence | SEQ ID NO | VL amino acid sequence | SEQ ID NO |
|---|---|---|---|---|
| FBE5-A6 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKAGDDDYGHYFDYWGQGTL VTVSS | VH: 72<br>CDR1: 131<br>CDR2: 135<br>CDR3: 140 | QAGLTQPPSASGTPGQGVTISCSGSSSNI GSNTVNWYQQLPGTAPKLLIYSNNQRPSG VPDRFSGSKSGTSASLAISGLQSEDEADY YCAANDDSLNGVVFGGGTKLTVL | VL: 102<br>CDR1: 166<br>CDR2: 185<br>CDR3: 202 |
| FBE5-A12 | QVQLVESGGGVVQPGRSLRLSCAASGFTF SSYGMHWVRQAPGKGLEWVAVISYDGSNK YYADSVKGRFTISRDNSKNTLYLQMNSLR GEDTAVYYCAREGGWEPNGLDYWGQGTLV TVSS | VH: 73<br>CDR1: 131<br>CDR2: 135<br>CDR3: 141 | QAVLTQPPSASGTPGQRVTISCSGSDFNV GTNYVNWYQQLPGSAPKLLIYRNNQRPS GVPDRFSGSKSGTSATLGITGLQTGDEAD YYCGTWDSSLSAEFGGGTKLTVL | VL: 103<br>CDR1: 167<br>CDR2: 186<br>CDR3: 203 |
| FBE5-B9 | EVQLVESRGGVVQPGRSLRLSCAASGFTF SSYGMHWVRQAPGRGLEWVAVISYDGSNK YYADSVKGRFTISRDNSKNTLYLQMNGLR SDDTAVYYCARGGDDYGDYFDYWGQGTLV TVSS | VH: 74<br>CDR1: 131<br>CDR2: 135<br>CDR3: 142 | QSVLTQPPSVSAAPGQKVTISCSGSSSNI GNNYVSWYQQLPGTAPKLLIYDNNKRPSG IPDRFSGSKSGTSATLGITGLQTGDEADY YCGTWDSSLSAAVFGGGTKLTVL | VL: 104<br>CDR1: 168<br>CDR2: 187<br>CDR3: 204 |
| FBE5-C1 | EVQLVETRGGVVQPGRSLRLSCAASGFTF SSYGMHWVRQAPGKGLEWVAVISYDGSNK YYADSVKGRFTISRDNSKNTLYLQMNSLR AEDTAVYYCAREGTYYYDSSGYYEGGFDY WGQGTLVTVSS | VH: 75<br>CDR1: 131<br>CDR2: 135<br>CDR3: 143 | QSVLTQPPSASGTPGQRVTISCSGSSSNI GSGPVNWYQQLPGTAPKLLIYSDTRRPSG IPDRLSGSKSGTSASLGISGLQSEDEADY YCAANDDSLNGYAFGSGTKVTVL | VL: 105<br>CDR1: 169<br>CDR2: 188<br>CDR3: 205 |
| FBE5-C8 | QMQLVQSGGGVVQPGRSLRLSCAASGFIF SNYGMHWVRQAPGKGLEWVAVISYDGSNK YYADSVKGRFTISRDNSKNTLYLQMDSLR AEDTAVYYC AREGVGGDYGDLPTGPYYYGMDV WGQGTTVTVSS | VH: 76<br>CDR1: 132<br>CDR2: 135<br>CDR3: 144 | QSVLTQPPSVSAAPGQKVTISCSGSSSNI GNNSVSWYQQLPGTAPKLLIYDNNKRPSG IPDRFSGSKSGTSATLGITGLQTGDEADY YCETWDSSLSAVVFGGGTKLTVL | VL: 106<br>CDR1:<br>CDR2:<br>CDR3: |
| FBE5-D9 | QVQLVESGGGVVQPGRSLRLSCAASGFTF SSYGMHWVRQAPGKGLEWVAVISYDGSNK YYADSVKGRFTISRDNSKNTLYLQMNSLR AEDTAVYYCKNQEWLVPGYWGQGLVTV SS | VH: 77<br>CDR1: 131<br>CDR2: 135<br>CDR3: 145 | QSALTQPASVSGSPGQSITISCTGTSSDV GGYNYVSWYQQHPGKAPKLMIYDVSNRPS GVSNRFSGSKSGNTASLTISGLQAEDEAD YYCSSYTSSSTLVFGGGTKLTVL | VL: 107<br>CDR1: 171<br>CDR2: 189<br>CDR3: 207 |
| FBE5-D10 | QVQLVQSGGGVVQPGRSLRLSCAASGFTF SNYGMHWVRQAPGKGLEWVAVISYDGSNK YYADSVKGRFTISRDNSKNTLYLQMNSLR AEDTAVYYCAKDSREQWLAHWGQGTLVTV SS | VH: 78<br>CDR1: 133<br>CDR2: 135<br>CDR3: 146 | QSVLTQPPSASGTPGQRVTISCSASSSNI GSNTVNWYQQLPGTAPKLLIYSNNQRPSG VPDRFSGSRSGTSASLAISGLQSEDEADY YCAANDDSLNALVFGGGTKLTVL | VL: 108<br>CDR1: 166<br>CDR2: 185<br>CDR3: 208 |
| FBE5-E5 | QMQLVQSGGGVVQPGRSLRLSCAASGFTF SSYGMHWVRQAPGKGLEWVAVISYDGSNK YYADSVKGRFTISRDNSKNTLYLQMNSLR GEDTAVYYCAREGGWEPNGLDYWGQGTLV TVSS | VH: 79<br>CDR1: 131<br>CDR2: 135<br>CDR3: 141 | QSVLTQPPSVSAAPGQKVTISCSGSSSNI GNNYVSWYQQLPGTAPKLLIYDNNKRPSG IPDRFSGSKSGTSATLGITGLQTGDEADY YCGTWDSSLSAEVFGGGTKLTVL | VL: 109<br>CDR1: 168<br>CDR2: 187<br>CDR3: 203 |
| FBE5-F9 | QMQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKEGDGDYGGVLDYWGQGTL VTVSS | VH: 80<br>CDR1: 131<br>CDR2: 135<br>CDR3: 147 | QSVLTQPPSVSAAPGQKVTISCSGSSSNI EKNYVSWYQQLPGTAPKLLIYDNNKRPSG IPDRFSGSKSGTSATLGITGLQTGDEADY YCGTWDSSLSAVVFGGGTKLTVL | VL: 110<br>CDR1: 172<br>CDR2: 187<br>CDR3: 209 |
| FBE5-F11 | QVQLQESGGGVVQPGRSLRLSCAASGFTF SSYGMHWVRQAPGKGLEWVAVISYDGSNK YYADSVKGRFTISRDNSKNTLYLQMNSLR AEDTAVYYCAKDLASSGFDYWGQGTLVTV SS | VH: 81<br>CDR1: 131<br>CDR2: 135<br>CDR3: 148 | QSVLTQPPSVSAAPGQKVTISCSGSSSNI GNNYVSWYQQLPGTAPKLLIYDNNKRPSG IPDRFSGSKSGTSATLGITGLQTGDEADY YCGTWDSSLSAEVFGGGTKLTVL | VL: 111<br>CDR1: 168<br>CDR2: 187<br>CDR3: 203 |
| FBE5-A7 | QVQLVESGGGVVQPGRSLRLSCAASGFTF SSYGMHWVRQAPGKGLEWVAVISYDGSNK YYADSVKGRFTISRDNSKNTLYLQMNSLR AEDTAVYYCAKGSYDGGRAFDYWGQGTL VTVSS | VH: 82<br>CDR1: 131<br>CDR2: 135<br>CDR3: 149 | QPVLTQSSASGTPGQRVTISCSGSSSNI GSNTVNWYQQVPGTAPKLLIYGNNQRPSG VPDRFSGSKSGTSASLAISGLQSEDEADY YCAANDDSLNGVVFGGGTKLTVL | VL: 112<br>CDR1: 166<br>CDR2: 190<br>CDR3: 202 |
| FBE5-A11 | QVQLVESGGGVVQPGRSLRLSCAASGFTF SSYGMHWVRQAPGKGLEWVAVISYDGSNK YYADSVKGRFTISRDNSKNTLYLQMNSLR AEDTAVYYCAKEIEWDGAFDNWGQGTMVT VSS | VH: 83<br>CDR1: 131<br>CDR2: 135<br>CDR3: 150 | QTVVTQEPSVSAAPGQKVTISCSGSSSNI GNNYVSWYQQLPGTAPKLLIYDNNRRPSG IPDRFSGSKSGTSATLGITGLQTGDEADY YCGTWDSSLSAVVFGGGTKLTVL | VL: 113<br>CDR1: 168<br>CDR2: 187<br>CDR3: 209 |

| FBE5 antibodies, raised against COA-C(311-636), shown in scFv-Fc format ||||
|---|---|---|---|
| Antibody name | VH amino acid sequence | SEQ ID NO | VL amino acid sequence | SEQ ID NO |
| FBE5-B2 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCATEPSRSGTGYWGQGTLVTV SS | VH: 84<br>CDR1: 131<br>CDR2: 135<br>CDR3: 151 | QSVLTQPPSASGTPGQRVTISCSGSSSNI GSNTVNWYQQLPGTAPRLVIHGDNRRPSG VSGRFSGSKSGASASLAISGLQSEDEADY YCTVWDSDLNGVVFGGGTRLTVL | VL: 114<br>CDR1: 166<br>CDR2: 191<br>CDR3: 210 |
| FBE5-C5 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKEAPGATGAFDIWGQGTMV TVSS | VH: 85<br>CDR1: 131<br>CDR2: 135<br>CDR3: 152 | QSVLTQPPSVAASGQKVTISCSGSSSNI GNNYVSWYQQLPGTAPKLLIYDNNKRPSG IPDRFSGSKSGTSATLGITGLQTGDEADY YCGTWDSSLSAEVFGGGTKLTVL | VL: 115<br>CDR1: 168<br>CDR2: 187<br>CDR3: 203 |
| FBE5-D1 | QVQLQESGGGVVQPGRSLRLSCAASGFTF SSYGMHWVRQAPGKGLEWVAVISYDGSNK YYADSVKGRFTISRDNSKNTLYLQMNSLR AEDTAVYYCAKEGDGGSGMDVWGQGTTVT VSS | VH: 86<br>CDR1: 131<br>CDR2: 135<br>CDR3: 153 | QSVLTQPPSVSEAPGQRVTISCTGSSSNI GAGYDVHWYQQLPGTAPKLLIYGNSNRPS GVPDRFSGSKSGTSASLAISGLRSEDEAD YYCAAWDDSLSGREVFGGGTKLTVL | VL: 116<br>CDR1: 173<br>CDR2: 192<br>CDR3: 211 |
| FBE5-D4 | QMQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCARVGESEGAFDIWGQGTMVT VSS | VH: 87<br>CDR1: 131<br>CDR2: 135<br>CDR3: 154 | QPVLTQPPSVSVAPRQTARITCGGNNIGR KTVHWYQQKPGQAPVLVVYDDSDRPSGIP ERFSGSNSGNTATLIISGVEAGDEADYYC QVWDSSSDHVIFGGGTKVTVL | VL: 117<br>CDR1: 174<br>CDR2: 193<br>CDR3: 212 |
| FBE5-E3 | QVQLVESGGGVVQPGRSLRLSCAASGFTF SSYGMHWVRQAPGKGLEWVAVISYDGSNK YYADSVKGRFTISRDNSKNTLYLQMNSLR AEDTAVYYCARVGYGDYGVLADYWGQGTL VTVSS | VH: 88<br>CDR1: 1131<br>CDR2: 135<br>CDR3: 155 | QSVLTQPPSVSEAPRQRVTISCSGSSSNI GNNAVNWYQHLPGKAPKLLIEHDDHLPSG VSDRFSGSKSGTSASLAISGLQPEDEADY YCAAWDDSVKGVIFGGGTKLTVL | VL: 118<br>CDR1: 175<br>CDR2: 194<br>CDR3: 213 |
| FBE5-E9 | EVQLVESGGGVVQPGRSLRLSCAASGFTF SSYGMHWVRQAPGKGLEWVAVISYDGSNK YYADSVKGRFTISRDNSKNTLYLQMNSLR AEDTAVYYCAKTGYGDEGEFDYWGQGTLV TVSS | VH: 89<br>CDR1: 131<br>CDR2: 135<br>CDR3: 156 | SYVLTQPPSASGTPGQRVTISCSGSISNI GSNTVNWYQQLPGTAPKLLIYSNNQRPSG GVPDRFSGSRSGTSASLAISGLQSEDEAD YYCATWDGSLNGVVFGGGTKLTVL | VL: 119<br>CDR1: 176<br>CDR2: 185<br>CDR3: 214 |
| FBE5-F2 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKDGGDGMDVWGQGTTVTVS S | VH: 90<br>CDR1: 131<br>CDR2: 135<br>CDR3: 157 | WSVLTQPPSVSAAPGQKVTISCSGSSSNI GNNYVSWYQQLPGTAPKLLIYDNNKRPSG IPDRFSGSKSGTSATLGITGLQTGDEADY YCGTWDSSLSAVVFGGGTKLTVL | VL: 120<br>CDR1: 168<br>CDR2: 187<br>CDR3: 209 |
| FBE5-F8 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCATSGDSSSPFDYWGQGTLVT VSS | VH: 91<br>CDR1: 131<br>CDR2: 135<br>CDR3: 158 | QSVLTQPPSVSAAPGQKVTISCSGSSSNI GNNYVSWYQQLPGTAPKLLIYDNNKRPSG IPDRFSGSKSGTSATLGIPGLQTGDEADY YCGTWDSSLSAVVFGGGTKLTVL | VL: 121<br>CDR1: 168<br>CDR2: 187<br>CDR3: 209 |
| FBE5-G1 | QVQLVQSGGGVVQPGRSLRLSCAASGFTF SNYGMHWVRQAPGKGLEWVVVISYDESNK YYADSVKGRFTISRDNSKNTLYLQMNSLR AEDTAVYYCAKDRSGHGDAFDIWGQGTMV AVSL | VH: 92<br>CDR1: 133<br>CDR2: 136<br>CDR3: 159 | QSVLTQPPSLSAAPGQKVTISCSGTSSNI GGNYVSWYQQLPGEAPKKLIYDNNKRPSG IPDRFSGSKSGTSATLGITGLHTGDEADY YCGTWDSGLSAGVFGGGTKLTV | VL: 122<br>CDR1: 177<br>CDR2: 187<br>CDR3: 215 |
| FBE-G5 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCAKEGDGYLDYWGQGTLVTVS S | VH: 93<br>CDR1: 131<br>CDR2: 135<br>CDR3: 160 | QSVLTQPPSVSAAPGQKVTISCSGSSSNI GNNYVSWYQQLPGTAPKLLIYENNKRPSG IPDRFSGSKSGTSATLGITGLQTGDEADY YCGTWDSSLSAVVFGGGTKLTVL | VL: 123<br>CDR1: 168<br>CDR2: 195<br>CDR3: 209 |
| FBE5-G7 | EVQLVQSGGGVVQPGRSLRLSCAASGFIF SNYGMHWVRQAPGKGLEWVAVISYDGSNK YYADSVKGRFTISRDNSKNTLYLQMNSLR AEDTAVYYC AREGVGGDYGDLPTGPYYYYGMDV WGQGTTVTVSS | VH: 94<br>CDR1: 132<br>CDR2: 135<br>CDR3: 144 | QSVLTQPPSVSAAPGQKVTISCSGSSSNI GRNFVSWYQQFPETAPKLLIFDNDRPSG IPDRFSGSKSGTSVTLGITGLQTGDEADY YCETWDSSLNAVVFGGGTKLTVL | VL: 124<br>CDR1: 178<br>CDR2: 196<br>CDR3: 216 |
| FBE5-H1 | QVQLVQSGGGVVQPGRSLRLSCAASGFTF SSYGMHWVRQAPGKGLEWVAVISYDGSNK YYADSVKGRFTISRDNSKNTLYLQMNSLR AEDTAVYYCARVYAGEEGMDVWGQGTTVT VSS | VH: 95<br>CDR1: 131<br>CDR2: 135<br>CDR3: 161 | QSVLTQPPSASGTPGQRVTISCSGSSSNI GNDPVNWYQQLPGTAPKLLIYSNDQPRSG VPDRFSGSKSGTSGSLAISGLQSEDEADY YCEAWDASLNGRVFGGGTKLTVL | VL: 125<br>CDR1: 179<br>CDR2: 197<br>CDR3: 217 |

-continued

FBE5 antibodies, raised against COA-C(311-636), shown in scFv-Fc format

| Antibody name | VH amino acid sequence | SEQ ID NO | VL amino acid sequence | SEQ ID NO |
|---|---|---|---|---|
| FBE5-H6 | QVQLQESGGGVVQPGRSLRLSCAASGFTF SSYGMHWVRQAPGKGLEWVAV<u>ISYGDSNK</u> YYADSVKGRFTISRDNSKNTLYLQMNSLR AEDTAVYYC*AKGSGYDGGRAFDY*WGQGTL VTVSS | VH: 96<br>CDR1: 131<br>CDR2: 135<br>CDR3: 149 | WAGLTQPPSASGTPGQRVTISCSGSSSNI GTNYVYWYQQLPGTAPKLLMY<u>GND</u>QRPSG VPDRFSGSKSGTSVSLAISGLRSEDEADY YC*SANDDSLSGVV*FGGGTKLTVL | VL: 126<br>CDR1: 180<br>CDR2: 198<br>CDR3: 218 |
| FBE5-H7 | QVLQVQSGGGVVQPGRSLRLSCAASGFTF SSYGMHWVRQAPGKGLEWVAV<u>ISYDGSNK</u> YYADSVKGRFTISRDNSKNTLYLQMNSLR AEDTAVYYC*AKNSAGDAFDY*WGQGTLVTV SS | VH: 97<br>CDR1: 131<br>CDR2: 135<br>CDR3: 162 | QSVLTQPPSVSVAPGKTASVTCGGDNIGS QSVHWYQQKPGQAPVLVVY<u>DDS</u>DRPSGIP ERFSGSNSGNTATLTISRVEAGDEADYYC *QVWDSRSDHVV*FGGGTKLTVL | VL: 127<br>CDR1: 181<br>CDR2: 193<br>CDR3: 219 |
| FBE5-H8 | QVQLVQSGGGVVQPGRSLRLSCAASGFTF SSYGMHWVRQAPGKGLEWVAV<u>ISYDGSNK</u> YYADSVKGRFTISRDNSKNTLYLQMNSLR AEDTAVYYC*AKSHPYHDAFDNN*WGQGTMVT VSS | VH: 98<br>CDR1: 131<br>CDR2: 135<br>CDR3: 163 | LPVLTQPPSASGTPGQRVTISCSGSSSNI GSDTVDWYQQLPGTAPKIIIY<u>SDY</u>RRASG GPDRFSGSKSGTSASLAISGLQSEDEADY YC*ATWDASLNGYV*FGTGTKVTVL | VL: 128<br>CDR1: 182<br>CDR2: 199<br>CDR3: 220 |
| LIG40-A11 | QVQLVESGGGVVQPGGSLRLSCAASGFTF DDYAMHWVRQAPGKGLEWVSL<u>ISWDGST</u> YYADSVKGRFTISRDNSLYLQMNSLR AEDTALYYC*VAARRGMDV*WGQGTTVTVSS | VH: 99<br>CDR1: 134<br>CDR2: 137<br>CDR3: 134 | KIVLTQSPLSLPVTPGEPASISCRSSQSL LYSNGNNYLDWYLQKPGQSPQLLIY<u>LGSN</u> RAPGVPDRFSGSGSGTDFTLRISRVEAED VGVYYC*MQGRQPPFT*FGPGTKVDIK | VL: 129<br>CDR1: 183<br>CDR2: 200<br>CDR3: 221 |
| LIG40-D8 | EVQLVESGGGVVQPGRSLRLSCAASGFTF SSYGMHWVRQAPGKGLEWVAV<u>IWYDGSNK</u> YYADSVKGRFTISRDNSKNTLYLQMNSLR AEDTAVYYC*ARDYHGDGFDY*WGQGTLVT VSS | VH: 100<br>CDR1: 131<br>CDR2: 138<br>CDR3: 165 | DIQMTQSPSSLSASVGDTVTITCRASQDI NNYLAWFQQKPGKAPKSLISAASLQNGVP LRFSGSASGADFTLTISGLQPEDSGTYYC *QQYDVFPIT*FGPGTKVDIK | VL: 130<br>CDR1: 184<br>CDR2: 201<br>CDR3: 222 |

CDR1 is Bold; CDR2 is bold and underlined; CDR3 is bold italicized

This table includes the sequences broken out for sake of clarity:

| Sequence No. | VH amino acid sequence | Antibody name | Other Ref: |
|---|---|---|---|
| SEQ ID NO: 71 | EVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KAGPDSYGYGMDV*W GQGTTVTVSS | FBE5-A5 | VH: 71 |
| SEQ ID NO: 72 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KAGDDDYGHYFDY*W GQGTLVTVSS | FBE5-A6 | VH: 72 |
| SEQ ID NO: 73 | QVQLVESGGGVVQPGRSLRLSCAASGFTFSSYGMHWV RQAPGKGLEWVAV<u>ISYDGSNK</u>YYADSVKGRFTISRDN SKNTLYLQMNSLRGEDTAVYYCA*REGGWEPNGLDY*WG QGTLVTVSS | FBE5-A12 | VH: 73 |
| SEQ ID NO: 74 | EVQLVESRGGVVQPGRSLRLSCAASGFTFSSYGMHWV RQAPGRGLEWVAV<u>ISYDGSNK</u>YYADSVKGRFTISRDN SKNTLYLQMNGLRSDDTAVYYCA*RGGDDYGDYFDY*WG QGTLVTVSS | FBE5-B9 | VH: 74 |
| SEQ ID NO: 75 | EVQLVETRGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*REGTYYYDSSGYYE GGFDY*WGQGTLVTVSS | FBE5-C1 | VH: 75 |
| SEQ ID NO: 76 | QMQLVQSGGGVVQPGRSLRLSCAASGFIFSNYGMHWV RQAPGKGLEWVAV<u>ISYDGSNK</u>YYADSVKGRFTISRDN SKNTLYLQMDSLRAEDTAVYYCA*REGVGGDYGDLPTG PYYYYGMDV*WGQGTTVTVSS | FBE5-C8 | VH: 76 |
| SEQ ID NO: 77 | QVQLVESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KNQEWLVPGY*WGQG TLVTVSS | FBE5-D9 | VH: 77 |

-continued

| Sequence No. | VH amino acid sequence | Antibody name | Other Ref: |
|---|---|---|---|
| SEQ ID NO: 78 | QVQLVQSGGGVVQPGRSLRLSCAASGFTFSNYGMHWV RQAPGKGLEWVAV<u>ISYDGSNK</u>YYADSVKGRFTISRDN SKNTLYLQMNSLRAEDTAVYYCA*KDSREQWLAH*WGQG TLVTVSS | FBE5-D10 | VH: 78 |
| SEQ ID NO: 79 | QMQLVQSGGGVVQPGRSLRLSCAASGFTFSSYGMHWV RQAPGKGLEWVAV<u>ISYDGSNK</u>YYADSVKGRFTISRDN SKNTLYLQMNSLRGEDTAVYYCA*REGGWEPNGLDY*WG QGTLVTVSS | FBE5-E5 | VH: 79 |
| SEQ ID NO: 80 | QMQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KEGDGDYGGVLDY*W GQGTLVTVSS | FBE5-F9 | VH: 80 |
| SEQ ID NO: 81 | QVQLQESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KDLASSGFDY*WGQG TLVTVSS | FBE5-F11 | VH: 81 |
| SEQ ID NO: 82 | QVQLVESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KGSGYDGGRAFDY*W GQGTLVTVSS | FBE5-A7 | VH: 82 |
| SEQ ID NO: 83 | QVQLVESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KEIEWDGAFDI*WGQ GTMVTVSS | FBE5-A11 | VH: 83 |
| SEQ ID NO: 84 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*TEPSRSGTGY*WGQG TLVTVSS | FBE5-B2 | VH: 84 |
| SEQ ID NO: 85 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KEAPGATGAFDI*WG QGTMVTVSS | FBE5-C5 | VH: 85 |
| SEQ ID NO: 86 | QVQLQESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KEGDGGSGMDV*WGQ GTTVTVSS | FBE5-D1 | VH: 86 |
| SEQ ID NO: 87 | QMQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KVGESEGAFDI*WGQ GTMVTVSS | FBE5-D4 | VH: 87 |
| SEQ ID NO: 88 | QVQLVESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*RVGYGDYGVLADY*W GQGTLVTVSS | FBE5-E3 | VH: 88 |
| SEQ ID NO: 89 | EVQLVESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KTGYGDEGEFDY*WG QGTLVTVSS | FBE5-E9 | VH: 89 |
| SEQ ID NO: 90 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KDGGDGMDV*WGQGT TVTVSS | FBE5-F2 | VH: 90 |
| SEQ ID NO: 91 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*TSGDSSSPFDY*WGQ GTLVTVSS | FBE5-F8 | VH: 91 |
| SEQ ID NO: 92 | QVQLVQSGGGVVQPGRSLRLSCAASGFTFSNYGMHWV RQAPGKGLEWVVV<u>ISYDESNK</u>YYADSVKGRFTISRDN SKNTLYLQMNSLRAEDTAVYYCA*KDRSGHGDAFDI*WG QGTMVAVSL | FBE5-G1 | VH: 92 |

| Sequence No. | VH amino acid sequence | Antibody name | Other Ref: |
|---|---|---|---|
| SEQ ID NO: 93 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KEGDGYLDY*WGQGT LVTVSS | FBE5-G5 | VH: 93 |
| SEQ ID NO: 94 | EVQLVQSGGGVVQPGRSLRLSCAASGFIFSNYGMHWV RQAPGKGLEWVAV<u>ISYDGSNK</u>YYADSVKGRFTISRDN SKNTLYLQMNSLRAEDTAVYYCA*REGVGGDYGDLPTG PYYYYGMD*WGQGTTVTVSS | FBE5-G7 | VH: 94 |
| SEQ ID NO: 95 | QVQLVQSGGGVVQPGRSLRLSCAASGFTFSSYGMEIW VRQAPGKGLEWVAV<u>ISYDGSNK</u>YYADSVKGRFTISRD NSKNTLYLQMNSLRAEDTAVYYCA*KVYAGEEGMDV*WG QGTTVTVSS | FBE5-H1 | VH: 95 |
| SEQ ID NO: 96 | QVQLQESGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KGSGYDGGRAFDY*W GQGTLVTVSS | FBE5-H6 | VH: 96 |
| SEQ ID NO: 97 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KNSAGDAFDY*WGQG TLVTVSS | FBE5-H7 | VH: 97 |
| SEQ ID NO: 98 | QVQLVQSGGGVVQPGRSLRLSCAASGFTFSSYGMHWV RQAPGKGLEWVAV<u>ISYDGSNK</u>YYADSVKGRFTISRDN SKNTLYLQMNSLRAEDTAVYYCA*KSHPYHDAFDI*WGQ GTMVTVSS | FBE5-H8 | VH: 98 |
| SEQ ID NO: 99 | QVQLVESGGVVVQPGGSLRLSCAASGFTFDDYAMHWV RQAPGKGLEWVSL<u>ISWDGGST</u>YYADSVKGRFTISRDN SKNSLYLQMNSLRAEDTALYYCV*AARRGMD*VWGQGTT VTVSS | LIG40-A11 | VH: 99 |
| SEQ ID NO: 100 | EVQLVESGGGVVQPGRSLRLSCAASGFTFSSYGMHWV RQAPGKGLEWVAV<u>IWYDGSNK</u>YYADSVKGRFTISRDN SKNTLYLQMNSLRAEDTAVYYCA*RDYHGDGFDY*WGQG TLVTVSS | LIG40-D8 | VH: 100 |
| SEQ ID NO: 101 | QSVLTQPPSASGTPGQRVTISCSGSSSNIGSNTVNWY QQLPGTAPKLLIY<u>SNN</u>QRPSGVPDRFSGSKSGTSASL AISGLQSEDEADYYCAA*WDDSLNGVV*FGGGTKLTVL | FBE5-A5 | VL: 101 |
| SEQ ID NO: 102 | QAGLTQPPSASGTPGQVTISCSGSSSNIGSNTVNWY QQLPGTAPKLLIY<u>SNN</u>QRPSGVPDRFSGSKSGTSASL AISGLQSEDEADYYCAA*WDDSLNGVV*FGGGTKLTVL | FBE5-A6 | VL: 102 |
| SEQ ID NO: 103 | QAVLTQPPSASGTPGQRVTISCSGSDFNVGTNYVNWY QQLPGSAPKLLIY<u>RNN</u>QRPSGVPDRFSGSKSGTSATL GITGLQTGDEADYYC*GTWDSSLSAEV*FGGGTKLTVL | FBE5-A12 | VL: 103 |
| SEQ ID NO: 104 | QSVLTQPPSVSAAPGQKVTISCSGSSSNIGNNYVSWY QQLPGTAPKLLIY<u>DNN</u>KRPSGIPDRFSGSKSGTSATL GITGLQTGDEADYYC*GTWDSSLSAAV*FGGGTKLTVL | FBE5-B9 | VL: 104 |
| SEQ ID NO: 105 | QSVLTQPPSASGTPGQRVTISCSGSSSNIGSGPVNWY QQLPGTAPKLLIY<u>SDT</u>RRPSGIPDRLSGSKSGTSASL GISGLQSEDEADYYC<u>AA</u>*WDDSLNGYA*FGSGTKVTVL | FBE5-C1 | VL: 105 |
| SEQ ID NO: 106 | QSVLTQPPSVSAAPGQKVTISCSGSSSNIGNNSVSWY QQLPGTAPKLLIY<u>DNN</u>KRPSGIPDRFSGSKSGTSATL GITGLQTGDEADYYC*ETWDSSLSAVV*FGGGTKLTVL | FBE5-C8 | VL: 106 |
| SEQ ID NO: 107 | QSALTQPASVSGSPGQSITISCTGTSSDVGGYNYVSW YQQHPGKAPKLMIY<u>DVS</u>NRPSGVSNRFSGSKSGNTAS LTISGLQAEDEADYYC*SSYTSSSTLV*FGGGTKLTVL | FBE5-D9 | VL: 107 |
| SEQ ID NO: 108 | QSVLTQPPSASGTPGQRVTISCSASSSNIGSNTVNWY QQLPGTAPKLLIY<u>SNN</u>QRPSGVPDRFSGSRSGTSASL AISGLQSEDEADYYCAA*WDDSLNALV*FGGGTKLTVL | FBE5-D10 | VL: 108 |
| SEQ ID NO: 109 | QSVLTQPPSVSAAPGQKVTISCSGSSSNIGNNYVSWY QQLPGTAPKLLIY<u>DNN</u>KRPSGIPDRFSGSKSGTSATL GITGLQTGDEADYYC*GTWDSSLSAEV*FGGGTKLTVL | FBE5-E5 | VL: 109 |

| Sequence No. | VH amino acid sequence | Antibody name | Other Ref: |
|---|---|---|---|
| SEQ ID NO: 110 | QSVLTQPPSVSAAPGQKVTISCSGSSSNIEKNYVSWY<br>QQLPGTAPKLLIY<u>DNN</u>KRPSGIPDRFSGSKSGTSATL<br>GITGLQTGDEADYYC*GTWDSSLSAVV*FGGGTKLTVL | FBE5-F9 | VL: 110 |
| SEQ ID NO: 111 | QSVLTQPPSVSAAPGQKVTISCSGSSSNIGNNYVSWY<br>QQLPGTAPKLLIY<u>DNN</u>KRPSGIPDRFSGSKSGTSATL<br>GITGLQTGDEADYYC*GTWDSSLSAEV*FGGGTKLTVL | FBE5-F11 | VL: 111 |
| SEQ ID NO: 112 | QPVLTQSSSASGTPGQRVTISCSGSSSNIGSNTVNWY<br>QQVPGTAPKLLIY<u>GNN</u>QRPSGVPDRFSGSKSGTSASL<br>AISGLQSEDEADYYC*AAWDDSLNGVV*FGGGTKLTVL | FBE5-A7 | VL: 112 |
| SEQ ID NO: 113 | QTVVTQEPSVSAAPGQKVTISCSGSSSNIGNNYVSWY<br>QQLPGTAPKLLIY<u>DNN</u>RRPSGIPDRFSGSKSGTSATL<br>GITGLQTGDEADYYC*GTWDSSLSAVV*FGGGTKLTVL | FBE5-A11 | VL: 113 |
| SEQ ID NO: 114 | QSVLTQPPSASGTPGQRVTISCSGSSSNIGSNTVNWY<br>QQLPGTAPRLVIH<u>GDN</u>RRPSGVSGRFSGSKSGASASL<br>AISGLQSEDEADYYC*TVWDSDLNGVV*FGGGTRLTVL | FBE5-B2 | VL: 114 |
| SEQ ID NO: 115 | QSVLTQPPSVSAASGQKVTISCSGSSSNIGNNYVSWY<br>QQLPGTAPKLLIY<u>DNN</u>KRPSGIPDRFSGSKSGTSATL<br>GITGLQTGDEADYYC*GTWDSSLSAEV*FGGGTKLTVL | FBE5-C5 | VL: 115 |
| SEQ ID NO: 116 | QSVLTQPPSVSEAPGQRVTISCTGSSSNIGAGYDVHW<br>YQQLPGTAPKLLIY<u>GNS</u>NRPSGVPDRFSGSKSGTSAS<br>LAISGLRSEDEADYYC*AAWDDSLSGREV*FGGGTKLTV<br>L | FBE5-D1 | VL: 116 |
| SEQ ID NO: 117 | QPVLTQPPSVSVAPRQTARITCGGNNIGRKTVHWYQQ<br>KPGQAPVLVVY<u>DDS</u>DRPSGIPERFSGSNSGNTATLII<br>SGVEAGDEADYYC*QVWDSSSDHVI*FGGGTKVTVL | FBE5-D4 | VL: 117 |
| SEQ ID NO: 118 | QSVLTQPPSVSEAPRQRVTISCSGSSSNIGNNAVNWY<br>QHLPGKAPKLLIE<u>HDD</u>HLPSGVSDRFSGSKSGTSASL<br>AISGLQPEDEADYYC*AAWDDSVKGVI*FGGGTKLTVL | FBE5-E3 | VL: 118 |
| SEQ ID NO: 119 | SYVLTQPPSASGTPGQRVTISCSGSISNIGSNTVNWY<br>QQLPGTAPKLLIY<u>SNN</u>QRPSGVPDRFSGSRSGTSASL<br>AISGLQSEDEADYYC*ATWDGSLNGVV*FGGGTKLTVL | FBE5-E9 | VL: 119 |
| SEQ ID NO: 120 | QSVLTQPPSVSAAPGQKVTISCSGSSSNIGNNYVSWY<br>QQLPGTAPKLLIY<u>DNN</u>KRPSGIPDRFSGSKSGTSATL<br>GITGLQTGDEADYYC*GTWDSSLSAVV*FGGGTKLTVL | FBE5-F2 | VL: 120 |
| SEQ ID NO: 121 | QSVLTQPPSVSAAPGQKVTISCSGSSSNIGNNYVSWY<br>QQLPGTAPKLLIY<u>DNN</u>KRPSGIPDRFSGSKSGTSATL<br>GIPGLQTGDEADYYC*GTWDSSLSAVV*FGGGTKLTVL | FBE5-F8 | VL: 121 |
| SEQ ID NO: 122 | QSVLTQPPSLSAAPGQKVTISCSGTSSNIGGNYVSWY<br>QQLPGEAPKLLIY<u>DNN</u>KRPSGIPDRFSGSKSGTSATL<br>GITGLHTGDEADYYC*GTWDSGLSAGV*FGGGTKLTV | FBE5-G1 | VL: 122 |
| SEQ ID NO: 123 | QSVLTQPPSVSAAPGQKVTISCSGSSSNIGNNYVSWY<br>QQLPGTAPKLLIY<u>ENN</u>KRPSGIPDRFSGSKSGTSATL<br>GITGLQTGDEADYYC*GTWDSSLSAVV*FGGGTKLTVL | FBE5-G5 | VL: 123 |
| SEQ ID NO: 124 | QSVLTQPPSVSAAPGQKVTISCSGSSSNIGRNFVSWY<br>QQFPETAPKLLIF<u>DND</u>NRPSGIPDRFSGSKSGTSVTL<br>GITGLQTGDEADYYC*ETWDSSLNAVV*FGGGTKLTVL | FBE5-G7 | VL: 124 |
| SEQ ID NO: 125 | QSVLTQPPSASGTPGQRVTISCSGSSSNIGNDPVNWY<br>QQLPGTAPKLLIY<u>SND</u>QRPSGVPDRFSGSKSGTSGSL<br>AISGLQSEDEADYYC*EAWDASLNGRV*FGGGTKLTVL | FBE5-H1 | VL: 125 |
| SEQ ID NO: 126 | QAGLTQPPSASGTPGQRVTISCSGSSSNIGTNYVYWY<br>QQLPGTAPKLLMY<u>GND</u>QRPSGVPDRFSGSKSGTSVSL<br>AISGLRSEDEADYYC*SAWDDSLSGVV*FGGGTKLTVL | FBE5-H6 | VL: 126 |
| SEQ ID NO: 127 | QSVLTQPPSVSVAPGKTASVTCGGDNIGSQSVHWYQQ<br>KPGQAPVLVVY<u>DDS</u>DRPSGIPERFSGSNSGNTATLTI<br>SRVEAGDEADYYC*QVWDSRSDHVV*FGGGTKLTVL | FBE5-H7 | VL: 127 |
| SEQ ID NO: 128 | LPVLTQPPSASGTPGQRVTISCSGSSSNIGSDTVDWY<br>QQLPGTAPKIIIY<u>SDY</u>RRASGVPDRFSGSKSGTSASL<br>AISGLQSEDEADYYC*ATWDASLNGYV*FGTGTKVTVL | FBE5-H8 | VL: 128 |

-continued

| Sequence No. | VH amino acid sequence | Antibody name | Other Ref: |
|---|---|---|---|
| SEQ ID NO: 129 | KIVLTQSPLSLPVTPGEPASISCRSSQSLLYSNGNNY LDWYLQKPGQSPQLLIY<u>LGS</u>NRAPGVPDRFSGSGSGT DFTLRISRVEAEDVGVYYC*MQGRQPPFT*FGPGTKVDI K | LIG40-A11 | VL: 129 |
| SEQ ID NO: 130 | DIQMTQSPSSLSASVGDTVTITCRASQDINNYLAWFQ QKPGKAPKSLIS<u>AAS</u>SLQNGVPLRFSGSASGADFTLT ISGLQPEDSGTYYC*QQYDVFPIT*FGPGTKVDIK | LIG40-D8 | VL: 130 |
| SEQ ID NO: 131 | GFTFSSYG | FBE5-A5<br>FBE5-A6<br>FBE5-A12<br>FBE5-B9<br>FBE5-C1<br>FBE5-D9<br>FBE5-E5<br>FBE5-F9<br>FBE5-F11<br>FBE5-A7<br>FBE5-A11<br>FBE5-B2<br>FBE5-C5<br>FBE5-D1<br>FBE5-D4<br>FBE5-E3<br>FBE5-E9<br>FBE5-F2<br>FBE5-F8<br>FBE5-G5<br>FBE5-H1<br>FBE5-H6<br>FBE5-H7<br>FBE5-H8<br>LIG40-D8 | CDR1: 131 |
| SEQ ID NO: 132 | GFIFSNYG | FBE5-C8<br>FBE5-G7 | CDR1: 132 |
| SEQ ID NO: 133 | GFTFSNYG | FBE5-D10<br>FBE5-G1 | CDR1: 133 |
| SEQ ID NO: 134 | GFTFDDYA | LIG40-A 11 | CDR1: 134 |
| SEQ ID NO: 135 | <u>ISYDGSNK</u> | FBE5-A5<br>FBE5-A6<br>FBE5-A12<br>FBE5-B9<br>FBE5-C1<br>FBE5-C8<br>FBE5-D9<br>FBE5-D10<br>FBE5-E5<br>FBE5-F9<br>FBE5-F11<br>FBE5-A7<br>FBE5-A11<br>FBE5-B2<br>FBE5-C5<br>FBE5-D1<br>FBE5-D4<br>FBE5-E3<br>FBE5-E9<br>FBE5-F2<br>FBE5-F8<br>FBE5-G5<br>FBE5-G7<br>FBE5-H1<br>FBE5-H6<br>FBE5-H7<br>FBE5-H8 | CDR2: 135 |
| SEQ ID NO: 136 | <u>ISYDESNK</u> | FBE5-G1 | CDR2: 136 |
| SEQ ID NO: 137 | <u>ISWDGGST</u> | LIG40-A11 | CDR2: 137 |
| SEQ ID NO: 138 | <u>IWYDGSNK</u> | LIG40-D8 | CDR2: 138 |

-continued

| Sequence No. | VH amino acid sequence | Antibody name | Other Ref: |
|---|---|---|---|
| SEQ ID NO: 139 | AKAGPDSYGYGMDV | FBE5-A5 | CDR3: 139 |
| SEQ ID NO: 140 | AKAGDDDYGHYFD | FBE5-A6 | CDR3: 140 |
| SEQ ID NO: 141 | AREGGWEPNGLDY | FBE5-A12<br>FBE5-E5 | CDR3: 141 |
| SEQ ID NO: 142 | ARGGDDYGDYFDY | FBE5-B9 | CDR3: 142 |
| SEQ ID NO: 143 | AREGTYYYDSSGYYEGGFDY | FBE5-C1 | CDR3: 143 |
| SEQ ID NO: 144 | AREGVGGDYGDLPTGPYYYYGMDV | FBE5-C8<br>FBE5-G7 | CDR3: 144 |
| SEQ ID NO: 145 | AKNQEWLVPGY | FBE5-D9 | CDR3: 145 |
| SEQ ID NO: 146 | AKDSREQWLAH | FBE5-D10 | CDR3: 146 |
| SEQ ID NO: 147 | AKEGDGDYGGVLDY | FBE5-F9 | CDR3: 147 |
| SEQ ID NO: 148 | AKDLASSGFDY | FBE5-F11 | CDR3: 148 |
| SEQ ID NO: 149 | AKGSGYDGGRAFDY | FBE5-A7<br>FBE5-H6 | CDR3: 149 |
| SEQ ID NO: 150 | AKEIEWDGAFDI | FBE5-A11 | CDR3: 150 |
| SEQ ID NO: 151 | ATEPSRSGTGY | FBE5-B2 | CDR3: 151 |
| SEQ ID NO: 152 | AKEAPGATGAFDI | FBE5-C5 | CDR3: 152 |
| SEQ ID NO: 153 | AKEGDGGSGMDV | FBE5-D1 | CDR3: 153 |
| SEQ ID NO: 154 | AKVGESEGAFDI | FBE5-D4 | CDR3: 154 |
| SEQ ID NO: 155 | ARVGYGDYGVLADY | FBE5-E3 | CDR3: 155 |
| SEQ ID NO: 156 | AKTGYGDEGEFDY | FBE5-E9 | CDR3: 156 |
| SEQ ID NO: 157 | AKDGGDGMDV | FBE5-F2 | CDR3: 157 |
| SEQ ID NO: 158 | ATSGDSSSPFDY | FBE5-F8 | CDR3: 158 |
| SEQ ID NO: 159 | AKDRSGHGDAFDI | FBE5-G1 | CDR3: 159 |
| SEQ ID NO: 160 | AKEGDGYLDY | FBE5-G5 | CDR3: 160 |
| SEQ ID NO: 161 | AKVYAGEEGMDV | FBE5-H1 | CDR3: 161 |
| SEQ ID NO: 162 | AKNSAGDAFDY | FBE5-H7 | CDR3: 162 |
| SEQ ID NO: 163 | AKSHPYHDAFDI | FBE5-H8 | CDR3: 163 |
| SEQ ID NO: 164 | VAARRGMDV | LIG40-A11 | CDR3: 164 |
| SEQ ID NO: 165 | ARDYHGDGFDY | LIG40-D8 | CDR3: 165 |
| SEQ ID NO: 166 | SSNIGSNT | FBE5-A5<br>FBE5-A6<br>FBE5-D10<br>FBE5-A7<br>FBE5-B2 | CDR1: 166 |
| SEQ ID NO: 167 | DFNVGTNY | FBE5-A12 | CDR1: 167 |
| SEQ ID NO: 168 | SSNIGNNY | FBE5-B9<br>FBE5-E5<br>FBE5-F11<br>FBE5-A11<br>FBE5-C5<br>FBE5-F2<br>FBE5-F8<br>FBE5-G5 | CDR1: 168 |
| SEQ ID NO: 169 | SSNIGSGP | FBE5-C1 | CDR1: 169 |
| SEQ ID NO: 170 | SSNIGNNS | FBE5-C8 | CDR1: 170 |

-continued

| Sequence No. | VH amino acid sequence | Antibody name | Other Ref: |
|---|---|---|---|
| SEQ ID NO: 171 | SSDVGGYNY | FBE5-D9 | CDR1: 171 |
| SEQ ID NO: 172 | SSNIEKNY | FBE5-F9 | CDR1: 172 |
| SEQ ID NO: 173 | SSNIGAGYD | FBE5-D1 | CDR1: 173 |
| SEQ ID NO: 174 | NIGRKT | FBE5-D4 | CDR1: 174 |
| SEQ ID NO: 175 | SSNIGNNA | FBE5-E3 | CDR1: 175 |
| SEQ ID NO: 176 | ISNIGSNT | FBE5-E9 | CDR1: 176 |
| SEQ ID NO: 177 | SSNIGGNY | FBE5-G1 | CDR1: 177 |
| SEQ ID NO: 178 | SSNIGRNF | FBE5-G7 | CDR1: 178 |
| SEQ ID NO: 179 | SSNIGNDP | FBE5-H1 | CDR1: 179 |
| SEQ ID NO: 180 | SSNIGTNY | FBE5-H6 | CDR1: 180 |
| SEQ ID NO: 181 | NIGSQS | FBE5-H7 | CDR1: 181 |
| SEQ ID NO: 182 | SSNIGSDT | FBE5-H8 | CDR1: 182 |
| SEQ ID NO: 183 | QSLLYSGNNY | LIG40-A11 | CDR1: 183 |
| SEQ ID NO: 184 | QDINNY | LIG40-D8 | CDR1: 184 |
| SEQ ID NO: 185 | SNN | FBE5-A5<br>FBE5-A6<br>FBE5-D10<br>FBE5-E9 | CDR2: 185 |
| SEQ ID NO: 186 | RNN | FBE5-A12 | CDR2: 186 |
| SEQ ID NO: 187 | DNN | FBE5-B9<br>FBE5-C8<br>FBE5-E5<br>FBE5-F9<br>FBE5-F11<br>FBE5-A11<br>FBE5-C5<br>FBE5-F2<br>FBE5-F8<br>FBE5-G1 | CDR2: 187 |
| SEQ ID NO: 188 | SDT | FBE5-C1 | CDR2: 188 |
| SEQ ID NO: 189 | DVS | FBE5-D9 | CDR2: 189 |
| SEQ ID NO: 190 | GNN | FBE5-A7 | CDR2: 190 |
| SEQ ID NO: 191 | GDN | FBE5-B2 | CDR2: 191 |
| SEQ ID NO: 192 | GNS | FBE5-D1 | CDR2: 192 |
| SEQ ID NO: 193 | DDS | FBE5-D4<br>FBE5-H7 | CDR2: 193 |
| SEQ ID NO: 194 | HDD | FBE5-E3 | CDR2: 194 |
| SEQ ID NO: 195 | ENN | FBE5-G5 | CDR2: 195 |
| SEQ ID NO: 196 | DND | FBE5-G7 | CDR2: 196 |
| SEQ ID NO: 197 | SND | FBE5-H1 | CDR2: 197 |
| SEQ ID NO: 198 | GND | FBE5-H6 | CDR2: 198 |
| SEQ ID NO: 199 | SDY | FBE5-H8 | CDR2: 199 |
| SEQ ID NO: 200 | LGS | LIG40-A11 | CDR2: 200 |
| SEQ ID NO: 201 | AAS | LIG40-D8 | CDR2: 201 |

-continued

| Sequence No. | VH amino acid sequence | Antibody name | Other Ref: |
|---|---|---|---|
| SEQ ID NO: 202 | AAWDDSLNGVV | FBE5-A5<br>FBE5-A6<br>FBE5-A7 | CDR3: 202 |
| SEQ ID NO: 203 | GTWDSSLSAEV | FBE5-A12<br>FBE5-E5<br>FBE5-F11<br>FBE5-C5 | CDR3: 203 |
| SEQ ID NO: 204 | GTWDSSLSAAV | FBE5-B9 | CDR3: 204 |
| SEQ ID NO: 205 | AAWDDSLNGYA | FBE5-C1 | CDR3: 205 |
| SEQ ID NO: 206 | ETWDSSLSAVV | FBE5-C8 | CDR3: 206 |
| SEQ ID NO: 207 | SSYTSSSTLV | FBE5-D9 | CDR3: 207 |
| SEQ ID NO: 208 | AAWDDSLNALV | FBE5-D10 | CDR3: 208 |
| SEQ ID NO: 209 | GTWDSSLSAVV | FBE5-F9<br>FBE5-A11<br>FBE5-F2<br>FBE5-F8<br>FBE5-G5 | CDR3: 209 |
| SEQ ID NO: 210 | TVWDSDLNGVV | FBE5-B2 | CDR3: 210 |
| SEQ ID NO: 211 | AAWDDSLSGREV | FBE5-D1 | CDR3: 211 |
| SEQ ID NO: 212 | QVWDSSSDHVI | FBE5-D4 | CDR3: 212 |
| SEQ ID NO: 213 | AAWDDSVKGVI | FBE5-E3 | CDR3: 213 |
| SEQ ID NO: 214 | ATWDGSLNGVV | FBE5-E9 | CDR3: 214 |
| SEQ ID NO: 215 | GTWDSGLSAGV | FBE5-G1 | CDR3: 215 |
| SEQ ID NO: 216 | ETWDSSLNAVV | FBE5-G7 | CDR3: 216 |
| SEQ ID NO: 217 | EAWDASLNGRV | FBE5-H1 | CDR3: 217 |
| SEQ ID NO: 218 | SAWDDSLSGVV | FBE5-H6 | CDR3: 218 |
| SEQ ID NO: 219 | QVWDSRSDHVV | FBE5-H7 | CDR3: 219 |
| SEQ ID NO: 220 | ATWDASLNGYV | FBE5-H8 | CDR3: 220 |
| SEQ ID NO: 221 | MQGRQPPFT | LIG40-A11 | CDR3: 221 |
| SEQ ID NO: 222 | QQYDVFPIT | LIG40-D8 | CDR3: 222 |

In one embodiment, the present invention includes an antibody or antigen binding fragment thereof that specifically binds an extracellular fibrinogen binding protein, wherein the antibody or antigen binding fragment thereof comprises, consists essentially of, or consists of: (a) a heavy chain CDR1 comprising the amino acid sequence selected from SEQ ID NOS:131-134; a heavy chain CDR2 comprising the amino acid sequences selected from SEQ ID NOS: 135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222. In one aspect, the antibody or antigen binding fragment thereof is a full-length antibody. In another aspect, the antibody or antigen binding fragment thereof is a humanized antibody. In another aspect, the antibody or antigen binding fragment thereof is an antigen binding fragment, wherein the antigen binding fragment comprises an Fab, a Fab', a F(ab')$_2$, a single chain Fv (scFv), a disulfide linked Fv, an IgG-CH$_2$, a F(ab')$_3$, a tetrabody, a triabody, a diabody, a (scFv)$_2$, or a scFv-Fc. In another aspect, the extracellular fibrinogen binding protein is selected from Efb, Coa or both. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In another aspect, the antibody or antigen binding fragment further comprises a collagen-like domain, a globular domain, or both. In another aspect, the antibody or antigen binding fragment further comprises a label selected from the group consisting of: a radiolabel, a fluorophore, a chromophore, an imaging agent and a metal ion, wherein the labeled antibody is a diagnostic reagent. In another aspect, the antibody or antigen binding fragment further comprises a therapeutic agent selected from an analgesic, an anti-histamine, an anti-inflammatory agent, an antibiotic, a chemotherapeutic, an immunosuppressant, a cytokine, an anti-proliferative, an antiemetic, or a cytotoxin. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present invention includes a method of making the antibody or antigen binding fragment thereof comprising, consisting essentially of, or consisting of: (a) culturing a cell expressing said antibody or antigen binding fragment thereof, wherein the antibody or antigen binding fragment thereof comprises: a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; and (b) isolating the antibody or antigen binding fragment thereof from the cultured cell, wherein the cell is a eukaryotic cell. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present invention includes an immunoconjugate having the formula (A)-(L)-(C), wherein: (A) is the antibody or antigen binding fragment of claim 1; (L) is a linker; and (C) is a cytotoxic agent; wherein the linker (L) links (A) to (C) wherein the antibody or antigen binding fragment thereof comprises, consists essentially of, or consists of: a heavy chain CDR1 comprising the amino acid sequence selected from SEQ ID NOS: SEQ ID NOS: 131-134; a heavy chain CDR2 comprising the amino acid sequences selected from SEQ ID NOS:135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222. In one aspect, the linker is selected from the group consisting of a cleavable linker, a non-cleavable linker, a hydrophilic linker, and a dicarboxylic acid based linker. In another aspect, the linker is selected from the group consisting: N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol] ester (NHS-PEG4-maleimide). In another aspect, the immunoconjugate further comprises a therapeutic agent selected from an analgesic, an anti-histamine, an anti-inflammatory agent, an antibiotic, a chemotherapeutic, an immunosuppressant, a cytokine, an anti-proliferative, an antiemetic, or a cytotoxin. In another aspect, the immunoconjugate comprises 2-6 (C), 3-4 (C), or has an average of about 3 to about 4 (C) per (A) or an average of about 3.5+/−0.5 (C) per (A). In another aspect, the immunoconjugate further comprises a pharmaceutically acceptable carrier. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present invention includes a pharmaceutical composition comprising, consisting essentially of, or consisting of: an antibody or antigen binding fragment thereof that specifically binds an extracellular fibrinogen binding protein, wherein the antibody or antigen binding fragment thereof comprises: (a) a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; and a pharmaceutically acceptable carrier. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present invention includes a method for making a monoclonal antibody comprising, consisting essentially of, or consisting of: providing an effective amount of a composition comprising a modified extracellular fibrinogen binding protein having a N-terminus modified fibrinogen binding protein that does not bind fibrinogen, a C-terminus modified complement binding protein that does not bind a complement protein or both; producing an antibody pool of the modified extracellular fibrinogen binding protein, the C-terminus modified complement binding protein, or both; screening the antibody pool to detect active antibodies; wherein the active antibodies inhibit the fibrinogen binding to extracellular fibrinogen binding protein, wherein the antibody or antigen binding fragment thereof comprises: a heavy chain CDR1 comprising the amino acid sequence selected from SEQ ID NOS: 131-134; a heavy chain CDR2 comprising the amino acid sequences selected from SEQ ID NOS:135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222; separating the active antibodies; and adding the active antibodies to a pharmaceutically acceptable carrier. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In another embodiment, the present invention includes a method of treating of a staphylococcus bacterium infection comprising consisting essentially of, or consisting of: providing a pharmacologically effective amount of a monoclonal and/or polyclonal antibody or antigen-binding fragment thereof that can specifically bind to a portion of a extracellular fibrinogen binding protein comprising antibody or antigen binding fragment thereof that specifically binds an extracellular fibrinogen binding protein, wherein the antibody or antigen binding fragment thereof comprises: (a) a heavy chain CDR1 comprising the amino acid sequence selected from SEQ ID NOS:131-134; a heavy chain CDR2 comprising the amino acid sequences selected from SEQ ID NOS:135-138; and a heavy chain CDR3 comprising the amino acid sequences selected from SEQ ID NOS:139-165); and (b) a light chain CDR1 comprising the amino acid sequence selected from SEQ ID NOS:166-184; a light chain CDR2 comprising the amino acid sequence selected from SEQ ID NOS:185-201; and a light chain CDR3 comprising the amino acid sequence selected from SEQ ID NOS:202-222, that inhibits fibrinogen binding, complement protein binding, inhibition of the shielding of the staphylococcus bacterium from recognition by a phagocytic receptor, or a combination thereof. In another aspect, the antibody or antigen binding fragment thereof comprises a heavy chain variable domain comprising the amino acid sequence selected from SEQ ID NOS: 71-100 and a light chain variable domain comprising the amino acid sequence selected from SEQ ID NOS:101-130. In one example, the variable heavy chain and variable light chain comprise, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Kügler, J., Wilke, S., Meier, D., Tomszak, F., Frenzel, A., Schirrmann, T., Dübel, S., Garritsen, H., Hock, B., Toleikis, L., Schütte, M. and Hust, M. (2015). Generation and analysis of the improved human HAL9/10 antibody phage display libraries. BMC Biotechnol. 15, 10.

Russo, G., Meier, D., Helmsing, S., Wenzel, E., Oberle, F., Frenzel, A. and Hust, M. (2018a). Parallelized Antibody Selection in Microtiter Plates. Methods Mol. Biol. 1701, 273-284.

Russo, G., Theisen, U., Fahr, W., Helmsing, S., Hust, M., Köster, R. W. and Dübel, S. (2018b). Sequence defined antibodies improve the detection of cadherin 2 (N-cadherin) during zebrafish development. New Biotechnology 45, 98-112.

Jäger, V., Büssow, K., Wagner, A., Weber, S., Hust, M., Frenzel, A. and Schirrmann, T. (2013). High level transient production of recombinant antibodies and antibody fusion proteins in HEK293 cells. BMC Biotechnol. 13, 52.

Additional Embodiments

In some embodiments, the present disclosure pertains to a method of making the antibody or antigen binding fragment thereof including: (a) culturing a cell expressing said antibody or antigen binding fragment thereof, where the antibody or antigen binding fragment thereof includes: a heavy chain CDR1 having the amino acid sequence selected from SEQ ID NOS:131-134; a heavy chain CDR2 having the amino acid sequences selected from SEQ ID NOS:135-138; and a heavy chain CDR3 having the amino acid sequences selected from SEQ ID NOS:139-165); and a light chain CDR1 having the amino acid sequence selected from SEQ ID NOS:166-184; a light chain CDR2 having the amino acid sequence selected from SEQ ID NOS:185-201; and a light chain CDR3 having the amino acid sequence selected from SEQ ID NOS:202-222; and (b) isolating the antibody or antigen binding fragment thereof from the cultured cell, where the cell is a eukaryotic cell.

In some embodiments, the variable heavy chain and the variable light chain include, respectively SEQ ID NOS:71 and 101, 72 and 102, 73 and 103, 74 and 104, 75 and 105, 76 and 106, 77 and 107, 78 and 108, 79 and 109, 80 and 110, 81 and 111, 82 and 112, 83 and 113, 84 and 114, 85 and 115, 86 and 116, 87 and 117, 88 and 118, 89 and 110, 90 and 120, 91 and 121, 92 and 122, 93 and 123, 94 and 124, 95 and 125, 96 and 126, 97 and 127, 98 and 128, 99 and 129, or 100 and 130.

In some embodiments, the antibody or the antigen binding fragment thereof includes a heavy chain variable domain having the amino acid sequence of SEQ ID NO: 81 and a light chain variable domain having the amino acid sequence of SEQ ID NO: 111.

What is claimed is:

1. An isolated antibody or antigen binding fragment thereof that specifically binds to a staphylococcal extracellular fibrinogen binding protein, wherein the antibody or the antigen binding fragment thereof comprises:
   (a) a heavy chain CDR1 comprising the amino acid sequence of SEQ ID NO: 131, a heavy chain CDR2 comprising the amino acid sequence of SEQ ID NO: 135, and a heavy chain CDR3 comprising the amino acid sequence of SEQ ID NO: 148, and
   (b) a light chain CDR1 comprising the amino acid sequence of SEQ ID NO: 168, a light chain CDR2 comprising the amino acid sequence of SEQ ID NO: 187, and a light chain CDR3 comprising the amino acid sequence of SEQ ID NO: 203.

2. The antibody or the antigen binding fragment thereof of claim 1, wherein the antibody is a full-length antibody, is a humanized antibody, or both.

3. The antibody or the antigen binding fragment thereof of claim 2, wherein the antibody binds to SEQ ID NO: 32 and SEQ ID NO: 63.

4. The antibody or the antigen binding fragment thereof of claim 1, wherein the extracellular fibrinogen binding protein is Coa protein of Staphylococcus aureus.

5. The antibody or the antigen binding fragment thereof of claim 1, wherein the antibody or the antigen binding fragment thereof comprises a heavy chain variable domain comprising the amino acid sequence of SEQ ID NO: 81 and a light chain variable domain comprising the amino acid sequence of SEQ ID NO: 111.

6. An immunoconjugate having the formula (A)-(L)-(C), wherein (A) is the antibody or the antigen binding fragment thereof of claim 1, (L) is a linker, and (C) is a cytotoxic agent.

7. The immunoconjugate of claim 6, wherein the linker is selected from the group consisting of a cleavable linker, a non-cleavable linker, a hydrophilic linker, and a dicarboxylic acid based linker, or is selected from the group consisting of N-succinimidyl 4-(2-pyridyldithio)pentanoate (SPP) or N-succinimidyl 4-(2-pyridyldithio)-2-sulfopentanoate (sulfo-SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (STAB); and N-succinimidyl-[(N-maleimidopropionamido)-tetraethyleneglycol] ester (NHS-PEG4-maleimide).

8. The immunoconjugate of claim 6, further comprising a therapeutic agent selected from an analgesic, an anti-histamine, an anti-inflammatory agent, an antibiotic, a chemotherapeutic, an immunosuppressant, a cytokine, an anti-proliferative, an antiemetic, a cytotoxin, or a pharmaceutically acceptable carrier.

9. The immunoconjugate of claim 6, wherein the immunoconjugate comprises 2-6 (C), 3-4 (C), or has an average of about 3 to about 4 (C) per (A), or an average of about 3.5+/−0.5 (C) per (A).

10. A method of making the antibody or the antigen binding fragment thereof of claim 1, the method comprising:
   (a) culturing a cell expressing the antibody or the antigen binding fragment thereof, and
   (b) isolating the antibody or the antigen binding fragment thereof from the cultured cell, wherein the cell is a eukaryotic cell.

11. The method of claim 10, wherein the antibody or the antigen binding fragment thereof comprises a heavy chain variable domain comprising the amino acid sequence of SEQ ID NO: 81 and a light chain variable domain comprising the amino acid sequence of SEQ ID NO: 111.

* * * * *

SEQUENCE LISTING

```
<160> NUMBER OF SEQ ID NOS: 230

<210> SEQ ID NO 1
<211> LENGTH: 31
<212> TYPE: PRT
<213> ORGANISM: Artificial Sequence
<220> FEATURE:
<223> OTHER INFORMATION: Synthetic peptide

<400> SEQUENCE: 1

Lys Tyr Ile Lys Phe Lys His Asp Tyr Asn Ile Leu Glu Phe Asn Asp
1               5                   10                  15

Gly Thr Phe Glu Tyr Gly Ala Arg Pro Gln Phe Asn Lys Pro Ala
            20                  25                  30
```

```
<210> SEQ ID NO 2
<211> LENGTH: 28
<212> TYPE: PRT
<213> ORGANISM: Artificial Sequence
<220> FEATURE:
<223> OTHER INFORMATION: Synthetic peptide

<400> SEQUENCE: 2

Lys Tyr Ile Lys Phe Lys His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic peptide

<400> SEQUENCE: 3

Ala Tyr Ile Lys Phe Lys His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 4
<211> LENGTH: 28
<212> TYPE: PRT
<213> ORGANISM: Artificial Sequence
<220> FEATURE:
<223> OTHER INFORMATION: Synthetic peptide

<400> SEQUENCE: 4

Lys Ala Ile Lys Phe Lys His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide

<400> SEQUENCE: 5

Lys Tyr Ala Lys Phe Lys His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Synthetic peptide

<400> SEQUENCE: 6

Lys Tyr Ile Ala Phe Lys His Asp Tyr Asn Ile Leu Glu Phe Asn Asp
1               5                   10                  15

Gly Thr Phe Glu Tyr Gly Ala Arg Pro Gln Phe Asn
            20                  25
```

<210> SEQ ID NO 7
<211> LENGTH: 28
<212> TYPE: PRT
<213> ORGANISM: Artificial Sequence
<220> FEATURE:
<223> OTHER INFORMATION: Synthetic peptide

<400> SEQUENCE: 7

Lys Tyr Ile Lys Ala Lys His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic peptide

<400> SEQUENCE: 8

Lys Tyr Ile Lys Phe Ala His Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic peptide

<400> SEQUENCE: 9

Lys Tyr Ile Lys Phe Lys Ala Asp Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Synthetic peptide

<400> SEQUENCE: 10

Lys Tyr Ile Lys Phe Lys His Ala Tyr Asn Ile Leu Glu Phe Asn Asp
1               5                   10                  15

Gly Thr Phe Glu Tyr Gly Ala Arg Pro Gln Phe Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Synthetic peptide

<400> SEQUENCE: 11

Lys Tyr Ile Lys Phe Lys His Asp Ala Asn Ile Leu Glu Phe Asn Asp
1               5                   10                  15

Gly Thr Phe Glu Tyr Gly Ala Arg Pro Gln Phe Asn

```
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic peptide

<400> SEQUENCE: 12

Lys Tyr Ile Lys Phe Lys His Asp Tyr Ala Ile Leu Glu Phe Asn Asp
1               5                   10                  15

Gly Thr Phe Glu Tyr Gly Ala Arg Pro Gln Phe Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Synthetic peptide

<400> SEQUENCE: 13

Lys Tyr Ile Lys Phe Lys His Asp Tyr Asn Ala Leu Glu Phe Asn Asp
1               5                   10                  15

Gly Thr Phe Glu Tyr Gly Ala Arg Pro Gln Phe Asn
            20                  25

<210> SEQ ID NO 14
<211> LENGTH: 28
<212> TYPE: PRT
<213> ORGANISM: Artificial Sequence
<220> FEATURE:
<223> OTHER INFORMATION: Synthetic peptide

<400> SEQUENCE: 14

Lys Tyr Ile Lys Phe Lys His Asp Tyr Asn Ile Ala Glu Phe Asn Asp
1               5                   10                  15

Gly Thr Phe Glu Tyr Gly Ala Arg Pro Gln Phe Asn
            20                  25

<210> SEQ ID NO 15
<211> LENGTH: 28
<212> TYPE: PRT
<213> ORGANISM: Artificial Sequence
<220> FEATURE:
<223> OTHER INFORMATION: Synthetic peptide

<400> SEQUENCE: 15

Lys Tyr Ile Lys Phe Lys His Asp Tyr Asn Ile Leu Ala Phe Asn Asp
1               5                   10                  15

Gly Thr Phe Glu Tyr Gly Ala Arg Pro Gln Phe Asn
            20                  25

<210> SEQ ID NO 16
<211> LENGTH: 28
<212> TYPE: PRT
<213> ORGANISM: Artificial Sequence
<220> FEATURE:
<223> OTHER INFORMATION: Synthetic peptide

<400> SEQUENCE: 16

Lys Tyr Ile Lys Phe Lys His Asp Tyr Asn Ile Leu Glu Ala Asn Asp
1               5                   10                  15
```

Gly Thr Phe Glu Tyr Gly Ala Arg Pro Gln Phe Asn
            20                  25

<210> SEQ ID NO 17
<211> LENGTH: 28
<212> TYPE: PRT
<213> ORGANISM: Artificial Sequence
<220> FEATURE:
<223> OTHER INFORMATION: Synthetic peptide

<400> SEQUENCE: 17

Lys Tyr Ile Lys Phe Lys His Asp Tyr Asn Ile Leu Glu Phe Ala Asp
1               5                   10                  15

Gly Thr Phe Glu Tyr Gly Ala Arg Pro Gln Phe Asn
            20                  25

<210> SEQ ID NO 18
<211> LENGTH: 28
<212> TYPE: PRT
<213> ORGANISM: Artificial Sequence
<220> FEATURE:
<223> OTHER INFORMATION: Synthetic peptide

<400> SEQUENCE: 18

Lys Tyr Ile Lys Phe Lys His Asp Tyr Asn Ile Leu Glu Phe Asn Ala
1               5                   10                  15

Gly Thr Phe Glu Tyr Gly Ala Arg Pro Gln Phe Asn
            20                  25

<210> SEQ ID NO 19
<211> LENGTH: 28
<212> TYPE: PRT
<213> ORGANISM: Artificial Sequence
<220> FEATURE:
<223> OTHER INFORMATION: Synthetic peptide

<400> SEQUENCE: 19

Lys Tyr Ile Lys Phe Lys His Asp Tyr Asn Ile Leu Glu Phe Asn Asp
1               5                   10                  15

Ala Thr Phe Glu Tyr Gly Ala Arg Pro Gln Phe Asn
            20                  25

<210> SEQ ID NO 20
<211> LENGTH: 28
<212> TYPE: PRT
<213> ORGANISM: Artificial Sequence
<220> FEATURE:
<223> OTHER INFORMATION: Synthetic peptide

<400> SEQUENCE: 20

Lys Tyr Ile Lys Phe Lys His Asp Tyr Asn Ile Leu Glu Phe Asn Asp
1               5                   10                  15

Gly Ala Phe Glu Tyr Gly Ala Arg Pro Gln Phe Asn
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic peptide

<400> SEQUENCE: 21

Lys Tyr Ile Lys Phe Lys His Asp Tyr Asn Ile Leu Glu Phe Asn Asp
1               5                   10                  15

Gly Thr Ala Glu Tyr Gly Ala Arg Pro Gln Phe Asn
            20                  25

<210> SEQ ID NO 22
<211> LENGTH: 28
<212> TYPE: PRT
<213> ORGANISM: Artificial Sequence
<220> FEATURE:
<223> OTHER INFORMATION: Synthetic peptide

<400> SEQUENCE: 22

Lys Tyr Ile Lys Phe Lys His Asp Tyr Asn Ile Leu Glu Phe Asn Asp
1               5                   10                  15

Gly Thr Phe Ala Tyr Gly Ala Arg Pro Gln Phe Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: Synthetic peptide

<400> SEQUENCE: 23

Lys Tyr Ile Lys Phe Lys His Asp Tyr Asn Ile Leu Glu Phe Asn Asp
1               5                   10                  15

Gly Thr Phe Glu Ala Gly Ala Arg Pro Gln Phe Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: Synthetic peptide

<400> SEQUENCE: 24

Lys Tyr Ile Lys Phe Lys His Asp Tyr Asn Ile Leu Glu Phe Asn Asp
1               5                   10                  15

Gly Thr Phe Glu Tyr Ala Ala Arg Pro Gln Phe Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: Synthetic peptide

<400> SEQUENCE: 25

Lys Tyr Ile Lys Phe Lys His Asp Tyr Asn Ile Leu Glu Phe Asn Asp
1               5                   10                  15

Gly Thr Phe Glu Tyr Gly Ser Arg Pro Gln Phe Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: Synthetic peptide

<400> SEQUENCE: 26

Lys Tyr Ile Lys Phe Lys His Asp Tyr Asn Ile Leu Glu Phe Asn Asp

```
1               5                   10                  15
Gly Thr Phe Glu Tyr Gly Ala Ala Pro Gln Phe Asn
            20                  25
```

<210> SEQ ID NO 27
<211> LENGTH: 28
<212> TYPE: PRT
<213> ORGANISM: Artificial Sequence
<220> FEATURE:
<223> OTHER INFORMATION: Synthetic peptide

<400> SEQUENCE: 27

```
Lys Tyr Ile Lys Phe Lys His Asp Tyr Asn Ile Leu Glu Phe Asn Asp
1               5                   10                  15
Gly Thr Phe Glu Tyr Gly Ala Arg Ala Gln Phe Asn
            20                  25
```

<210> SEQ ID NO 28
<211> LENGTH: 28
<212> TYPE: PRT
<213> ORGANISM: Artificial Sequence
<220> FEATURE:
<223> OTHER INFORMATION: Synthetic peptide

<400> SEQUENCE: 28

```
Lys Tyr Ile Lys Phe Lys His Asp Tyr Asn Ile Leu Glu Phe Asn Asp
1               5                   10                  15
Gly Thr Phe Glu Tyr Gly Ala Arg Pro Ala Phe Asn
            20                  25
```

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

```
Lys Tyr Ile Lys Phe Lys His Asp Tyr Asn Ile Leu Glu Phe Asn Asp
1               5                   10                  15
Gly Thr Phe Glu Tyr Gly Ala Arg Pro Gln Ala Asn
            20                  25
```

<210> SEQ ID NO 30
<211> LENGTH: 28
<212> TYPE: PRT
<213> ORGANISM: Artificial Sequence
<220> FEATURE:
<223> OTHER INFORMATION: Synthetic peptide

<400> SEQUENCE: 30

```
Lys Tyr Ile Lys Phe Lys His Asp Tyr Asn Ile Leu Glu Phe Asn Asp
1               5                   10                  15
Gly Thr Phe Glu Tyr Gly Ala Arg Pro Gln Phe Ala
            20                  25
```

<210> SEQ ID NO 31
<211> LENGTH: 21
<212> TYPE: PRT
<213> ORGANISM: Artificial Sequence
<220> FEATURE:
<223> OTHER INFORMATION: Synthetic peptide

<400> SEQUENCE: 31

Val Ser Tyr Gly Ala Arg Pro Thr Tyr Lys Lys Pro Ser Glu Thr Asn
1               5                   10                  15

Ala Tyr Asn Val Thr
            20

<210> SEQ ID NO 32
<211> LENGTH: 32
<212> TYPE: PRT
<213> ORGANISM: Artificial Sequence
<220> FEATURE:
<223> OTHER INFORMATION: Synthetic peptide

<400> SEQUENCE: 32

Lys Tyr Val Lys Tyr Arg Asp Ala Gly Thr Gly Ile Arg Glu Tyr Asn
1               5                   10                  15

Asp Gly Thr Phe Gly Tyr Glu Ala Arg Pro Arg Phe Asn Lys Pro Ser
            20                  25                  30

<210> SEQ ID NO 33
<211> LENGTH: 26
<212> TYPE: PRT
<213> ORGANISM: Artificial Sequence
<220> FEATURE:
<223> OTHER INFORMATION: Synthetic peptide

<400> SEQUENCE: 33

Glu Thr Asn Ala Tyr Asn Val Thr His Ala Asn Gly Gln Val Ser Tyr
1               5                   10                  15

Gly Ala Arg Pro Thr Tyr Lys Lys Pro Ser
            20                  25

<210> SEQ ID NO 34
<211> LENGTH: 27
<212> TYPE: PRT
<213> ORGANISM: Artificial Sequence
<220> FEATURE:
<223> OTHER INFORMATION: Synthetic peptide

<400> SEQUENCE: 34

Glu Thr Asn Ala Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 35
<211> LENGTH: 27
<212> TYPE: PRT
<213> ORGANISM: Artificial Sequence
<220> FEATURE:
<223> OTHER INFORMATION: Synthetic peptide

<400> SEQUENCE: 35

Ala Thr Asn Ala Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 36
<211> LENGTH: 27
<212> TYPE: PRT
<213> ORGANISM: Artificial Sequence
<220> FEATURE:
<223> OTHER INFORMATION: Synthetic peptide

<400> SEQUENCE: 36

Glu Ala Asn Ala Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic peptide

<400> SEQUENCE: 37

Glu Thr Ala Ala Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic peptide

<400> SEQUENCE: 38

Glu Thr Asn Ser Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 39
<211> LENGTH: 27
<212> TYPE: PRT
<213> ORGANISM: Artificial Sequence
<220> FEATURE:
<223> OTHER INFORMATION: Synthetic peptide

<400> SEQUENCE: 39

Glu Thr Asn Ala Ala Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 40
<211> LENGTH: 27
<212> TYPE: PRT
<213> ORGANISM: Artificial Sequence
<220> FEATURE:
<223> OTHER INFORMATION: Synthetic peptide

<400> SEQUENCE: 40

Glu Thr Asn Ala Tyr Ala Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 41
<211> LENGTH: 27
<212> TYPE: PRT
<213> ORGANISM: Artificial Sequence
<220> FEATURE:
<223> OTHER INFORMATION: Synthetic peptide

```
<400> SEQUENCE: 41

Glu Thr Asn Ala Tyr Asn Ala Thr His Ala Asn Gly Gln Val Ser
1               5                   10                  15

Tyr Gly Ala Arg Pro Thr Tyr Lys Lys Pro Ser
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic peptide

<400> SEQUENCE: 42

Glu Thr Asn Ala Tyr Asn Val Ala Thr His Ala Asn Gly Gln Val Ser
1               5                   10                  15

Tyr Gly Ala Arg Pro Thr Tyr Lys Lys Pro Ser
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic peptide

<400> SEQUENCE: 43

Glu Thr Asn Ala Tyr Asn Val Thr Ala His Ala Asn Gly Gln Val Ser
1               5                   10                  15

Tyr Gly Ala Arg Pro Thr Tyr Lys Lys Pro Ser
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide

<400> SEQUENCE: 44

Glu Thr Asn Ala Tyr Asn Val Thr Thr Ala Ala Asn Gly Gln Val Ser
1               5                   10                  15

Tyr Gly Ala Arg Pro Thr Tyr Lys Lys Pro Ser
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic peptide

<400> SEQUENCE: 45

Glu Thr Asn Ala Tyr Asn Val Thr Thr His Ser Asn Gly Gln Val Ser
1               5                   10                  15

Tyr Gly Ala Arg Pro Thr Tyr Lys Lys Pro Ser
            20                  25

<210> SEQ ID NO 46
<211> LENGTH: 27
<212> TYPE: PRT
<213> ORGANISM: Artificial Sequence
<220> FEATURE:
<223> OTHER INFORMATION: Synthetic peptide
```

<400> SEQUENCE: 46

Glu Thr Asn Ala Tyr Asn Val Thr Thr His Ala Ala Gly Gln Val Ser
1               5                   10                  15

Tyr Gly Ala Arg Pro Thr Tyr Lys Lys Pro Ser
            20                  25

<210> SEQ ID NO 47
<211> LENGTH: 27
<212> TYPE: PRT
<213> ORGANISM: Artificial Sequence
<220> FEATURE:
<223> OTHER INFORMATION: Synthetic peptide

<400> SEQUENCE: 47

Glu Thr Asn Ala Tyr Asn Val Thr Thr His Ala Asn Ala Gln Val Ser
1               5                   10                  15

Tyr Gly Ala Arg Pro Thr Tyr Lys Lys Pro Ser
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic peptide

<400> SEQUENCE: 48

Glu Thr Asn Ala Tyr Asn Val Thr Thr His Ala Asn Gly Ala Val Ser
1               5                   10                  15

Tyr Gly Ala Arg Pro Thr Tyr Lys Lys Pro Ser
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic peptide

<400> SEQUENCE: 49

Glu Thr Asn Ala Tyr Asn Val Thr Thr His Ala Asn Gly Gln Ala Ser
1               5                   10                  15

Tyr Gly Ala Arg Pro Thr Tyr Lys Lys Pro Ser
            20                  25

<210> SEQ ID NO 50
<211> LENGTH: 27
<212> TYPE: PRT
<213> ORGANISM: Artificial Sequence
<220> FEATURE:
<223> OTHER INFORMATION: Synthetic peptide

<400> SEQUENCE: 50

Glu Thr Asn Ala Tyr Asn Val Thr Thr His Ala Asn Gly Gln Val Ala
1               5                   10                  15

Tyr Gly Ala Arg Pro Thr Tyr Lys Lys Pro Ser
            20                  25

<210> SEQ ID NO 51
<211> LENGTH: 27
<212> TYPE: PRT
<213> ORGANISM: Artificial Sequence
<220> FEATURE:

<223> OTHER INFORMATION: Synthetic peptide

<400> SEQUENCE: 51

Glu Thr Asn Ala Tyr Asn Val Thr Thr His Ala Asn Gly Gln Val Ser
1               5                   10                  15

Ala Gly Ala Arg Pro Thr Tyr Lys Lys Pro Ser
            20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic peptide

<400> SEQUENCE: 52

Glu Thr Asn Ala Tyr Asn Val Thr Thr His Ala Asn Gly Gln Val Ser
1               5                   10                  15

Tyr Ala Ala Arg Pro Thr Tyr Lys Lys Pro Ser
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic peptide

<400> SEQUENCE: 53

Glu Thr Asn Ala Tyr Asn Val Thr Thr His Ala Asn Gly Gln Val Ser
1               5                   10                  15

Tyr Gly Ser Arg Pro Thr Tyr Lys Lys Pro Ser
            20                  25

<210> SEQ ID NO 54
<211> LENGTH: 27
<212> TYPE: PRT
<213> ORGANISM: Artificial Sequence
<220> FEATURE:
<223> OTHER INFORMATION: Synthetic peptide

<400> SEQUENCE: 54

Glu Thr Asn Ala Tyr Asn Val Thr Thr His Ala Asn Gly Gln Val Ser
1               5                   10                  15

Tyr Gly Ala Ala Pro Thr Tyr Lys Lys Pro Ser
            20                  25

<210> SEQ ID NO 55
<211> LENGTH: 27
<212> TYPE: PRT
<213> ORGANISM: Artificial Sequence
<220> FEATURE:
<223> OTHER INFORMATION: Synthetic peptide

<400> SEQUENCE: 55

Glu Thr Asn Ala Tyr Asn Val Thr Thr His Ala Asn Gly Gln Val Ser
1               5                   10                  15

Tyr Gly Ala Arg Ala Thr Tyr Lys Lys Pro Ser
            20                  25

<210> SEQ ID NO 56
<211> LENGTH: 27
<212> TYPE: PRT
<213> ORGANISM: Artificial Sequence

```
<220> FEATURE:
<223> OTHER INFORMATION: Synthetic peptide

<400> SEQUENCE: 56

Glu Thr Asn Ala Tyr Asn Val Thr Thr His Ala Asn Gly Gln Val Ser
1               5                   10                  15

Tyr Gly Ala Arg Pro Ala Tyr Lys Lys Pro Ser
            20                  25

<210> SEQ ID NO 57
<211> LENGTH: 27
<212> TYPE: PRT
<213> ORGANISM: Artificial Sequence
<220> FEATURE:
<223> OTHER INFORMATION: Synthetic peptide

<400> SEQUENCE: 57

Glu Thr Asn Ala Tyr Asn Val Thr Thr His Ala Asn Gly Gln Val Ser
1               5                   10                  15

Tyr Gly Ala Arg Pro Thr Ala Lys Lys Pro Ser
            20                  25

<210> SEQ ID NO 58
<211> LENGTH: 27
<212> TYPE: PRT
<213> ORGANISM: Artificial Sequence
<220> FEATURE:
<223> OTHER INFORMATION: Synthetic peptide

<400> SEQUENCE: 58

Glu Thr Asn Ala Tyr Asn Val Thr Thr His Ala Asn Gly Gln Val Ser
1               5                   10                  15

Tyr Gly Ala Arg Pro Thr Tyr Ala Lys Pro Ser
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic peptide

<400> SEQUENCE: 59

Glu Thr Asn Ala Tyr Asn Val Thr Thr His Ala Asn Gly Gln Val Ser
1               5                   10                  15

Tyr Gly Ala Arg Pro Thr Tyr Lys Ala Pro Ser
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic peptide

<400> SEQUENCE: 60

Glu Thr Asn Ala Tyr Asn Val Thr Thr His Ala Asn Gly Gln Val Ser
1               5                   10                  15

Tyr Gly Ala Arg Pro Thr Tyr Lys Lys Ala Ser
            20                  25

<210> SEQ ID NO 61
<211> LENGTH: 27
<212> TYPE: PRT
```

<213> ORGANISM: Artificial Sequence
<220> FEATURE:
<223> OTHER INFORMATION: Synthetic peptide

<400> SEQUENCE: 61

Glu Thr Asn Ala Tyr Asn Val Thr Thr His Ala Asn Gly Gln Val Ser
1               5                   10                  15

Tyr Gly Ala Arg Pro Thr Tyr Lys Lys Pro Ala
            20                  25

<210> SEQ ID NO 62
<211> LENGTH: 31
<212> TYPE: PRT
<213> ORGANISM: Artificial Sequence
<220> FEATURE:
<223> OTHER INFORMATION: Synthetic peptide

<400> SEQUENCE: 62

Lys Tyr Ile Lys Phe Lys His Asp Tyr Asn Ile Leu Glu Phe Asn Asp
1               5                   10                  15

Gly Thr Phe Glu Tyr Gly Ala Arg Pro Gln Phe Asn Lys Pro Ala
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Synthetic peptide

<400> SEQUENCE: 63

Lys Tyr Val Lys Tyr Arg Asp Ala Gly Thr Gly Ile Arg Glu Tyr Asn
1               5                   10                  15

Asp Gly Thr Phe Gly Tyr Glu Ala Arg Pro Arg Phe Asn Lys Pro Ser
            20                  25                  30

<210> SEQ ID NO 64
<211> LENGTH: 27
<212> TYPE: PRT
<213> ORGANISM: Artificial Sequence
<220> FEATURE:
<223> OTHER INFORMATION: Synthetic peptide

<400> SEQUENCE: 64

Pro Arg Phe Asn Lys Pro Ser Glu Thr Asn Ala Tyr Asn Val Thr Thr
1               5                   10                  15

His Ala Asn Gly Gln Val Ser Tyr Gly Ala Arg
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic peptide

<400> SEQUENCE: 65

Asn Lys Pro Ser Glu Thr Asn Ala Tyr Asn Val Thr Thr His Ala Asn
1               5                   10                  15

Gly Gln Val Ser Tyr Gly Ala Arg Pro Thr Tyr
            20                  25

<210> SEQ ID NO 66
<211> LENGTH: 27

```
<212> TYPE: PRT
<213> ORGANISM: Artificial Sequence
<220> FEATURE:
<223> OTHER INFORMATION: Synthetic peptide

<400> SEQUENCE: 66

Ala Tyr Asn Val Thr Thr His Ala Asn Gly Gln Val Ser Tyr Gly Ala
1               5                   10                  15

Arg Pro Thr Tyr Lys Lys Pro Ser Glu Thr Asn
            20                  25

<210> SEQ ID NO 67
<211> LENGTH: 27
<212> TYPE: PRT
<213> ORGANISM: Artificial Sequence
<220> FEATURE:
<223> OTHER INFORMATION: Synthetic peptide

<400> SEQUENCE: 67

Lys Lys Pro Ser Lys Thr Asn Ala Tyr Asn Val Thr Thr His Ala Asp
1               5                   10                  15

Gly Thr Ala Thr Tyr Gly Pro Arg Val Thr Lys
            20                  25

<210> SEQ ID NO 68
<211> LENGTH: 27
<212> TYPE: PRT
<213> ORGANISM: Artificial Sequence
<220> FEATURE:
<223> OTHER INFORMATION: Synthetic peptide

<400> SEQUENCE: 68

Ala Arg Pro Thr Tyr Lys Lys Pro Ser Lys Thr Asn Ala Tyr Asn Val
1               5                   10                  15

Thr Thr His Ala Asp Gly Thr Ala Thr Tyr Gly
            20                  25

<210> SEQ ID NO 69
<211> LENGTH: 27
<212> TYPE: PRT
<213> ORGANISM: Artificial Sequence
<220> FEATURE:
<223> OTHER INFORMATION: Synthetic peptide

<400> SEQUENCE: 69

Ser Tyr Gly Ala Arg Pro Thr Tyr Lys Lys Pro Ser Lys Thr Asn Ala
1               5                   10                  15

Tyr Asn Val Thr Thr His Ala Asp Gly Thr Ala
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic peptide

<400> SEQUENCE: 70

Gly Gln Val Ser Tyr Gly Ala Arg Pro Thr Tyr Lys Lys Pro Ser Lys
1               5                   10                  15

Thr Asn Ala Tyr Asn Val Thr Thr His Ala Asp
            20                  25

<210> SEQ ID NO 71
```

```
<211> LENGTH: 121
<212> TYPE: PRT
<213> ORGANISM: Artificial Sequence
<220> FEATURE:
<223> OTHER INFORMATION: Synthetic peptide

<400> SEQUENCE: 71

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Pro Asp Ser Tyr Gly Tyr Gly Met Asp Val Trp Gly
            100                 105                 110

Gln Gly Thr Thr Val Thr Val Ser Ser
        115                 120

<210> SEQ ID NO 72
<211> LENGTH: 121
<212> TYPE: PRT
<213> ORGANISM: Artificial Sequence
<220> FEATURE:
<223> OTHER INFORMATION: Synthetic peptide

<400> SEQUENCE: 72

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Asp Asp Asp Tyr Gly His Tyr Phe Asp Tyr Trp Gly
            100                 105                 110

Gln Gly Thr Leu Val Thr Val Ser Ser
        115                 120

<210> SEQ ID NO 73
<211> LENGTH: 120
<212> TYPE: PRT
<213> ORGANISM: Artificial Sequence
<220> FEATURE:
<223> OTHER INFORMATION: Synthetic peptide

<400> SEQUENCE: 73

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Glu Gly Gly Trp Glu Pro Asn Gly Leu Asp Tyr Trp Gly Gln
            100                 105                 110

Gly Thr Leu Val Thr Val Ser Ser
        115                 120

<210> SEQ ID NO 74
<211> LENGTH: 120
<212> TYPE: PRT
<213> ORGANISM: Artificial Sequence
<220> FEATURE:
<223> OTHER INFORMATION: Synthetic peptide

<400> SEQUENCE: 74

Glu Val Gln Leu Val Glu Ser Arg Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Arg Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ser Asp Thr Ala Val Tyr Tyr Cys
                85                  90                  95

Ala Arg Gly Gly Asp Asp Tyr Gly Asp Tyr Phe Asp Tyr Trp Gly Gln
            100                 105                 110

Gly Thr Leu Val Thr Val Ser Ser
        115                 120

<210> SEQ ID NO 75
<211> LENGTH: 127
<212> TYPE: PRT
<213> ORGANISM: Artificial Sequence
<220> FEATURE:
<223> OTHER INFORMATION: Synthetic peptide

<400> SEQUENCE: 75

Glu Val Gln Leu Val Glu Thr Arg Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Glu Gly Thr Tyr Tyr Tyr Asp Ser Ser Gly Tyr Tyr Glu Gly
            100                 105                 110

Gly Phe Asp Tyr Trp Gly Gln Gly Thr Leu Val Thr Val Ser Ser
        115                 120                 125
```

<210> SEQ ID NO 76
<211> LENGTH: 131
<212> TYPE: PRT
<213> ORGANISM: Artificial Sequence
<220> FEATURE:
<223> OTHER INFORMATION: Synthetic peptide

<400> SEQUENCE: 76

```
Gln Met Gln Leu Val Gln Ser Gly Gly Gly Val Gln Pro Gly Arg
1               5                   10                  15

Ser Leu Arg Leu Ser Cys Ala Ala Ser Gly Phe Ile Phe Ser Asn Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Glu Gly Val Gly Gly Asp Tyr Gly Asp Leu Pro Thr Gly Pro
            100                 105                 110

Tyr Tyr Tyr Tyr Gly Met Asp Val Trp Gly Gln Gly Thr Thr Val Thr
        115                 120                 125

Val Ser Ser
    130
```

<210> SEQ ID NO 77
<211> LENGTH: 118
<212> TYPE: PRT
<213> ORGANISM: Artificial Sequence
<220> FEATURE:
<223> OTHER INFORMATION: Synthetic peptide

<400> SEQUENCE: 77

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Gln Glu Trp Leu Val Pro Gly Tyr Trp Gly Gln Gly Thr
            100                 105                 110

Leu Val Thr Val Ser Ser
```

<210> SEQ ID NO 78
<211> LENGTH: 118
<212> TYPE: PRT
<213> ORGANISM: Artificial Sequence
<220> FEATURE:
<223> OTHER INFORMATION: Synthetic peptide

<400> SEQUENCE: 78

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Glu Gln Trp Leu Ala His Trp Gly Gln Gly Thr
            100                 105                 110

Leu Val Thr Val Ser Ser
        115

<210> SEQ ID NO 79
<211> LENGTH: 120
<212> TYPE: PRT
<213> ORGANISM: Artificial Sequence
<220> FEATURE:
<223> OTHER INFORMATION: Synthetic peptide

<400> SEQUENCE: 79

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Glu Gly Gly Trp Glu Pro Asn Gly Leu Asp Tyr Trp Gly Gln
            100                 105                 110

Gly Thr Leu Val Thr Val Ser Ser
        115                 120

<210> SEQ ID NO 80
<211> LENGTH: 121
<212> TYPE: PRT
<213> ORGANISM: Artificial Sequence
<220> FEATURE:
<223> OTHER INFORMATION: Synthetic peptide

<400> SEQUENCE: 80

```
Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Gly Asp Tyr Gly Gly Val Leu Asp Tyr Trp Gly
            100                 105                 110

Gln Gly Thr Leu Val Thr Val Ser Ser
            115                 120
```

<210> SEQ ID NO 81
<211> LENGTH: 118
<212> TYPE: PRT
<213> ORGANISM: Artificial Sequence
<220> FEATURE:
<223> OTHER INFORMATION: Synthetic peptide

<400> SEQUENCE: 81

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ala Ser Ser Gly Phe Asp Tyr Trp Gly Gln Gly Thr
            100                 105                 110

Leu Val Thr Val Ser Ser
        115
```

<210> SEQ ID NO 82
<211> LENGTH: 121
<212> TYPE: PRT
<213> ORGANISM: Artificial Sequence
<220> FEATURE:
<223> OTHER INFORMATION: Synthetic peptide

<400> SEQUENCE: 82

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Gly Tyr Asp Gly Arg Ala Phe Asp Tyr Trp Gly
            100                 105                 110

Gln Gly Thr Leu Val Thr Val Ser Ser
            115                 120

<210> SEQ ID NO 83
<211> LENGTH: 119
<212> TYPE: PRT
<213> ORGANISM: Artificial Sequence
<220> FEATURE:
<223> OTHER INFORMATION: Synthetic peptide

<400> SEQUENCE: 83

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Ile Glu Trp Asp Gly Ala Phe Asp Ile Trp Gly Gln Gly
            100                 105                 110

Thr Met Val Thr Val Ser Ser
            115

<210> SEQ ID NO 84
<211> LENGTH: 118
<212> TYPE: PRT
<213> ORGANISM: Artificial Sequence
<220> FEATURE:
<223> OTHER INFORMATION: Synthetic peptide

<400> SEQUENCE: 84

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Pro Ser Arg Ser Gly Thr Gly Tyr Trp Gly Gln Gly Thr
            100                 105                 110
```

-continued

Leu Val Thr Val Ser Ser
        115

<210> SEQ ID NO 85
<211> LENGTH: 120
<212> TYPE: PRT
<213> ORGANISM: Artificial Sequence
<220> FEATURE:
<223> OTHER INFORMATION: Synthetic peptide

<400> SEQUENCE: 85

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ala Pro Gly Ala Thr Gly Ala Phe Asp Ile Trp Gly Gln
            100                 105                 110

Gly Thr Met Val Thr Val Ser Ser
        115                 120

<210> SEQ ID NO 86
<211> LENGTH: 119
<212> TYPE: PRT
<213> ORGANISM: Artificial Sequence
<220> FEATURE:
<223> OTHER INFORMATION: Synthetic peptide

<400> SEQUENCE: 86

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Gly Gly Ser Gly Met Asp Val Trp Gly Gln Gly
            100                 105                 110

Thr Thr Val Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: Synthetic peptide

<400> SEQUENCE: 87

Gln Met Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Glu Ser Glu Ala Phe Asp Ile Trp Gly Gln Gly
            100                 105                 110

Thr Met Val Thr Val Ser Ser
        115

<210> SEQ ID NO 88
<211> LENGTH: 121
<212> TYPE: PRT
<213> ORGANISM: Artificial Sequence
<220> FEATURE:
<223> OTHER INFORMATION: Synthetic peptide

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Tyr Gly Asp Tyr Gly Val Leu Ala Asp Tyr Trp Gly
            100                 105                 110

Gln Gly Thr Leu Val Thr Val Ser Ser
        115                 120

<210> SEQ ID NO 89
<211> LENGTH: 120
<212> TYPE: PRT
<213> ORGANISM: Artificial Sequence
<220> FEATURE:
<223> OTHER INFORMATION: Synthetic peptide

<400> SEQUENCE: 89

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Gly Tyr Gly Asp Glu Gly Glu Phe Asp Tyr Trp Gly Gln
            100                 105                 110

Gly Thr Leu Val Thr Val Ser Ser
            115                 120

<210> SEQ ID NO 90
<211> LENGTH: 117
<212> TYPE: PRT
<213> ORGANISM: Artificial Sequence
<220> FEATURE:
<223> OTHER INFORMATION: Synthetic peptide

<400> SEQUENCE: 90

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Gly Asp Gly Met Asp Val Trp Gly Gln Gly Thr Thr
            100                 105                 110

Val Thr Val Ser Ser
            115

<210> SEQ ID NO 91
<211> LENGTH: 119
<212> TYPE: PRT
<213> ORGANISM: Artificial Sequence
<220> FEATURE:
<223> OTHER INFORMATION: Synthetic peptide

<400> SEQUENCE: 91

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Ser Gly Asp Ser Ser Pro Phe Asp Tyr Trp Gly Gln Gly
            100                 105                 110

Thr Leu Val Thr Val Ser Ser
        115

<210> SEQ ID NO 92
<211> LENGTH: 120
<212> TYPE: PRT
<213> ORGANISM: Artificial Sequence
<220> FEATURE:
<223> OTHER INFORMATION: Synthetic peptide

<400> SEQUENCE: 92

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Val Val Ile Ser Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser Gly His Gly Asp Ala Phe Asp Ile Trp Gly Gln
            100                 105                 110

Gly Thr Met Val Ala Val Ser Leu
        115                 120

<210> SEQ ID NO 93
<211> LENGTH: 117
<212> TYPE: PRT
<213> ORGANISM: Artificial Sequence
<220> FEATURE:
<223> OTHER INFORMATION: Synthetic peptide

<400> SEQUENCE: 93

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Gly Tyr Leu Asp Tyr Trp Gly Gln Gly Thr Leu
            100                 105                 110

Val Thr Val Ser Ser
        115

<210> SEQ ID NO 94
<211> LENGTH: 131
<212> TYPE: PRT
<213> ORGANISM: Artificial Sequence
<220> FEATURE:
<223> OTHER INFORMATION: Synthetic peptide

<400> SEQUENCE: 94

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Val Gly Gly Asp Tyr Gly Asp Leu Pro Thr Gly Pro
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 95
<211> LENGTH: 119
<212> TYPE: PRT
<213> ORGANISM: Artificial Sequence
<220> FEATURE:
<223> OTHER INFORMATION: Synthetic peptide

<400> SEQUENCE: 95

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Ala Gly Glu Glu Gly Met Asp Val Trp Gly Gln Gly
            100                 105                 110

Thr Thr Val Thr Val Ser Ser
        115

<210> SEQ ID NO 96
<211> LENGTH: 121
<212> TYPE: PRT
<213> ORGANISM: Artificial Sequence
<220> FEATURE:
<223> OTHER INFORMATION: Synthetic peptide

<400> SEQUENCE: 96

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Tyr Asp Gly Gly Arg Ala Phe Asp Tyr Trp Gly
                100                 105                 110

Gln Gly Thr Leu Val Thr Val Ser Ser
            115                 120

<210> SEQ ID NO 97
<211> LENGTH: 118
<212> TYPE: PRT
<213> ORGANISM: Artificial Sequence
<220> FEATURE:
<223> OTHER INFORMATION: Synthetic peptide

<400> SEQUENCE: 97

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ser Ala Gly Asp Ala Phe Asp Tyr Trp Gly Gln Gly Thr
                100                 105                 110

Leu Val Thr Val Ser Ser
            115

<210> SEQ ID NO 98
<211> LENGTH: 119
<212> TYPE: PRT
<213> ORGANISM: Artificial Sequence
<220> FEATURE:
<223> OTHER INFORMATION: Synthetic peptide

<400> SEQUENCE: 98

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Lys Ser His Pro Tyr His Asp Ala Phe Asp Ile Trp Gly Gln Gly
                100                 105                 110

Thr Met Val Thr Val Ser Ser
        115

<210> SEQ ID NO 99
<211> LENGTH: 116
<212> TYPE: PRT
<213> ORGANISM: Artificial Sequence
<220> FEATURE:
<223> OTHER INFORMATION: Synthetic peptide

<400> SEQUENCE: 99

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Ala Ala Arg Arg Gly Met Asp Val Trp Gly Gln Gly Thr Thr Val
                100                 105                 110

Thr Val Ser Ser
        115

<210> SEQ ID NO 100
<211> LENGTH: 118
<212> TYPE: PRT
<213> ORGANISM: Artificial Sequence
<220> FEATURE:
<223> OTHER INFORMATION: Synthetic peptide

<400> SEQUENCE: 100

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr His Gly Asp Gly Phe Asp Tyr Trp Gly Gln Gly Thr
                100                 105                 110

Leu Val Thr Val Ser Ser
        115

<210> SEQ ID NO 101
<211> LENGTH: 110
```

```
<212> TYPE: PRT
<213> ORGANISM: Artificial Sequence
<220> FEATURE:
<223> OTHER INFORMATION: Synthetic peptide

<400> SEQUENCE: 101

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: Synthetic peptide

<400> SEQUENCE: 102

Gln Ala Gly Leu Thr Gln Pro Pro Ser Ala Ser Gly Thr Pro Gly Gln
1               5                   10                  15

Gly Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 103
<211> LENGTH: 110
<212> TYPE: PRT
<213> ORGANISM: Artificial Sequence
<220> FEATURE:
<223> OTHER INFORMATION: Synthetic peptide

<400> SEQUENCE: 103

Gln Ala Val Leu Thr Gln Pro Pro Ser Ala Ser Gly Thr Pro Gly Gln
1               5                   10                  15

Arg Val Thr Ile Ser Cys Ser Gly Ser Asp Phe Asn Val Gly Thr Asn
            20                  25                  30

Tyr Val Asn Trp Tyr Gln Gln Leu Pro Gly Ser Ala Pro Lys Leu Leu
        35                  40                  45

Ile Tyr Arg Asn Asn Gln Arg Pro Ser Gly Val Pro Asp Arg Phe Ser
```

```
            50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Glu Val Phe Gly Gly Gly Thr Lys Leu Thr Val Leu
            100                 105                 110

<210> SEQ ID NO 104
<211> LENGTH: 110
<212> TYPE: PRT
<213> ORGANISM: Artificial Sequence
<220> FEATURE:
<223> OTHER INFORMATION: Synthetic peptide

<400> SEQUENCE: 104

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Ala Val Phe Gly Gly Gly Thr Lys Leu Thr Val Leu
            100                 105                 110

<210> SEQ ID NO 105
<211> LENGTH: 110
<212> TYPE: PRT
<213> ORGANISM: Artificial Sequence
<220> FEATURE:
<223> OTHER INFORMATION: Synthetic peptide

<400> SEQUENCE: 105

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Gly
                20                  25                  30

Pro Val Asn Trp Tyr Gln Gln Leu Pro Gly Thr Ala Pro Lys Leu Leu
            35                  40                  45

Ile Tyr Ser Asp Thr Arg Arg Pro Ser Gly Ile Pro Asp Arg Leu Ser
 50                  55                  60

Gly Ser Lys Ser Gly Thr Ser Ala Ser Leu Gly Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Ala Phe Gly Ser Gly Thr Lys Val Thr Val Leu
            100                 105                 110

<210> SEQ ID NO 106
<211> LENGTH: 110
<212> TYPE: PRT
<213> ORGANISM: Artificial Sequence
<220> FEATURE:
```

<223> OTHER INFORMATION: Synthetic peptide

<400> SEQUENCE: 106

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Ser Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Ser Ala Val Val Phe Gly Gly Gly Thr Lys Leu Thr Val Leu
            100                 105                 110

<210> SEQ ID NO 107
<211> LENGTH: 110
<212> TYPE: PRT
<213> ORGANISM: Artificial Sequence
<220> FEATURE:
<223> OTHER INFORMATION: Synthetic peptide

<400> SEQUENCE: 107

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110

<210> SEQ ID NO 108
<211> LENGTH: 110
<212> TYPE: PRT
<213> ORGANISM: Artificial Sequence
<220> FEATURE:
<223> OTHER INFORMATION: Synthetic peptide

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Ser Ala Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln

```
                65                  70                  75                  80
Ser Glu Asp Glu Ala Asp Tyr Tyr Cys Ala Ala Trp Asp Asp Ser Leu
                    85                  90                  95

Asn Ala Leu Val Phe Gly Gly Gly Thr Lys Leu Thr Val Leu
                100                 105                 110
```

<210> SEQ ID NO 109
<211> LENGTH: 110
<212> TYPE: PRT
<213> ORGANISM: Artificial Sequence
<220> FEATURE:
<223> OTHER INFORMATION: Synthetic peptide

<400> SEQUENCE: 109

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Glu Val Phe Gly Gly Gly Thr Lys Leu Thr Val Leu
                100                 105                 110
```

<210> SEQ ID NO 110
<211> LENGTH: 110
<212> TYPE: PRT
<213> ORGANISM: Artificial Sequence
<220> FEATURE:
<223> OTHER INFORMATION: Synthetic peptide

<400> SEQUENCE: 110

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Lys Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
                100                 105                 110
```

<210> SEQ ID NO 111
<211> LENGTH: 110
<212> TYPE: PRT
<213> ORGANISM: Artificial Sequence
<220> FEATURE:
<223> OTHER INFORMATION: Synthetic peptide

<400> SEQUENCE: 111

Gln Ser Val Leu Thr Gln Pro Pro Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Glu Val Phe Gly Gly Gly Thr Lys Leu Thr Val Leu
            100                 105                 110

<210> SEQ ID NO 112
<211> LENGTH: 110
<212> TYPE: PRT
<213> ORGANISM: Artificial Sequence
<220> FEATURE:
<223> OTHER INFORMATION: Synthetic peptide

<400> SEQUENCE: 112

Gln Pro Val Leu Thr Gln Ser Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Val Pro Gly Thr Ala Pro Lys Leu Leu
            35                  40                  45

Ile Tyr Gly Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 113
<211> LENGTH: 110
<212> TYPE: PRT
<213> ORGANISM: Artificial Sequence
<220> FEATURE:
<223> OTHER INFORMATION: Synthetic peptide

<400> SEQUENCE: 113

Gln Thr Val Val Thr Gln Glu Pro Ser Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Arg Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu

```
                    85                  90                  95

Ser Ala Val Val Phe Gly Gly Gly Thr Lys Leu Thr Val Leu
            100                 105                 110

<210> SEQ ID NO 114
<211> LENGTH: 110
<212> TYPE: PRT
<213> ORGANISM: Artificial Sequence
<220> FEATURE:
<223> OTHER INFORMATION: Synthetic peptide

<400> SEQUENCE: 114

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Arg Leu Val
            35                  40                  45

Ile His Gly Asp Asn Arg Arg Pro Ser Gly Val Ser Gly Arg Phe Ser
        50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Thr Val Trp Asp Ser Asp Leu
                85                  90                  95

Asn Gly Val Val Phe Gly Gly Gly Thr Arg Leu Thr Val Leu
            100                 105                 110

<210> SEQ ID NO 115
<211> LENGTH: 110
<212> TYPE: PRT
<213> ORGANISM: Artificial Sequence
<220> FEATURE:
<223> OTHER INFORMATION: Synthetic peptide

<400> SEQUENCE: 115

Gln Ser Val Leu Thr Gln Pro Pro Ser Val Ser Ala Ala Ser Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Glu Val Phe Gly Gly Gly Thr Lys Leu Thr Val Leu
            100                 105                 110

<210> SEQ ID NO 116
<211> LENGTH: 112
<212> TYPE: PRT
<213> ORGANISM: Artificial Sequence
<220> FEATURE:
<223> OTHER INFORMATION: Synthetic peptide

<400> SEQUENCE: 116

Gln Ser Val Leu Thr Gln Pro Pro Ser Val Ser Glu Ala Pro Gly Gln
1               5                   10                  15
```

```
Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Arg Glu Val Phe Gly Gly Gly Thr Lys Leu Thr Val Leu
            100                 105                 110

<210> SEQ ID NO 117
<211> LENGTH: 108
<212> TYPE: PRT
<213> ORGANISM: Artificial Sequence
<220> FEATURE:
<223> OTHER INFORMATION: Synthetic peptide

<400> SEQUENCE: 117

Gln Pro Val Leu Thr Gln Pro Pro Ser Val Ser Val Ala Pro Arg Gln
1               5                   10                  15

Thr Ala Arg Ile Thr Cys Gly Gly Asn Asn Ile Gly Arg Lys Thr Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Gly Val Glu Ala Gly
65                  70                  75                  80

Asp Glu Ala Asp Tyr Tyr Cys Gln Val Trp Asp Ser Ser Ser Asp His
                85                  90                  95

Val Ile Phe Gly Gly Gly Thr Lys Val Thr Val Leu
            100                 105

<210> SEQ ID NO 118
<211> LENGTH: 110
<212> TYPE: PRT
<213> ORGANISM: Artificial Sequence
<220> FEATURE:
<223> OTHER INFORMATION: Synthetic peptide

<400> SEQUENCE: 118

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln His Leu Pro Gly Lys Ala Pro Lys Leu Leu
        35                  40                  45

Ile Glu His Asp Asp His Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Pro Glu Asp Glu Ala Asp Tyr Tyr Cys Ala Ala Trp Asp Asp Ser Val
                85                  90                  95

Lys Gly Val Ile Phe Gly Gly Gly Thr Lys Leu Thr Val Leu
```

<210> SEQ ID NO 119
<211> LENGTH: 110
<212> TYPE: PRT
<213> ORGANISM: Artificial Sequence
<220> FEATURE:
<223> OTHER INFORMATION: Synthetic peptide

<400> SEQUENCE: 119

Ser Tyr Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Gly Ser Leu
                85                  90                  95

Asn Gly Val Val Phe Gly Gly Gly Thr Lys Leu Thr Val Leu
            100                 105                 110

<210> SEQ ID NO 120
<211> LENGTH: 110
<212> TYPE: PRT
<213> ORGANISM: Artificial Sequence
<220> FEATURE:
<223> OTHER INFORMATION: Synthetic peptide

<400> SEQUENCE: 120

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 121
<211> LENGTH: 110
<212> TYPE: PRT
<213> ORGANISM: Artificial Sequence
<220> FEATURE:
<223> OTHER INFORMATION: Synthetic peptide

<400> SEQUENCE: 121

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Pro Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 122
<211> LENGTH: 109
<212> TYPE: PRT
<213> ORGANISM: Artificial Sequence
<220> FEATURE:
<223> OTHER INFORMATION: Synthetic peptide

<400> SEQUENCE: 122

Gln Ser Val Leu Thr Gln Pro Pro Ser Leu Ser Ala Ala Pro Gly Gln
 1               5                  10                  15

Lys Val Thr Ile Ser Cys Ser Gly Thr Ser Ser Asn Ile Gly Gly Asn
                 20                  25                  30

Tyr Val Ser Trp Tyr Gln Gln Leu Pro Gly Glu Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu His
 65                  70                  75                  80

Thr Gly Asp Glu Ala Asp Tyr Tyr Cys Gly Thr Trp Asp Ser Gly Leu
                 85                  90                  95

Ser Ala Gly Val Phe Gly Gly Gly Thr Lys Leu Thr Val
                100                 105

<210> SEQ ID NO 123
<211> LENGTH: 110
<212> TYPE: PRT
<213> ORGANISM: Artificial Sequence
<220> FEATURE:
<223> OTHER INFORMATION: Synthetic peptide

<400> SEQUENCE: 123

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu
                100                 105                 110

-continued

<210> SEQ ID NO 124
<211> LENGTH: 110
<212> TYPE: PRT
<213> ORGANISM: Artificial Sequence
<220> FEATURE:
<223> OTHER INFORMATION: Synthetic peptide

<400> SEQUENCE: 124

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Arg Asn
            20                  25                  30

Phe Val Ser Trp Tyr Gln Gln Phe Pro Glu Thr Ala Pro Lys Leu Leu
        35                  40                  45

Ile Phe Asp Asn Asp Asn Arg Pro Ser Gly Ile Pro Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Asn Ala Val Val Phe Gly Gly Gly Thr Lys Leu Thr Val Leu
            100                 105                 110

<210> SEQ ID NO 125
<211> LENGTH: 110
<212> TYPE: PRT
<213> ORGANISM: Artificial Sequence
<220> FEATURE:
<223> OTHER INFORMATION: Synthetic peptide

<400> SEQUENCE: 125

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asp
            20                  25                  30

Pro Val Asn Trp Tyr Gln Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala Asp Tyr Tyr Cys Glu Ala Trp Asp Ala Ser Leu
                85                  90                  95

Asn Gly Arg Val Phe Gly Gly Gly Thr Lys Leu Thr Val Leu
            100                 105                 110

<210> SEQ ID NO 126
<211> LENGTH: 110
<212> TYPE: PRT
<213> ORGANISM: Artificial Sequence
<220> FEATURE:
<223> OTHER INFORMATION: Synthetic peptide

<400> SEQUENCE: 126

Gln Ala Gly Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Tyr Val Tyr Trp Tyr Gln Gln Leu Pro Gly Thr Ala Pro Lys Leu Leu
        35                  40                  45

```
Met Tyr Gly Asn Asp Gln Arg Pro Ser Gly Val Pro Asp Arg Phe Ser
        50                  55                  60

Gly Ser Lys Ser Gly Thr Ser Val Ser Leu Ala Ile Ser Gly Leu Arg
 65                  70                  75                  80

Ser Glu Asp Glu Ala Asp Tyr Tyr Cys Ser Ala Trp Asp Ser Ser Leu
                85                  90                  95

Ser Gly Val Val Phe Gly Gly Gly Thr Lys Leu Thr Val Leu
            100                 105                 110

<210> SEQ ID NO 127
<211> LENGTH: 108
<212> TYPE: PRT
<213> ORGANISM: Artificial Sequence
<220> FEATURE:
<223> OTHER INFORMATION: Synthetic peptide

<400> SEQUENCE: 127

Gln Ser Val Leu Thr Gln Pro Pro Ser Val Ser Val Ala Pro Gly Lys
 1               5                  10                  15

Thr Ala Ser Val Thr Cys Gly Gly Asp Asn Ile Gly Ser Gln Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Arg Ser Asp His
                85                  90                  95

Val Val Phe Gly Gly Gly Thr Lys Leu Thr Val Leu
            100                 105

<210> SEQ ID NO 128
<211> LENGTH: 110
<212> TYPE: PRT
<213> ORGANISM: Artificial Sequence
<220> FEATURE:
<223> OTHER INFORMATION: Synthetic peptide

<400> SEQUENCE: 128

Leu Pro Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asp
                20                  25                  30

Thr Val Asp Trp Tyr Gln Gln Leu Pro Gly Thr Ala Pro Lys Ile Ile
            35                  40                  45

Ile Tyr Ser Asp Tyr Arg Arg Ala Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Ala Ser Leu
                85                  90                  95

Asn Gly Tyr Val Phe Gly Thr Gly Thr Lys Val Thr Val Leu
            100                 105                 110

<210> SEQ ID NO 129
<211> LENGTH: 112
<212> TYPE: PRT
```

<213> ORGANISM: Artificial Sequence
<220> FEATURE:
<223> OTHER INFORMATION: Synthetic peptide

<400> SEQUENCE: 129

Lys Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Pro Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Arg Gln Pro Pro Phe Thr Phe Gly Pro Gly Thr Lys Val Asp Ile Lys
            100                 105                 110

<210> SEQ ID NO 130
<211> LENGTH: 107
<212> TYPE: PRT
<213> ORGANISM: Artificial Sequence
<220> FEATURE:
<223> OTHER INFORMATION: Synthetic peptide

<400> SEQUENCE: 130

Asp Ile Gln Met Thr Gln Ser Pro Ser Ser Leu Ser Ala Ser Val Gly
1               5                   10                  15

Asp Thr Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Ser Ala Ala Ser Ser Leu Gln Asn Gly Val Pro Leu Arg Phe Ser Gly
    50                  55                  60

Ser Ala Ser Gly Ala Asp Phe Thr Leu Thr Ile Ser Gly Leu Gln Pro
65                  70                  75                  80

Glu Asp Ser Gly Thr Tyr Tyr Cys Gln Gln Tyr Asp Val Phe Pro Ile
                85                  90                  95

Thr Phe Gly Pro Gly Thr Lys Val Asp Ile Lys
            100                 105

<210> SEQ ID NO 131
<211> LENGTH: 8
<212> TYPE: PRT
<213> ORGANISM: Artificial Sequence
<220> FEATURE:
<223> OTHER INFORMATION: Synthetic peptide

<400> SEQUENCE: 131

Gly Phe Thr Phe Ser Ser Tyr Gly
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 132

Gly Phe Ile Phe Ser Asn Tyr Gly
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic peptide

<400> SEQUENCE: 133

Gly Phe Thr Phe Ser Asn Tyr Gly
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic peptide

<400> SEQUENCE: 134

Gly Phe Thr Phe Asp Asp Tyr Ala
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic peptide

<400> SEQUENCE: 135

Ile Ser Tyr Asp Gly Ser Asn Lys
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic peptide

<400> SEQUENCE: 136

Ile Ser Tyr Asp Glu Ser Asn Lys
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic peptide

<400> SEQUENCE: 137

Ile Ser Trp Asp Gly Gly Ser Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic peptide

<400> SEQUENCE: 138
```

```
Ile Trp Tyr Asp Gly Ser Asn Lys
1               5

<210> SEQ ID NO 139
<211> LENGTH: 14
<212> TYPE: PRT
<213> ORGANISM: Artificial Sequence
<220> FEATURE:
<223> OTHER INFORMATION: Synthetic peptide

<400> SEQUENCE: 139

Ala Lys Ala Gly Pro Asp Ser Tyr Gly Tyr Gly Met Asp Val
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic peptide

<400> SEQUENCE: 140

Ala Lys Ala Gly Asp Asp Asp Tyr Gly His Tyr Phe Asp
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic peptide

<400> SEQUENCE: 141

Ala Arg Glu Gly Gly Trp Glu Pro Asn Gly Leu Asp Tyr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic peptide

<400> SEQUENCE: 142

Ala Arg Gly Gly Asp Asp Tyr Gly Asp Tyr Phe Asp Tyr
1               5                   10

<210> SEQ ID NO 143
<211> LENGTH: 20
<212> TYPE: PRT
<213> ORGANISM: Artificial Sequence
<220> FEATURE:
<223> OTHER INFORMATION: Synthetic peptide

<400> SEQUENCE: 143

Ala Arg Glu Gly Thr Tyr Tyr Tyr Asp Ser Ser Gly Tyr Tyr Glu Gly
1               5                   10                  15

Gly Phe Asp Tyr
            20

<210> SEQ ID NO 144
<211> LENGTH: 24
<212> TYPE: PRT
<213> ORGANISM: Artificial Sequence
<220> FEATURE:
<223> OTHER INFORMATION: Synthetic peptide
```

<400> SEQUENCE: 144

Ala Arg Glu Gly Val Gly Gly Asp Tyr Gly Asp Leu Pro Thr Gly Pro
1               5                   10                  15
Tyr Tyr Tyr Tyr Gly Met Asp Val
            20

<210> SEQ ID NO 145
<211> LENGTH: 11
<212> TYPE: PRT
<213> ORGANISM: Artificial Sequence
<220> FEATURE:
<223> OTHER INFORMATION: Synthetic peptide

<400> SEQUENCE: 145

Ala Lys Asn Gln Glu Trp Leu Val Pro Gly Tyr
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic peptide

<400> SEQUENCE: 146

Ala Lys Asp Ser Arg Glu Gln Trp Leu Ala His
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthetic peptide

<400> SEQUENCE: 147

Ala Lys Glu Gly Asp Gly Asp Tyr Gly Gly Val Leu Asp Tyr
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic peptide

<400> SEQUENCE: 148

Ala Lys Asp Leu Ala Ser Ser Gly Phe Asp Tyr
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Synthetic peptide

<400> SEQUENCE: 149

Ala Lys Gly Ser Gly Tyr Asp Gly Gly Arg Ala Phe Asp Tyr
1               5                   10

<210> SEQ ID NO 150
<211> LENGTH: 12
<212> TYPE: PRT
<213> ORGANISM: Artificial Sequence

```
<220> FEATURE:
<223> OTHER INFORMATION: Synthetic peptide

<400> SEQUENCE: 150

Ala Lys Glu Ile Glu Trp Asp Gly Ala Phe Asp Ile
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Synthetic peptide

<400> SEQUENCE: 151

Ala Thr Glu Pro Ser Arg Ser Gly Thr Gly Tyr
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic peptide

<400> SEQUENCE: 152

Ala Lys Glu Ala Pro Gly Ala Thr Gly Ala Phe Asp Ile
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic peptide

<400> SEQUENCE: 153

Ala Lys Glu Gly Asp Gly Gly Ser Gly Met Asp Val
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Synthetic peptide

<400> SEQUENCE: 154

Ala Lys Val Gly Glu Ser Glu Gly Ala Phe Asp Ile
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Synthetic peptide

<400> SEQUENCE: 155

Ala Arg Val Gly Tyr Gly Asp Tyr Gly Val Leu Ala Asp Tyr
1               5                   10

<210> SEQ ID NO 156
<211> LENGTH: 13
<212> TYPE: PRT
<213> ORGANISM: Artificial Sequence
<220> FEATURE:
```

```
<223> OTHER INFORMATION: Synthetic peptide

<400> SEQUENCE: 156

Ala Lys Thr Gly Tyr Gly Asp Glu Gly Glu Phe Asp Tyr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic peptide

<400> SEQUENCE: 157

Ala Lys Asp Gly Gly Asp Gly Met Asp Val
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Synthetic peptide

<400> SEQUENCE: 158

Ala Thr Ser Gly Asp Ser Ser Ser Pro Phe Asp Tyr
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic peptide

<400> SEQUENCE: 159

Ala Lys Asp Arg Ser Gly His Gly Asp Ala Phe Asp Ile
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic peptide

<400> SEQUENCE: 160

Ala Lys Glu Gly Asp Gly Tyr Leu Asp Tyr
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic peptide

<400> SEQUENCE: 161

Ala Lys Val Tyr Ala Gly Glu Glu Gly Met Asp Val
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic peptide
```

```
<400> SEQUENCE: 162

Ala Lys Asn Ser Ala Gly Asp Ala Phe Asp Tyr
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic peptide

<400> SEQUENCE: 163

Ala Lys Ser His Pro Tyr His Asp Ala Phe Asp Ile
1               5                   10

<210> SEQ ID NO 164
<211> LENGTH: 9
<212> TYPE: PRT
<213> ORGANISM: Artificial Sequence
<220> FEATURE:
<223> OTHER INFORMATION: Synthetic peptide

<400> SEQUENCE: 164

Val Ala Ala Arg Arg Gly Met Asp Val
1               5

<210> SEQ ID NO 165
<211> LENGTH: 11
<212> TYPE: PRT
<213> ORGANISM: Artificial Sequence
<220> FEATURE:
<223> OTHER INFORMATION: Synthetic peptide

<400> SEQUENCE: 165

Ala Arg Asp Tyr His Gly Asp Gly Phe Asp Tyr
1               5                   10

<210> SEQ ID NO 166
<211> LENGTH: 8
<212> TYPE: PRT
<213> ORGANISM: Artificial Sequence
<220> FEATURE:
<223> OTHER INFORMATION: Synthetic peptide

<400> SEQUENCE: 166

Ser Ser Asn Ile Gly Ser Asn Thr
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic peptide

<400> SEQUENCE: 167

Asp Phe Asn Val Gly Thr Asn Tyr
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 168

Ser Ser Asn Ile Gly Asn Asn Tyr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide

<400> SEQUENCE: 169

Ser Ser Asn Ile Gly Ser Gly Pro
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic peptide

<400> SEQUENCE: 170

Ser Ser Asn Ile Gly Asn Asn Ser
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic peptide

<400> SEQUENCE: 171

Ser Ser Asp Val Gly Gly Tyr Asn Tyr
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic peptide

<400> SEQUENCE: 172

Ser Ser Asn Ile Glu Lys Asn Tyr
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic peptide

<400> SEQUENCE: 173

Ser Ser Asn Ile Gly Ala Gly Tyr Asp
1               5

<210> SEQ ID NO 174
<211> LENGTH: 6
<212> TYPE: PRT
<213> ORGANISM: Artificial Sequence
<220> FEATURE:
<223> OTHER INFORMATION: Synthetic peptide

<400> SEQUENCE: 174
```

```
Asn Ile Gly Arg Lys Thr
1               5

<210> SEQ ID NO 175
<211> LENGTH: 8
<212> TYPE: PRT
<213> ORGANISM: Artificial Sequence
<220> FEATURE:
<223> OTHER INFORMATION: Synthetic peptide

<400> SEQUENCE: 175

Ser Ser Asn Ile Gly Asn Asn Ala
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic peptide

<400> SEQUENCE: 176

Ile Ser Asn Ile Gly Ser Asn Thr
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic peptide

<400> SEQUENCE: 177

Ser Ser Asn Ile Gly Gly Asn Tyr
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic peptide

<400> SEQUENCE: 178

Ser Ser Asn Ile Gly Arg Asn Phe
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic peptide

<400> SEQUENCE: 179

Ser Ser Asn Ile Gly Asn Asp Pro
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic peptide

<400> SEQUENCE: 180
```

```
Ser Ser Asn Ile Gly Thr Asn Tyr
1               5

<210> SEQ ID NO 181
<211> LENGTH: 6
<212> TYPE: PRT
<213> ORGANISM: Artificial Sequence
<220> FEATURE:
<223> OTHER INFORMATION: Synthetic peptide

<400> SEQUENCE: 181

Asn Ile Gly Ser Gln Ser
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic peptide

<400> SEQUENCE: 182

Ser Ser Asn Ile Gly Ser Asp Thr
1               5

<210> SEQ ID NO 183
<211> LENGTH: 11
<212> TYPE: PRT
<213> ORGANISM: Artificial Sequence
<220> FEATURE:
<223> OTHER INFORMATION: Synthetic peptide

<400> SEQUENCE: 183

Gln Ser Leu Leu Tyr Ser Asn Gly Asn Asn Tyr
1               5                   10

<210> SEQ ID NO 184
<211> LENGTH: 6
<212> TYPE: PRT
<213> ORGANISM: Artificial Sequence
<220> FEATURE:
<223> OTHER INFORMATION: Synthetic peptide

<400> SEQUENCE: 184

Gln Asp Ile Asn Asn Tyr
1               5

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188
```

```
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
```

```
<210> SEQ ID NO 200
<400> SEQUENCE: 200

000

<210> SEQ ID NO 201
<400> SEQUENCE: 201

000

<210> SEQ ID NO 202
<211> LENGTH: 11
<212> TYPE: PRT
<213> ORGANISM: Artificial Sequence
<220> FEATURE:
<223> OTHER INFORMATION: Synthetic peptide

<400> SEQUENCE: 202

Ala Ala Trp Asp Asp Ser Leu Asn Gly Val Val
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Synthetic peptide

<400> SEQUENCE: 203

Gly Thr Trp Asp Ser Ser Leu Ser Ala Glu Val
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Synthetic peptide

<400> SEQUENCE: 204

Gly Thr Trp Asp Ser Ser Leu Ser Ala Ala Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthetic peptide

<400> SEQUENCE: 205

Ala Ala Trp Asp Asp Ser Leu Asn Gly Tyr Ala
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Synthetic peptide

<400> SEQUENCE: 206

Glu Thr Trp Asp Ser Ser Leu Ser Ala Val Val
```

```
1               5                   10
```

<210> SEQ ID NO 207
<211> LENGTH: 10
<212> TYPE: PRT
<213> ORGANISM: Artificial Sequence
<220> FEATURE:
<223> OTHER INFORMATION: Synthetic peptide

<400> SEQUENCE: 207

```
Ser Ser Tyr Thr Ser Ser Ser Thr Leu Val
1               5                   10
```

<210> SEQ ID NO 208
<211> LENGTH: 11
<212> TYPE: PRT
<213> ORGANISM: Artificial Sequence
<220> FEATURE:
<223> OTHER INFORMATION: Synthetic peptide

<400> SEQUENCE: 208

```
Ala Ala Trp Asp Asp Ser Leu Asn Ala Leu Val
1               5                   10
```

<210> SEQ ID NO 209
<211> LENGTH: 11
<212> TYPE: PRT
<213> ORGANISM: Artificial Sequence
<220> FEATURE:
<223> OTHER INFORMATION: Synthetic peptide

<400> SEQUENCE: 209

```
Gly Thr Trp Asp Ser Ser Leu Ser Ala Val Val
1               5                   10
```

<210> SEQ ID NO 210
<211> LENGTH: 11
<212> TYPE: PRT
<213> ORGANISM: Artificial Sequence
<220> FEATURE:
<223> OTHER INFORMATION: Synthetic peptide

<400> SEQUENCE: 210

```
Thr Val Trp Asp Ser Asp Leu Asn Gly Val Val
1               5                   10
```

<210> SEQ ID NO 211
<211> LENGTH: 12
<212> TYPE: PRT
<213> ORGANISM: Artificial Sequence
<220> FEATURE:
<223> OTHER INFORMATION: Synthetic peptide

<400> SEQUENCE: 211

```
Ala Ala Trp Asp Asp Ser Leu Ser Gly Arg Glu Val
1               5                   10
```

<210> SEQ ID NO 212
<211> LENGTH: 11
<212> TYPE: PRT
<213> ORGANISM: Artificial Sequence
<220> FEATURE:
<223> OTHER INFORMATION: Synthetic peptide

<400> SEQUENCE: 212

```
Gln Val Trp Asp Ser Ser Ser Asp His Val Ile
1               5                   10
```

<210> SEQ ID NO 213
<211> LENGTH: 11
<212> TYPE: PRT
<213> ORGANISM: Artificial Sequence
<220> FEATURE:
<223> OTHER INFORMATION: Synthetic peptide

<400> SEQUENCE: 213

Ala Ala Trp Asp Asp Ser Val Lys Gly Val Ile
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Synthetic peptide

<400> SEQUENCE: 214

Ala Thr Trp Asp Gly Ser Leu Asn Gly Val Val
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthetic peptide

<400> SEQUENCE: 215

Gly Thr Trp Asp Ser Gly Leu Ser Ala Gly Val
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Synthetic peptide

<400> SEQUENCE: 216

Glu Thr Trp Asp Ser Ser Leu Asn Ala Val Val
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic peptide

<400> SEQUENCE: 217

Glu Ala Trp Asp Ala Ser Leu Asn Gly Arg Val
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic peptide

<400> SEQUENCE: 218

Ser Ala Trp Asp Asp Ser Leu Ser Gly Val Val
1               5                   10

```
<210> SEQ ID NO 219
<211> LENGTH: 11
<212> TYPE: PRT
<213> ORGANISM: Artificial Sequence
<220> FEATURE:
<223> OTHER INFORMATION: Synthetic peptide

<400> SEQUENCE: 219

Gln Val Trp Asp Ser Arg Ser Asp His Val Val
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic peptide

<400> SEQUENCE: 220

Ala Thr Trp Asp Ala Ser Leu Asn Gly Tyr Val
1               5                   10

<210> SEQ ID NO 221
<211> LENGTH: 9
<212> TYPE: PRT
<213> ORGANISM: Artificial Sequence
<220> FEATURE:
<223> OTHER INFORMATION: Synthetic peptide

<400> SEQUENCE: 221

Met Gln Gly Arg Gln Pro Pro Phe Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic peptide

<400> SEQUENCE: 222

Gln Gln Tyr Asp Val Phe Pro Ile Thr
1               5

<210> SEQ ID NO 223
<211> LENGTH: 49
<212> TYPE: PRT
<213> ORGANISM: Artificial Sequence
<220> FEATURE:
<223> OTHER INFORMATION: Synthetic peptide

<400> SEQUENCE: 223

Glu Gly Ser Ser Ser Lys Leu Glu Ile Lys Pro Gln Gly Thr Glu Ser
1               5                   10                  15

Thr Leu Lys Gly Thr Gln Gly Glu Ser Ser Asp Ile Glu Val Lys Pro
            20                  25                  30

Gln Ala Thr Glu Thr Thr Glu Ala Ser Gln Tyr Gly Pro Pro Gln Phe
        35                  40                  45

Asn

<210> SEQ ID NO 224
<211> LENGTH: 50
<212> TYPE: PRT
<213> ORGANISM: Artificial Sequence
<220> FEATURE:
```

<223> OTHER INFORMATION: Synthetic peptide

<400> SEQUENCE: 224

Lys Thr Pro Lys Tyr Val Lys Tyr Arg Asp Ala Gly Thr Gly Ile Arg
1               5                   10                  15

Glu Tyr Asn Asp Gly Thr Phe Gly Tyr Glu Ala Arg Pro Arg Phe Asn
            20                  25                  30

Lys Pro Ser Glu Thr Asn Ala Tyr Asn Val Thr Thr His Ala Asn Lys
        35                  40                  45

Gly Gln
    50

<210> SEQ ID NO 225
<211> LENGTH: 27
<212> TYPE: PRT
<213> ORGANISM: Artificial Sequence
<220> FEATURE:
<223> OTHER INFORMATION: Synthetic peptide

<400> SEQUENCE: 225

Glu Thr Asn Ala Tyr Asn Val Thr Thr His Ala Asn Gly Gln Val Ser
1               5                   10                  15

Tyr Gly Ala Arg Pro Thr Tyr Lys Lys Pro Ser
            20                  25

<210> SEQ ID NO 226
<211> LENGTH: 27
<212> TYPE: PRT
<213> ORGANISM: Artificial Sequence
<220> FEATURE:
<223> OTHER INFORMATION: Synthetic peptide

<400> SEQUENCE: 226

Glu Thr Asn Ala Tyr Asn Val Thr Thr His Ala Asn Gly Gln Val Ser
1               5                   10                  15

Tyr Gly Ala Arg Pro Thr Gln Asn Lys Pro Ser
            20                  25

<210> SEQ ID NO 227
<211> LENGTH: 27
<212> TYPE: PRT
<213> ORGANISM: Artificial Sequence
<220> FEATURE:
<223> OTHER INFORMATION: Synthetic peptide

<400> SEQUENCE: 227

Lys Thr Asn Ala Tyr Asn Val Thr Thr His Gly Asn Gly Gln Val Ser
1               5                   10                  15

Tyr Gly Ala Arg Pro Thr Gln Asn Lys Pro Ser
            20                  25

<210> SEQ ID NO 228
<211> LENGTH: 27
<212> TYPE: PRT
<213> ORGANISM: Artificial Sequence
<220> FEATURE:
<223> OTHER INFORMATION: Synthetic peptide

<400> SEQUENCE: 228

Lys Thr Asn Ala Tyr Asn Val Thr Thr His Ala Asn Gly Gln Val Ser
1               5                   10                  15

Tyr Gly Ala Arg Pro Thr Tyr Lys Lys Pro Ser
            20                  25

```
<210> SEQ ID NO 229
<211> LENGTH: 23
<212> TYPE: PRT
<213> ORGANISM: Artificial Sequence
<220> FEATURE:
<223> OTHER INFORMATION: Synthetic peptide

<400> SEQUENCE: 229

Lys Thr Asn Ala Tyr Asn Val Thr Thr His Ala Asp Gly Thr Ala Thr
1               5                   10                  15

Tyr Gly Pro Arg Val Thr Lys
            20

<210> SEQ ID NO 230
<211> LENGTH: 6
<212> TYPE: PRT
<213> ORGANISM: Artificial Sequence
<220> FEATURE:
<223> OTHER INFORMATION: Synthetic peptide

<400> SEQUENCE: 230

Gly Phe Pro Gly Glu Arg
1               5
```